(12) United States Patent
Amino et al.

(10) Patent No.: US 7,795,296 B2
(45) Date of Patent: Sep. 14, 2010

(54) CRYSTALS OF NON-NATURAL-TYPE STEREOISOMER SALT OF MONATIN AND USE THEREOF

(75) Inventors: Yusuke Amino, Kawasaki (JP); Kazuko Yuzawa, Kawasaki (JP); Kenichi Mori, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 66 days.

(21) Appl. No.: 10/856,756

(22) Filed: Jun. 1, 2004

(65) Prior Publication Data

US 2005/0020508 A1 Jan. 27, 2005

Related U.S. Application Data

(63) Continuation of application No. PCT/JP02/12472, filed on Nov. 29, 2002.

(30) Foreign Application Priority Data

Nov. 30, 2001 (JP) .............................. 2001-366053
Jun. 21, 2002 (JP) .............................. 2002-182032

(51) Int. Cl.
  A61K 31/40 (2006.01)
  C07D 209/18 (2006.01)
(52) U.S. Cl. ..................................... 514/419; 548/495
(58) Field of Classification Search ................ 548/495; 426/548; 514/419
  See application file for complete search history.

(56) References Cited

U.S. PATENT DOCUMENTS

| | | | |
|---|---|---|---|
| 5,128,164 A | 7/1992 | Van Wyk et al. | |
| 5,128,482 A | 7/1992 | Olivier et al. | |
| 5,994,559 A | 11/1999 | Abushanab et al. | |
| 7,241,599 B2 | 7/2007 | Sugiyama et al. | |
| 7,351,569 B2 | 4/2008 | Sugiyama et al. | |
| 7,371,549 B2 | 5/2008 | Sugiyama et al. | |
| 7,390,909 B2 | 6/2008 | Kawahara et al. | |
| 7,402,412 B2 | 7/2008 | Sugiyama et al. | |
| 7,432,100 B2 | 10/2008 | Sugiyama et al. | |
| 2005/0020508 A1 | 1/2005 | Amino et al. | |
| 2006/0014819 A1* | 1/2006 | Mori et al. | 514/419 |
| 2006/0154343 A1 | 7/2006 | Mori et al. | |
| 2007/0072277 A1 | 3/2007 | Sugiyama et al. | |
| 2008/0091032 A1 | 4/2008 | Kawahara et al. | |
| 2008/0193975 A1 | 8/2008 | Sugiyama et al. | |
| 2008/0193984 A1 | 8/2008 | Sugiyama et al. | |
| 2008/0207920 A1 | 8/2008 | Kawahara et al. | |
| 2008/0318290 A1 | 12/2008 | Sugiyama et al. | |
| 2009/0259052 A1 | 10/2009 | Kawahara et al. | |

FOREIGN PATENT DOCUMENTS

| | | |
|---|---|---|
| EP | 0 438 314 A1 | 7/1991 |
| GB | 2 205 834 A | 12/1988 |
| JP | 4-217954 | 8/1992 |
| JP | 2002-60382 | 2/2002 |

OTHER PUBLICATIONS

Abushanab et al. 1999, CAS: 131:351675.*
Nippon Nogei Kagaku Kaishl, (2000), 74 (special extra issue), Koen Yoshishu, p. 221.
K. Nakamura, et al., "Total Synthesis of Montatin", Organic Letters, vol. 2, No. 19, pp. 2967-2970, (2000).
C. Holzapfel, "A Simple Cycloaddition Approach to a Racemate of the Natural Sweetener Monatin", Synthetic Communications, 24(22), pp. 3197-3211, (1994).
Robert Vleggaar, et al. "Structure Elucidation of Monatin, a High-intensity Sweetener Isolated from the Plant *Schlerochiton ilicifolius*", J. Chem. Soc. Perkin Trans.1, 1992, p. 3095-3098.
V. A. Kireev, Course of Physical Chemistry, Moscow, Goskhimizdat, 1956, p. 169.
N. I. Gelperin, Basic Processes and Apparatuses of Chemical Engineering, Moscow, Khimiya, 1981, Book 2, p. 679.
U.S. Appl. No. 11/406,262, filed Apr. 19, 2006, Mori.
U.S. Appl. No. 11/627,700, filed Jan. 26, 2007, Amino, et al.
U.S. Appl. No. 11/505,997, filed Aug. 18, 2006, Mori, et al.
U.S. Appl. No. 12/613,839, filed Nov. 6, 2009, Sugiyama, et al.
105,696, filed Jun. 25, 2009, Kawahara, et al.
U.S. Appl. No. 12/613,713, filed Nov. 6, 2009, Kawahara, et al.
U.S. Appl. No. 12/108,889, filed Apr. 24, 2008, Sugiyama, et al.

* cited by examiner

*Primary Examiner*—Rei-tsang Shiao
(74) *Attorney, Agent, or Firm*—Oblon, Spivak, McClelland, Maier & Neustadt, L.L.P.

(57) ABSTRACT

The present invention provides salt crystals of non-natural stereoisomer forms of monatin and to the use thereof.

75 Claims, 51 Drawing Sheets

CRYSTALS OF NON-NATURAL-TYPE STEREOISOMER SALT OF MONATIN AND USE THEREOF

CROSS-REFERENCE TO RELATED APPLICATIONS

The present application is a continuation of International Application No. PCT/JP02/12472, filed on Nov. 29, 2002, which claims priority to Japanese Application No. JP 2001-366053, filed on Nov. 30, 2001, and Japanese Application No. JP 2002-182032, filed on Jun. 21, 2002. The contents of each of these applications are hereby incorporated by reference in their entirety.

BACKGROUND OF THE INVENTION

1. Field of the Invention

The present invention provides salt crystals of non-natural stereoisomer forms of monatin and to the use thereof. More particularly, the present invention relates to salt crystals of non-natural stereoisomers of naturally occurring monatin (a (2S,4S) substance), which has excellent sweetening properties.

2. Discussion of the Background

As a result of modern eating habits, obesity arising from excessive ingestion of sugars and various diseases accompanied thereby have become a problem of medical and social importance. Accordingly, there has been a strong demand for the development of a low-calorie sweetener to replace sugar. In addition to the intensity of sweet taste, the sweetener demanded is requested to have many characteristics and essential features such as low calorie, safety, stability to heat and acid, quality of sweet taste, cost, etc.

At present, various kinds of sweeteners are used or proposed. For example, aspartame has been widely used as a sweetener due to its strong intensity of sweet taste (degree of sweet taste) and ease of mass-production. Of equal importance, aspartame also a proven safety record. Studies for derivatives of aspartame have been intensively performed.

In addition to the aspartame derivatives, sweet taste substances having various characteristics have been proposed as sweeteners and investigation for practical use has been conducted. Further, thaumatin, glycyrrhizin, stevioside, etc. derived from plants that are present in nature and able to be collected in large quantities are now used as natural sweeteners. Under such circumstances, there has been a demand for developing a sweet taste substance for practical use as a sweetener and having a strong degree of sweet taste.

Monatin is a naturally occurring amino acid derivative isolated from the bark of the roots of *Schlerochiton ilicifolius*, which is a plant naturally grown in the area of the north western Transvaal of South Africa. The structure of monatin was reported to be (2S,4S)-2-amino-4-carboxy-4-hydroxy-5-(3-indolyl)-pentanoic acid ((2S,4S)-4-hydroxy-4-(3-indolyl-methyl)-glutamic acid; refer to the structural formula (1)) by R. Vleggaar, et al. (cf. R. Vleggaar, et al., J. Chem. Soc. Perkin Trans., 3095-3098 (1992)).

According to Vleggaar, et al, intensity of the sweet taste of a (2S,4S) substance (natural-type monatin) derived from the natural plant is reported to be 800- to 1400-fold greater than that of sucrose. Although various methods have been reported as a synthetic method for producing monatin, many of these relate to synthetic methods for a mixture of stereoisomers and there has been nearly no report where each of four stereoisomers having the same chemical structural formulae as the natural-type monatin is synthesized and isolated as a pure substance and properties thereof are investigated in detail. (With regard to examples of synthesis thereof, P. J. van Wyk, et al., ZA 87/4288, ZA 88/4220; Holzapfel, et al., Synthetic Communications, 24(22), 3197-3211 (1994); E. Abushanab, et al., U.S. Pat. No. 5,994,559 (1999); K. Nakamura, et al., Organic Letters, 2, 2967-2970 (2000), etc. may be referred to.)

P. J. van Wyk, et al (GB 2 205 834)) first disclosed monatin. Although the inventors determined by means of an X-ray crystal structure analysis that a stereoisomer present in nature and having a strong sweet taste is a (2S,4S) substance or a (2R,4R) substance, they reported that, by combining with the result of synthesis of a mixture of a (2S,4S) substance and a (2S,4R) substance from (2S)-aspartic acid, there is a high probability that a stereoisomer present in nature and having a strong sweet taste is a (2S,4S) substance. Then, in accordance with the above-mentioned document by R. Vleggaar, et al., a stereoisomer (steric structure) of monatin is reported as being present in natural plant is a (2S,4S) substance, only, and that its intensity of sweet taste is 800- to 1400-fold of sucrose. On the basis of this information, it is proper to conclude that a stereoisomer (steric structure) of monatin which is present in nature and is a substantial body of a strong sweet taste is a (2S,4S) substance.

In K. Nakamura, et al., they isolated hydrochlorides of a (2S,4S) monatin substance and of a (2S,4R) monatin substance. They reported that, with regard to the intensity of sweet taste thereof, the synthetic (2S,4S) monatin substance exhibited a sweet potency equivalent to that of the a natural specimen of monatin (a (2S,4S) substance) and the synthetic (2S,4R) monatin substance exhibited a slightly sweet taste presumably due to monatin (a (2S,4S) substance), which is thought to be present as an impurity, although the specific intensity of the sweet taste was not reported. Thus, although this document is the first example referring to the intensity of the sweet taste of a non-natural-type stereoisomer (other than a (2S,4S) substance) of monatin, it is reported that hydrochloride of a (2S,4R) monatin substance has almost no sweet taste.

On the other hand, T. Kitahara, et al. report a selective synthetic method for each stereoisomer of monatin as a sweetener (sweetening agent) but do not report the degree of sweet taste of each stereoisomer (refer to T. Kitahara, et al., Abstracts of Papers Presented at the General Meeting in 2000 of the Agricultural Chemical Society of Japan, 3B128β (page 221)).

When the information as mentioned above is taken into consideration as a whole, the followings have been noted.

(1) A stereoisomer (steric structure) of monatin that is present in nature and has an intensity of sweet taste of as strong as 800- to 1400-fold is a (2S,4S) substance; and (2) With regard to other non-natural-type stereoisomers of monatin, although there are examples where they are isolated in small quantities, there is no example where the pure substance is isolated, purified, and the intensity of the sweetness assessed.

Thus, heretofore, there have been no clear data for the intensity of sweet taste of each stereoisomer of monatin in practical concentrations corresponding to 5 to 10% sucrose concentrations except the monatin form that is obtained from nature (a (2S,4S) substance). Accordingly, it is not possible to know from the prior art whether non-natural stereoisomers of monatin except monatin (a (2S,4S) substance) are useful as a sweetener. In other words, reliable information for the degree of sweet taste (intensity of sweet taste) except monatin derived from nature (a (2S,4S) substance) is little and, when the prior art is considered as a whole, the present situation is nothing but to conclude that non-natural-type monatin stereoisomers except monatin (a (2S,4S) substance) have low degree of sweet taste and are unable to be expected for their utility as sweeteners.

One of the causes therefor is that, until now, there has been found no method whereby each of the above-mentioned stereoisomers may be synthesized, isolated and purified.

Accordingly, there exists a demand for at least several hundred milligrams or more of the naturally occurring monatin, as well as the three non-natural stereoisomers thereof. More specifically, there exists a demand for isolated and purified forms of the same for assessment of the optical purity and intensity of sweetness thereof. Thereby the utility of monatin (a (2S,4S) substance) and stereoisomers thereof (i.e., non-natural-type stereoisomers) as sweeteners may be assessed and ultimately a sweetener containing a component having a high utility may be developed.

With regard to a method of separation of each stereoisomer in a high purity, there will be firstly a crystallizing method. Therefore, some explanations will be made for crystals of monatin (including the forms of free compounds, salts, etc.) as follows.

The state of the prior art is summarized as follows. R. Vleggaar, et al. report that crystals of a free compound of monatin (a (2S,4S) substance) are prepared from a mixed solvent of water, acetic acid and ethanol (1:1:5) and its melting point is described as 216-220° C. P. J. van Wyk, et al., disclosed a melting point of a free compound (crystalline solid) of monatin (a (2S,4S) substance) is described as 247-265° C. (decomposition) while, with regard to various salts, they are reported to be amorphous solids. In C. W. Holzapfel, et al., crystals of a free compound of a mixture of a (2S,4S) substance and a (2R,4R) substance of synthetic monatin are prepared by crystallization for two times from a mixed solvent of water and acetic acid (10:1) and the melting point is reported to be 212-214° C.

Accordingly, with regard to non-natural stereoisomers of monatin and a mixture of such a plurality of stereoisomers except the above two examples such as a free compound of a (2S,4S) monatin substance, not only free compound but also various salts have not been isolated in a crystalline state whereby their physical property data and other information have not been known at all.

Thus, a crystallizing method does not exist at present. Such a method would be the simplest and most effective method for purification as compared with conventional purifying methods such as ion-exchange chromatography and also for crystals prepared thereby except the two cases of a free compound of monatin (a (2S,4S) substance) and a mixture of free compounds of (2S,4S) substance and (2R,4R) monatin substance. At present no knowledge exists at all for crystals of salts. Accordingly, in view of a practical application of various stereoisomers of monatin as sweeteners, there exists a critical demand for these salt forms.

SUMMARY OF THE INVENTION

It is an object of the present invention to provide a sweetening agent based on the non-naturally occurring stereoisomer salts of monatin.

In an object of the present invention is an isolated crystalline form of the non-naturally occurring stereoisomer salts of monatin (i.e., a (2S,4R) monatin substance, a (2R,4R) monatin substance, and a (2R,4S) monatin substance).

Further, it is an object of the present invention that the isolated crystalline form has a chemical purity of at least 95% and/or an optical purity of at least 94%.

In another object of the present invention is an isolated mixed crystal containing at least two isomers, in a salt form, selected from a (2S,4R) monatin substance, a (2R,4R) monatin substance, a (2R,4S) monatin substance, and a (2S,4S) monatin substance.

In yet another object of the present invention is a composition containing at least one crystalline form of monatin selected from the group consisting of a (2S,4R) monatin substance, a (2R,4R) monatin substance, and a (2R,4S) monatin substance.

In still another object of the present invention are sweeteners, beverages, and/or foods containing the isolated crystalline form of the non-naturally occurring stereoisomer salts of monatin, the isolated mixed crystal, or the composition (above), as well as methods of making the same.

Another object of the present invention is a method of producing a crystalline form of monatin, by (a) synthesizing a racemic mixture of monatin, (b) separating the stereoisomers of monatin contained in said racemic mixture by HPLC, (c) purifying said stereoisomers by ion-exchange chromatography, and (d) freeze-drying said stereoisomers in a salt form.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

Ordinate and abscissa show diffraction intensity and diffraction angle 2θ [deg], respectively (these assignments also apply to the ordinate and abscissa for the powder X-ray diffraction charts below).

Figure 4:
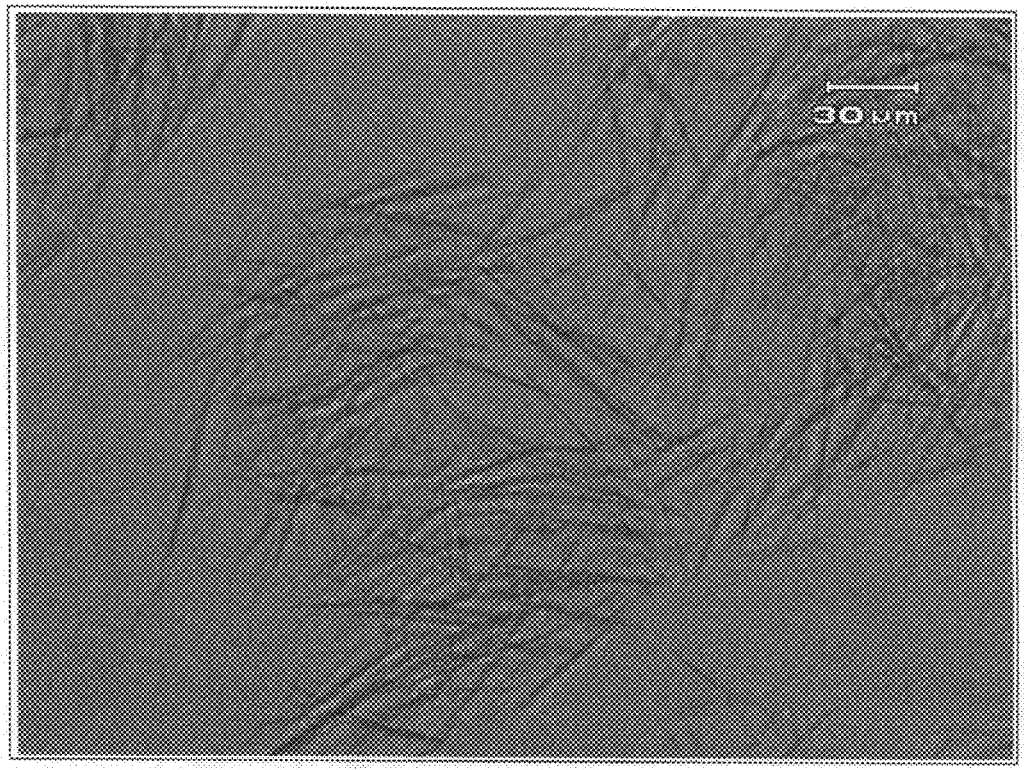

FIG. 4 shows an optical microphotograph (magnification: 200-power) immediately prior to separation of a crystallized solution of sodium salt crystals of a (2R,4R) monatin substance of Example 14.

Figure 5:
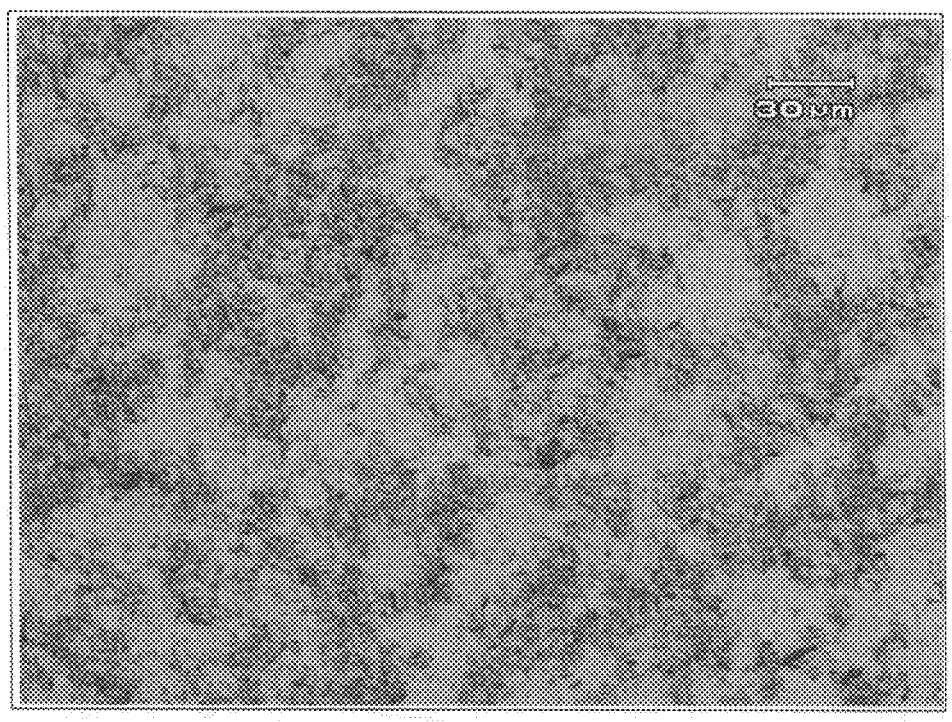

FIG. 5 shows an optical microphotograph (magnification: 200-power) after drying of the sodium salt crystals of a (2R, 4R) monatin substance of Example 14.

Figure 6:
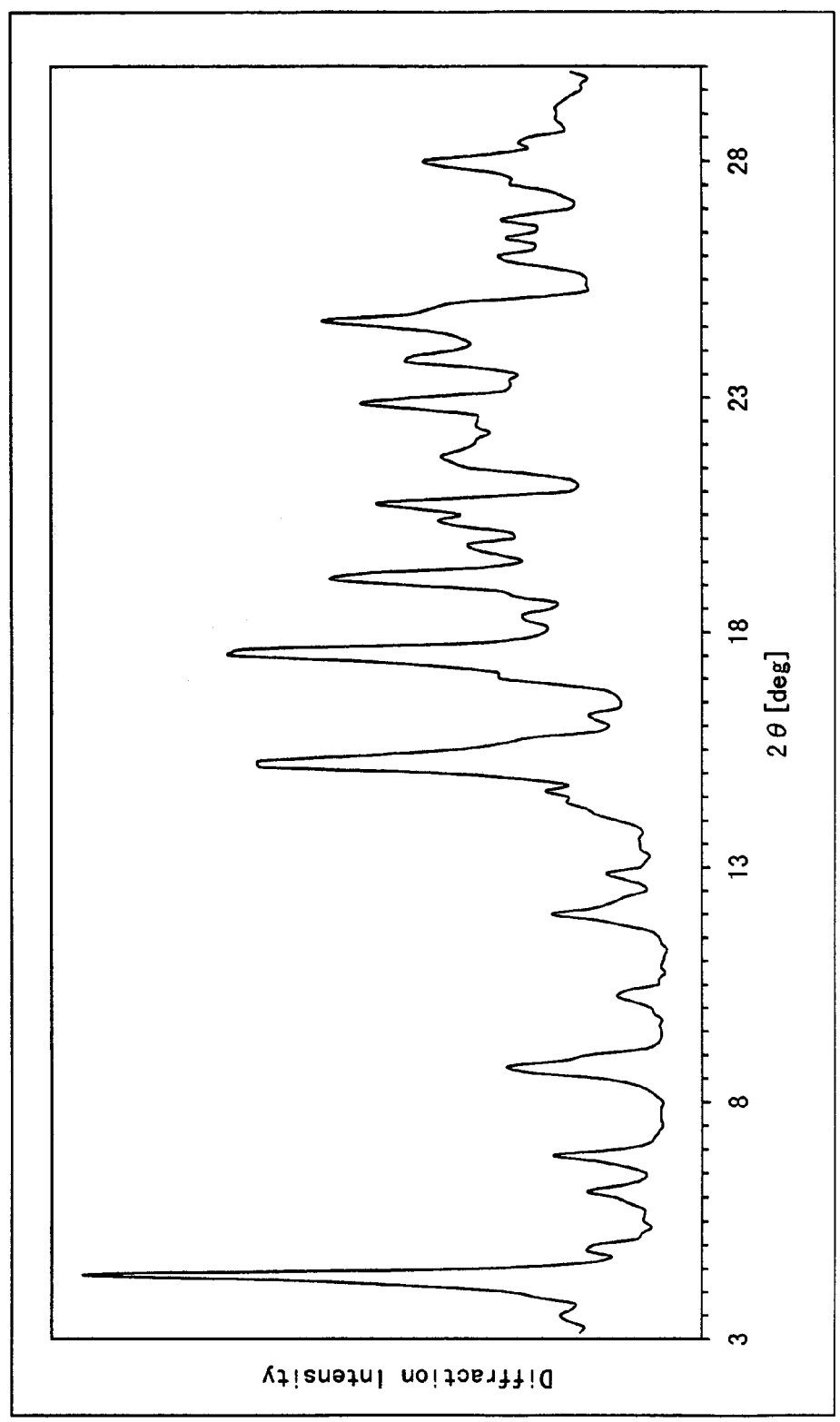

FIG. 6 is a powder X-ray diffraction chart after drying sodium salt crystals of a (2R,4R) monatin substance of Example 14.

Figure 7:
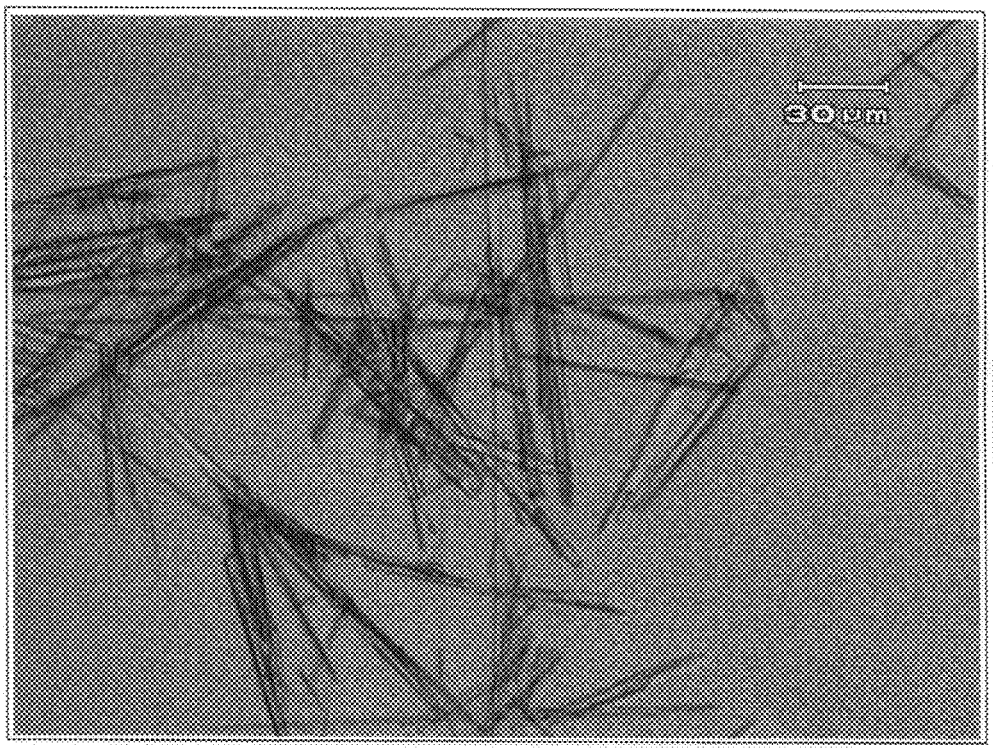

FIG. 7 shows an optical microphotograph (magnification: 200-power) immediately prior to separation of a crystallized solution of ammonium salt crystals of a (2R,4R) monatin substance of Example 15.

Figure 8:
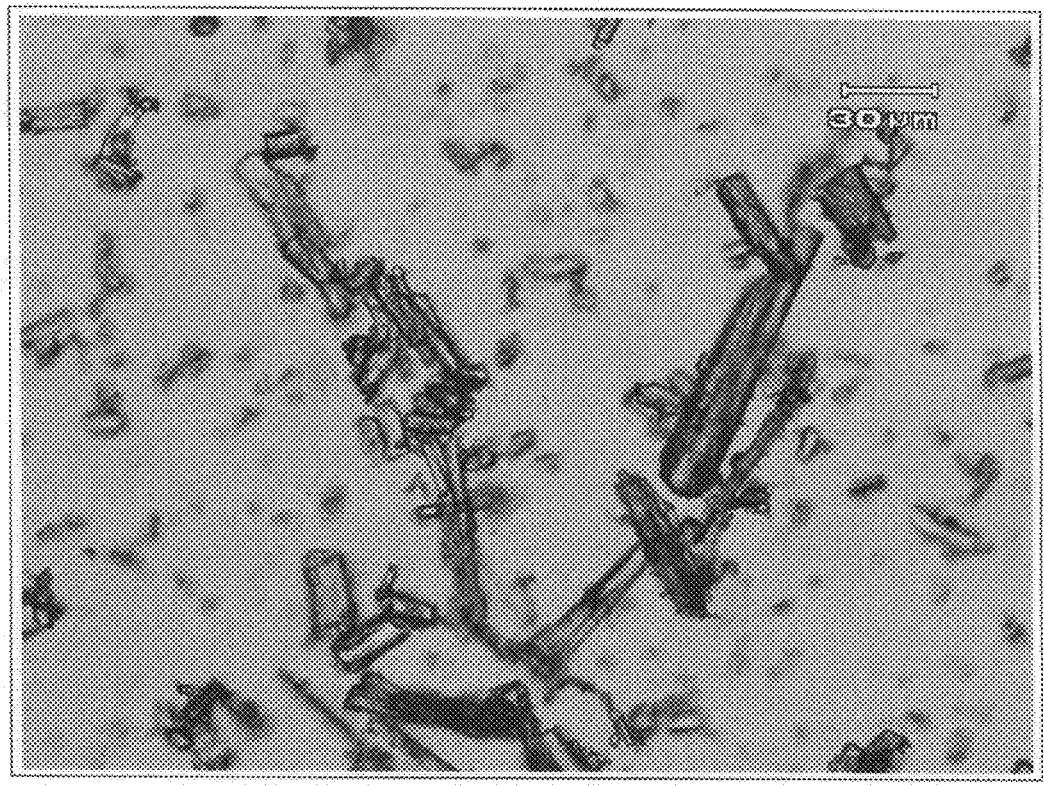

FIG. 8 shows an optical microphotograph (magnification: 200-power) after drying of ammonium salt crystals of a (2R, 4R) monatin substance of Example 15.

Figure 9:
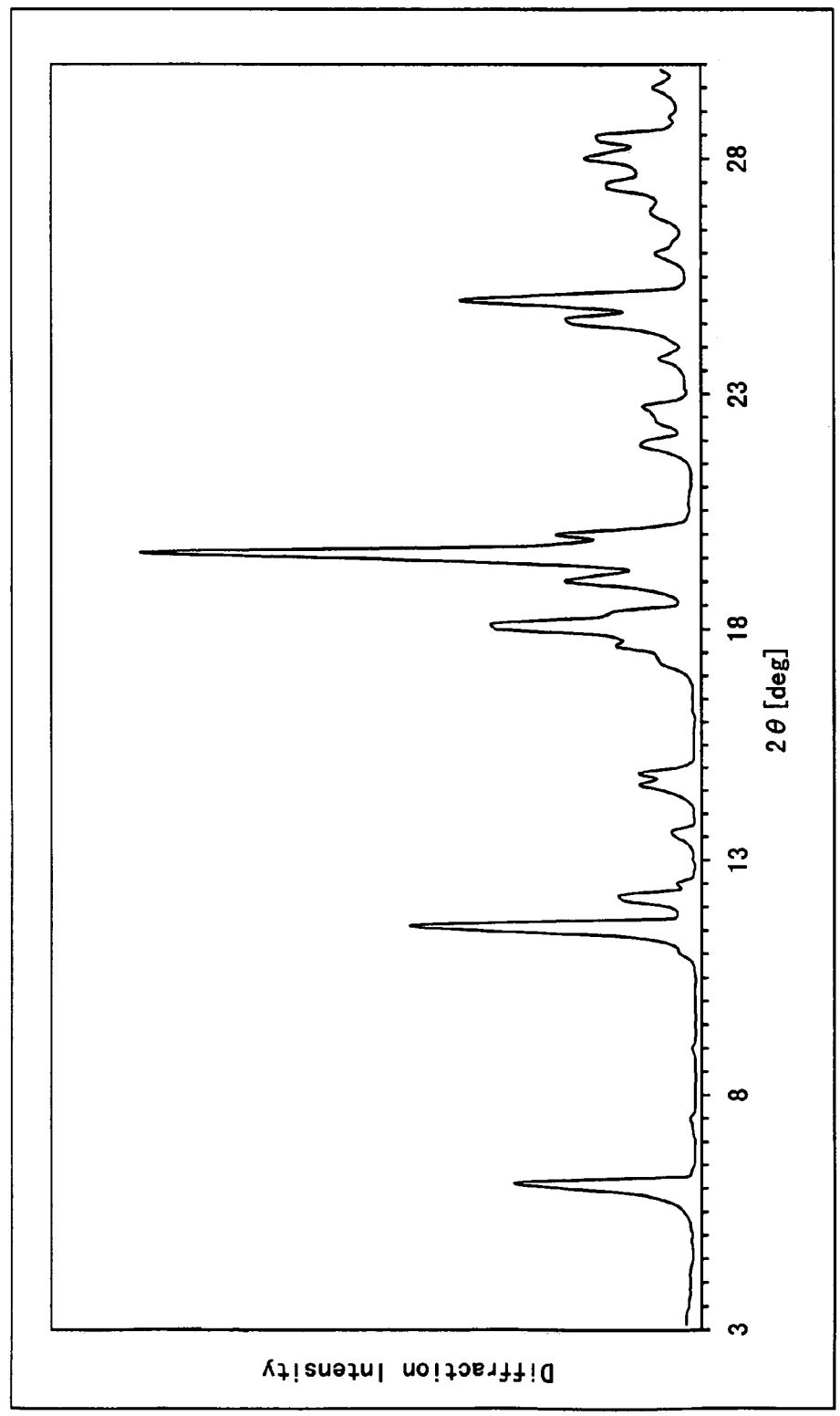

FIG. 9 is a powder X-ray diffraction chart after drying of ammonium salt crystals of a (2R,4R) monatin substance of Example 15.

Figure 10:
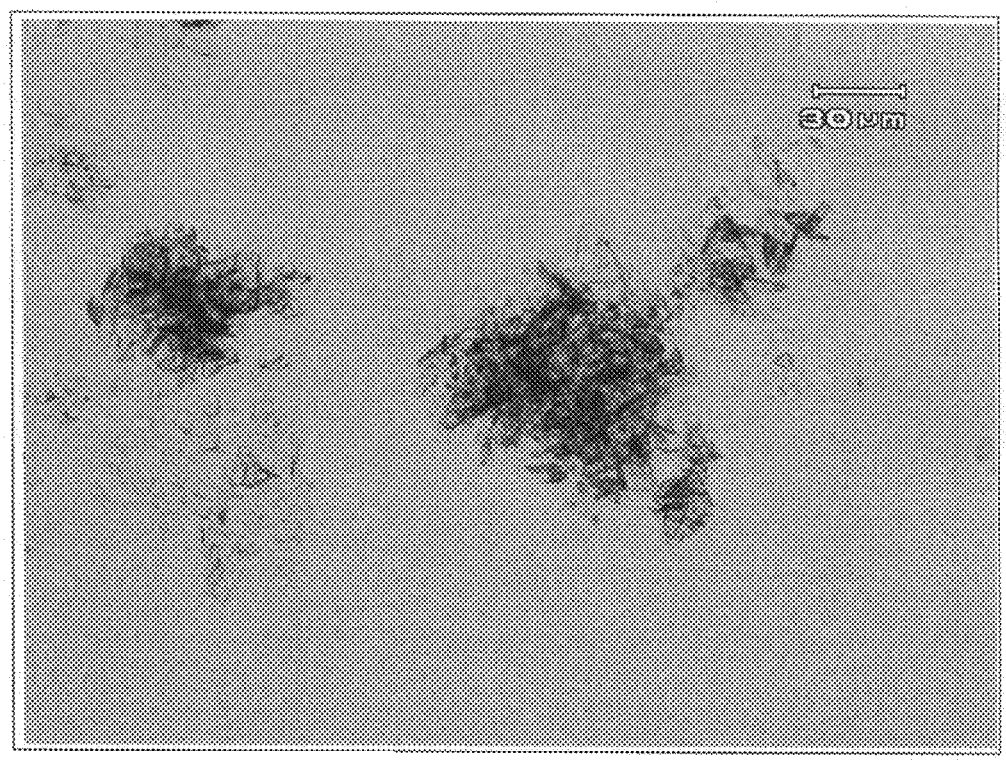

FIG. 10 shows an optical microphotograph (magnification: 200-power) immediately prior to separation of a crystallized solution of crystals of a free (2R,4R) monatin substance of Comparative Example 1.

Figure 11:
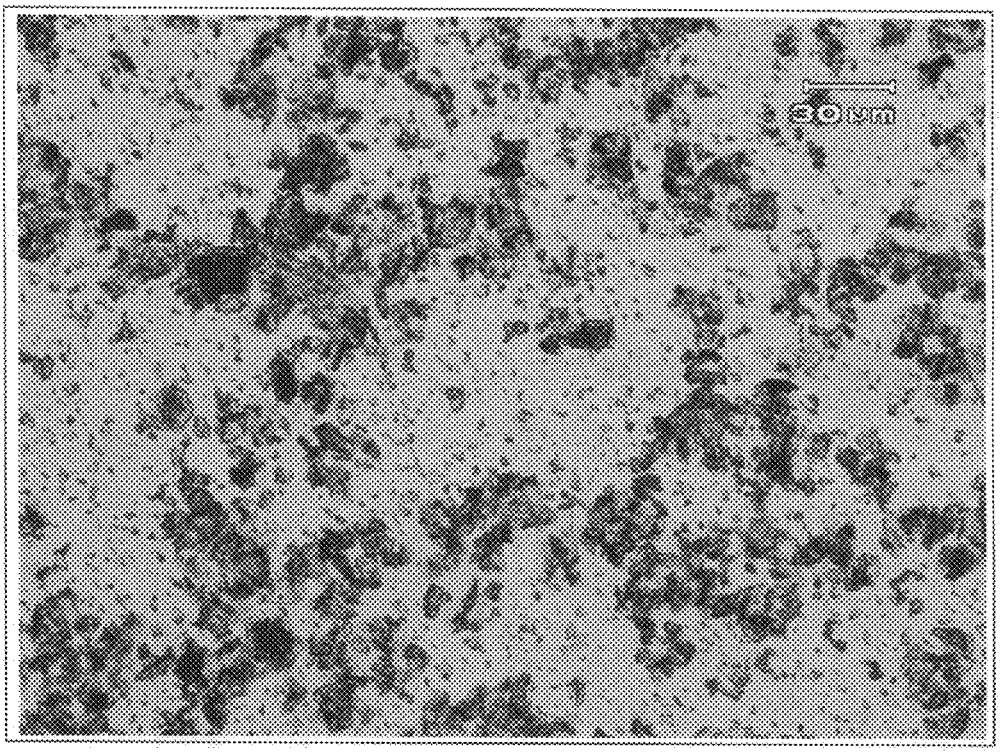

FIG. 11 shows an optical microphotograph (magnification: 200-power) after drying of crystals of a free (2R,4R) monatin substance of Comparative Example 1.

Figure 12:
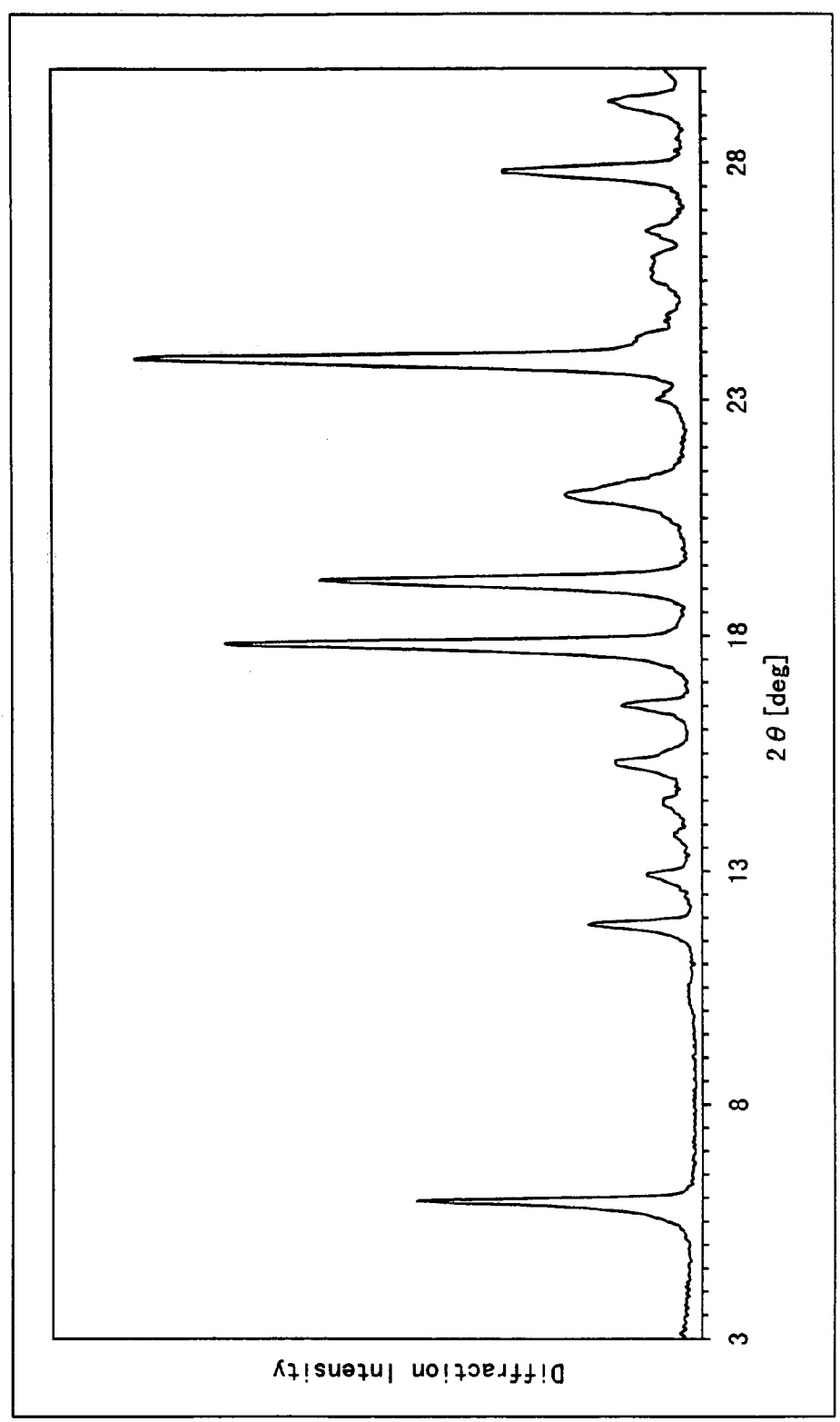

FIG. 12 is a powder X-ray diffraction chart after drying of crystals of a free (2R,4R) monatin substance of Comparative Example 1.

Figure 13:
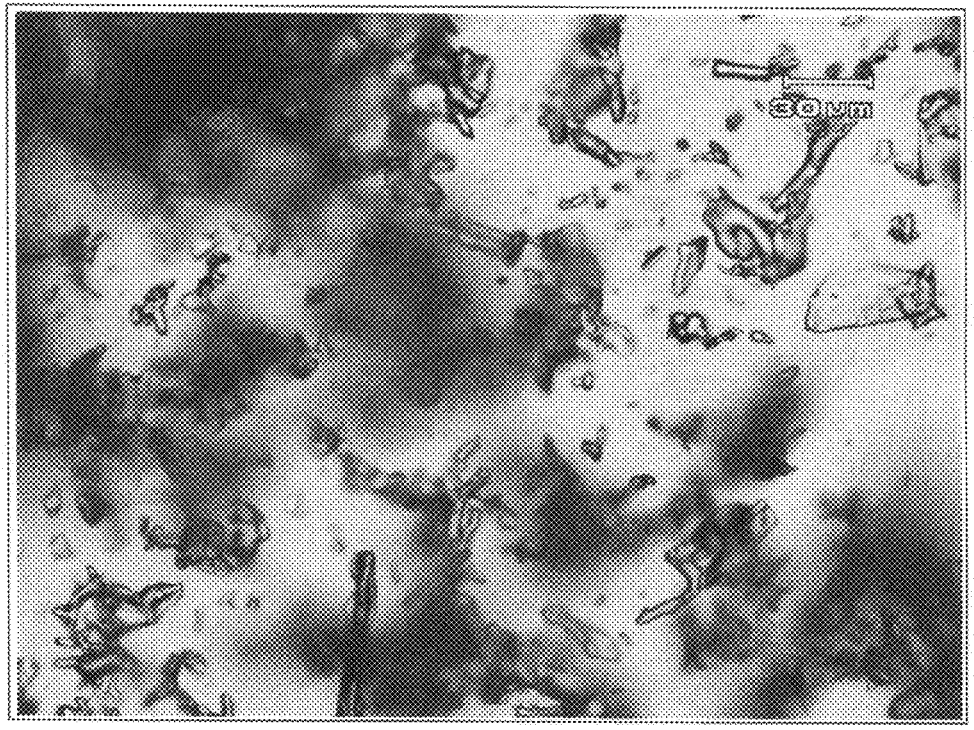

FIG. 13 shows an optical microphotograph (magnification: 200-power) after drying of an amorphous solid of potassium salt of a (2R,4R) monatin substance of Comparative Example 2.

Figure 14:
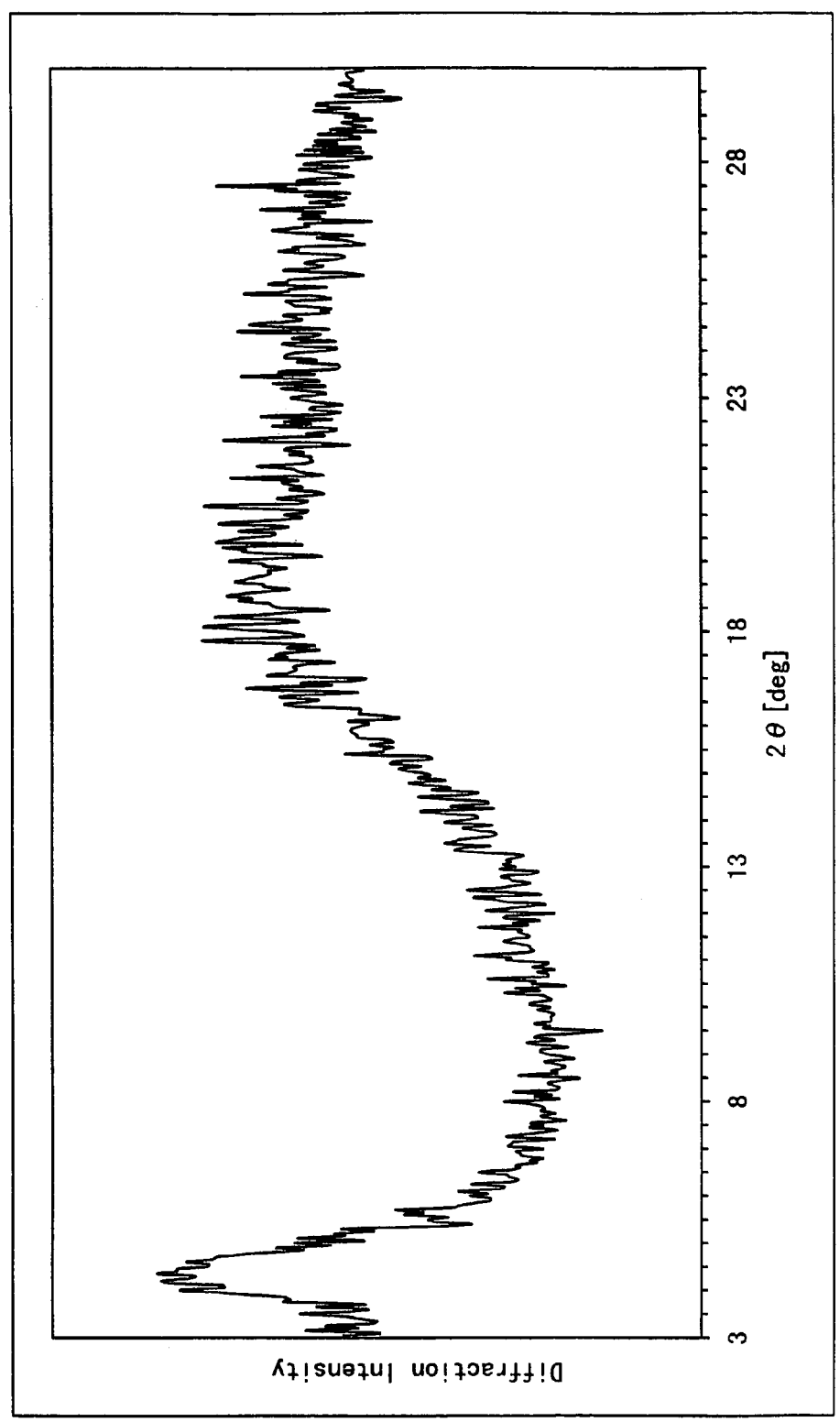

FIG. 14 is a powder X-ray diffraction chart after drying of an amorphous solid of potassium salt of a (2R,4R) monatin substance of Comparative Example 2.

Figure 15:
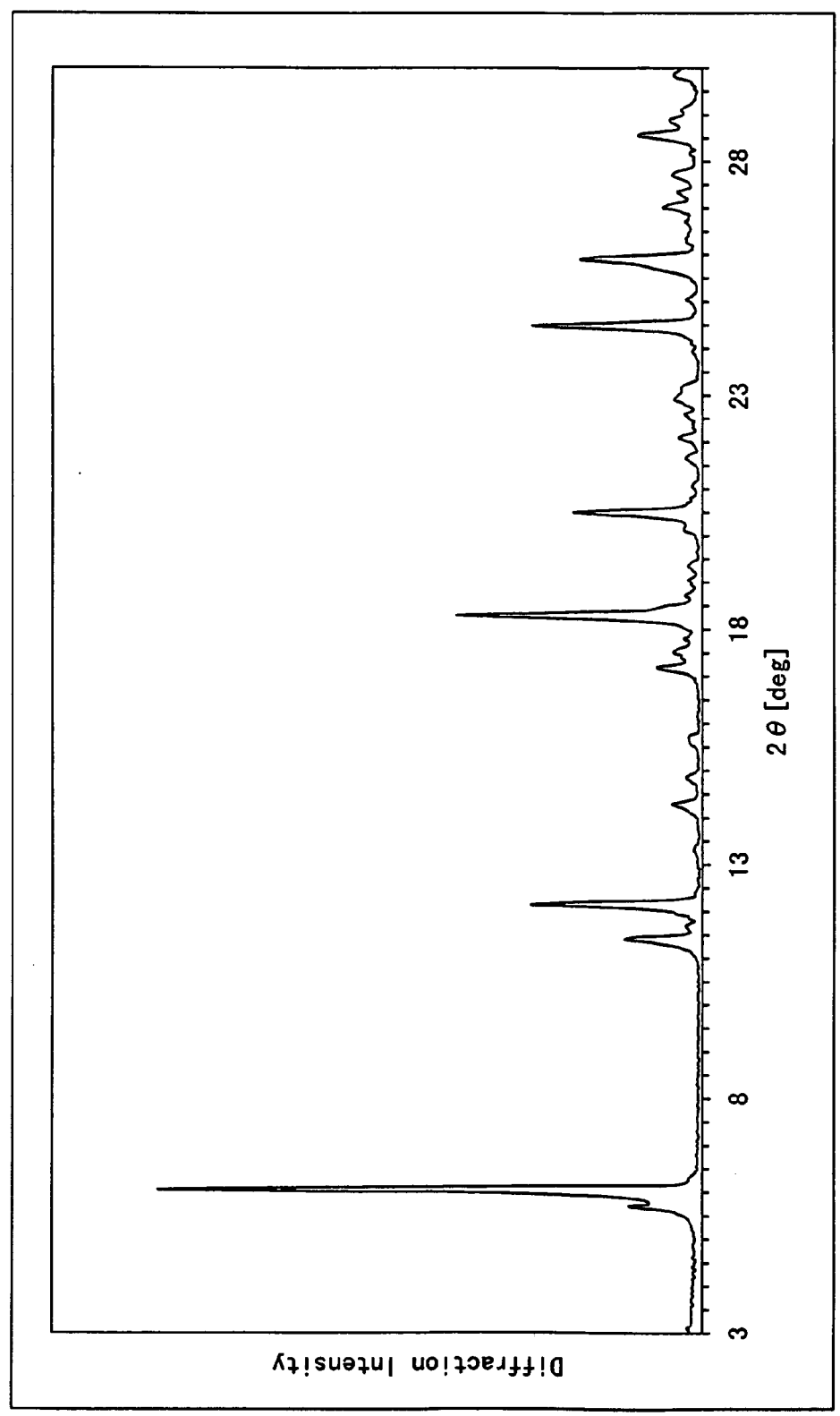

FIG. 15 is a powder X-ray diffraction chart after drying of crystals of potassium salt of a (2R,4R) monatin substance of Example 17.

Figure 16:
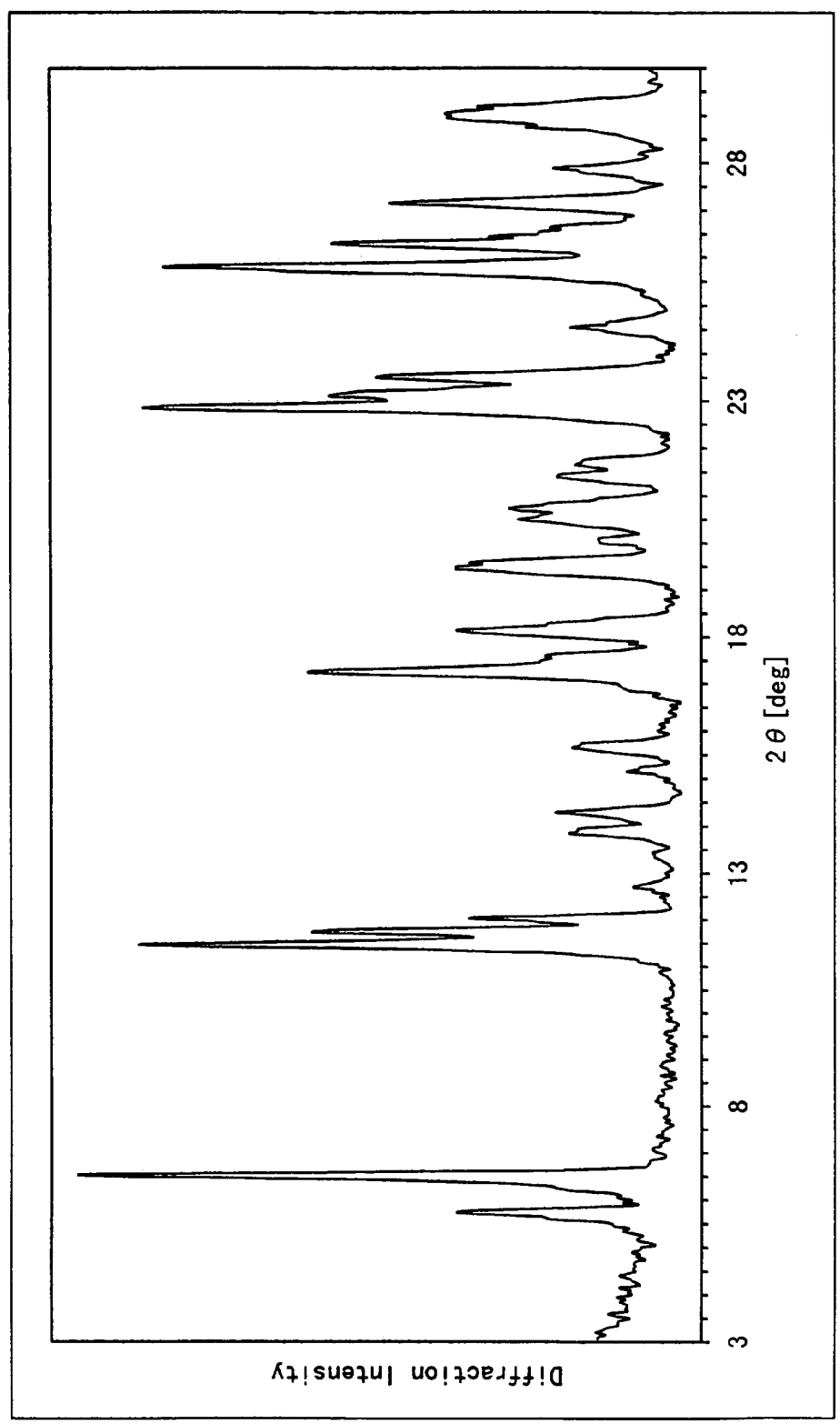

FIG. 16 is a powder X-ray diffraction chart after drying of crystals of potassium salt of a (2R,4R) monatin substance of Example 18.

Figure 17:
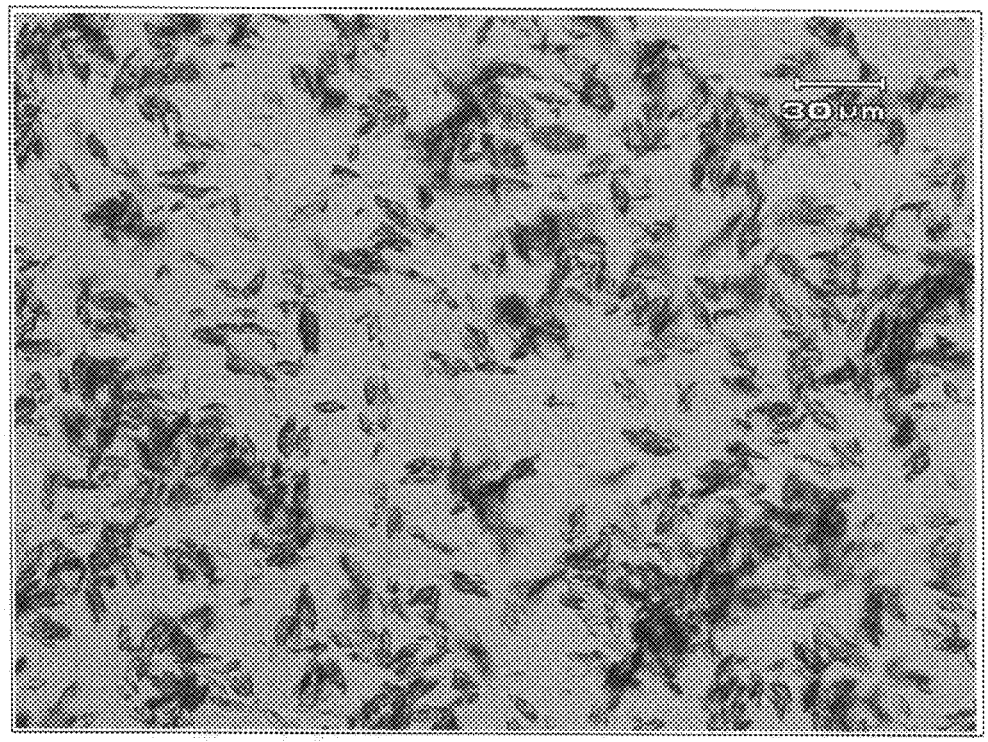

FIG. 17 shows an optical microphotograph (magnification: 200-power) after drying of ammonium salt crystals of [(2S,4S)+(2R,4R)] monatin substances of Example 2.

Figure 18:
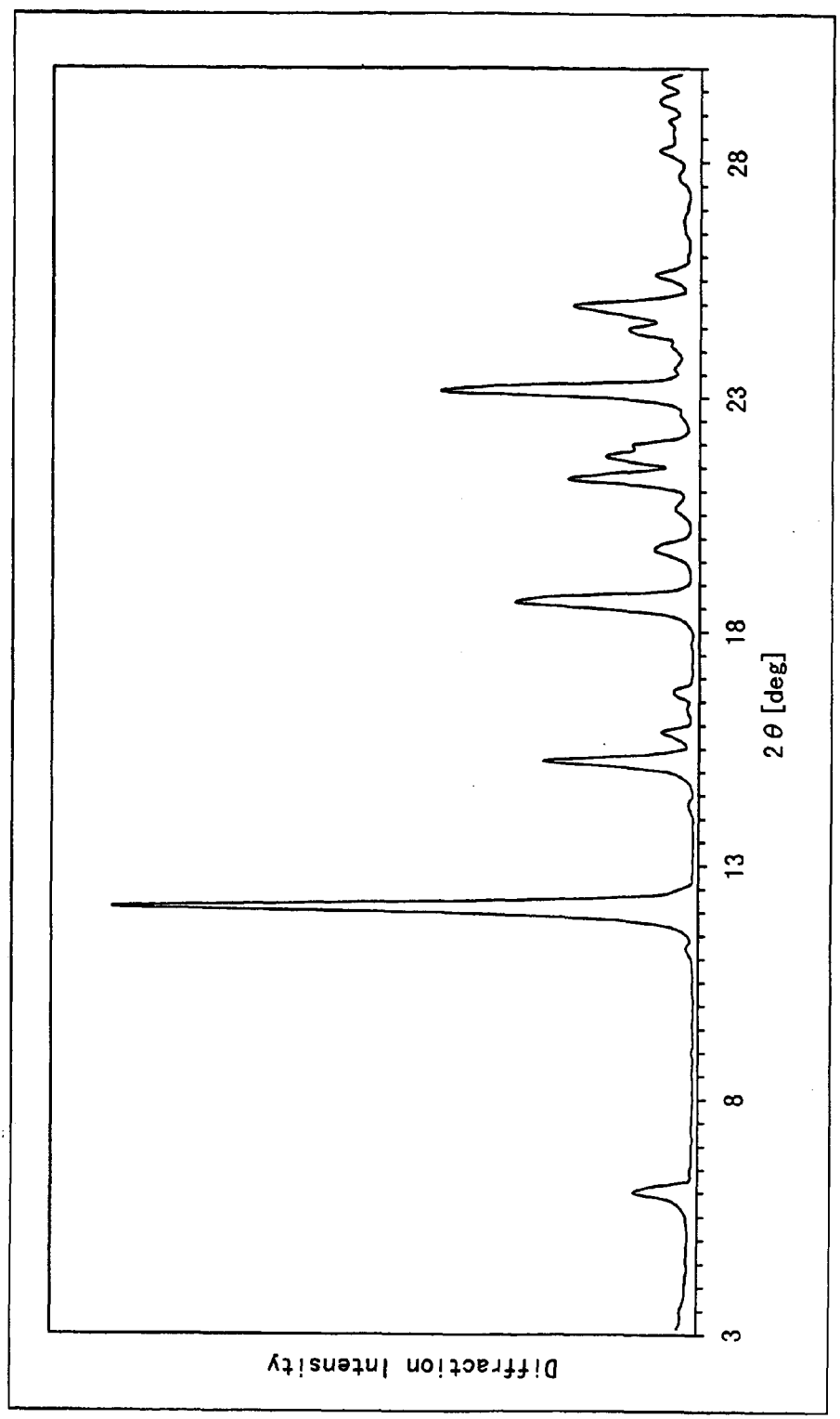

FIG. 18 is a powder X-ray diffraction chart after drying of ammonium salt crystals of [(2S,4S)+(2R,4R)] monatin substances of Example 2.

Figure 19:
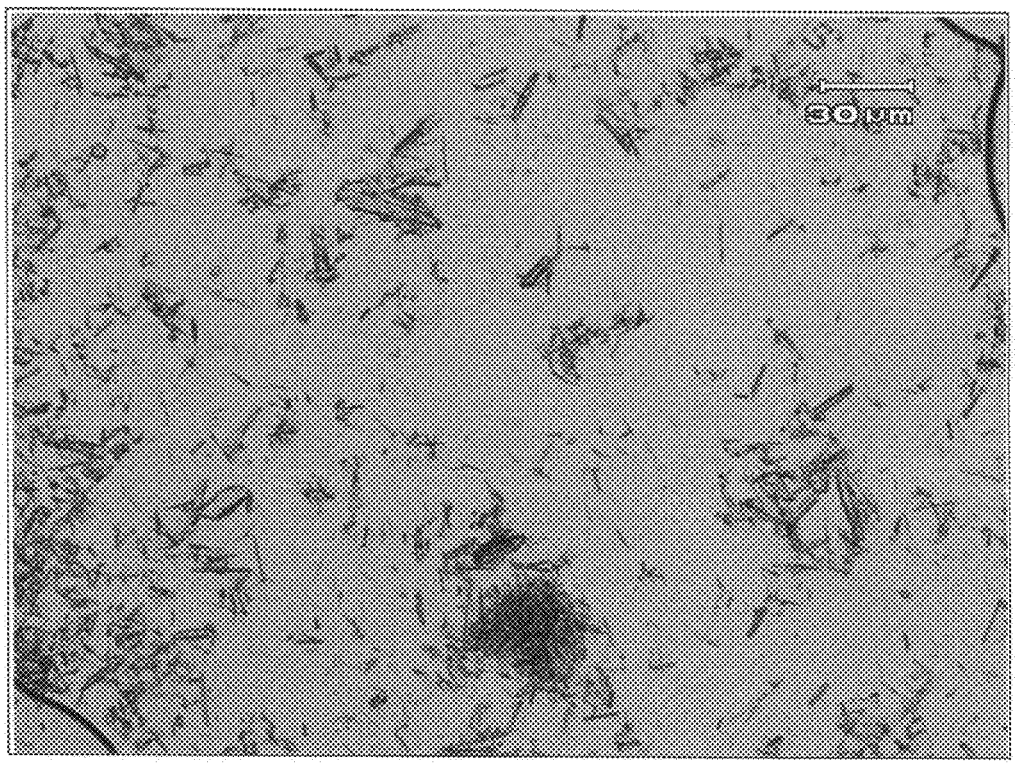

FIG. 19 shows an optical microphotograph (magnification: 200-power) after drying of ammonium salt crystals of [(2S,4R)+(2R,4S)] monatin substances of Example 2.

Figure 20:
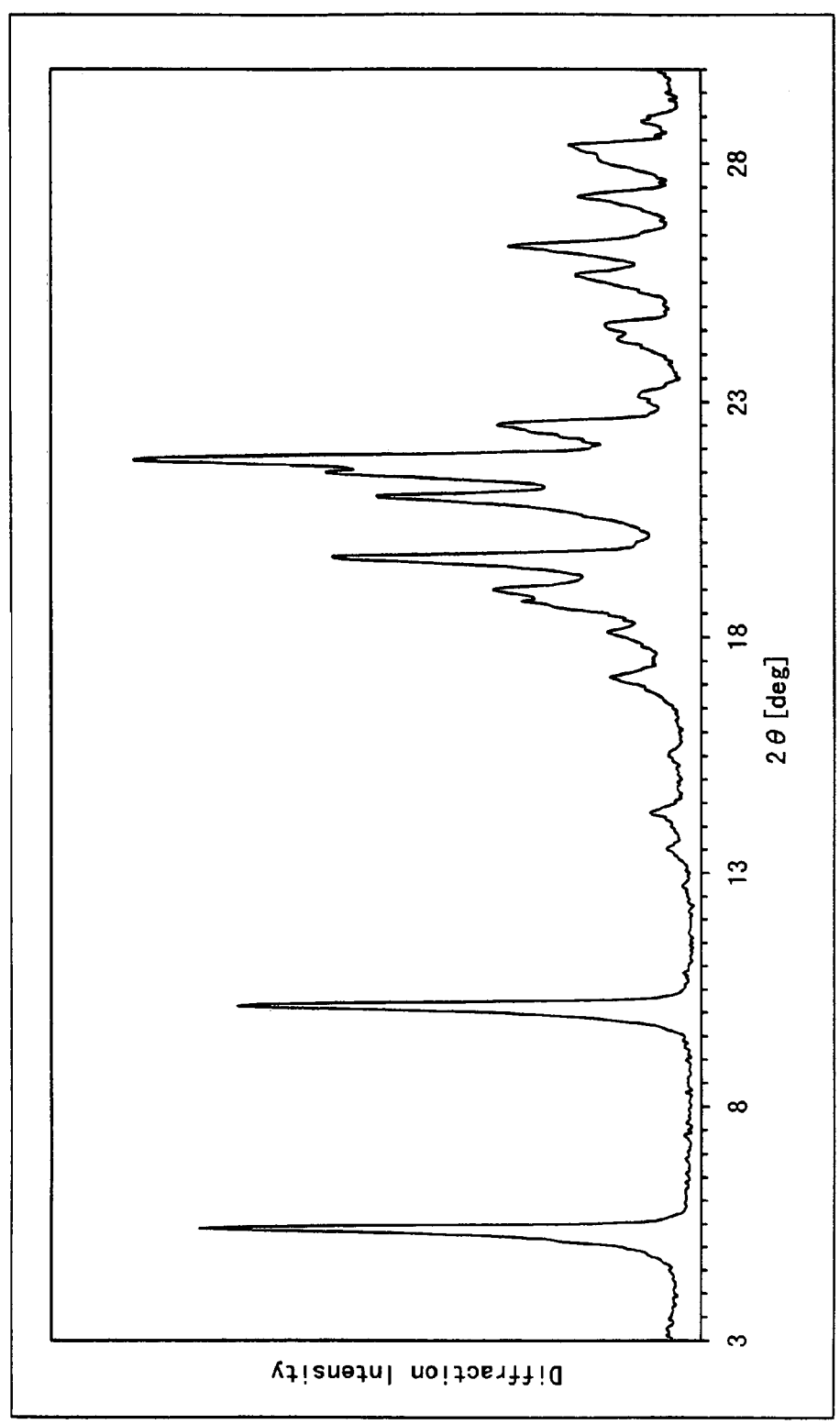

FIG. 20 is a powder X-ray diffraction chart after drying of ammonium salt crystals of [(2S,4R)+(2R,4S)] monatin substances of Example 2.

Figure 21:
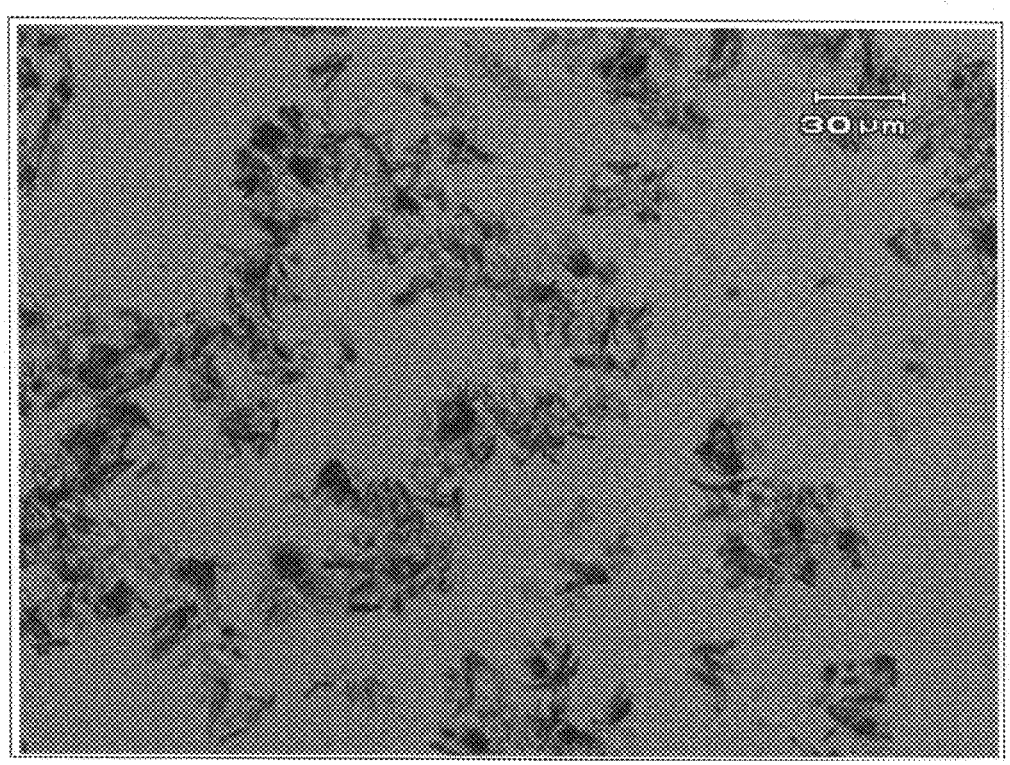

FIG. 21 shows an optical microphotograph (magnification: 200-power) after drying of sodium salt crystals of [(2S,4S)+(2R,4R)] monatin substances of Example 3.

Figure 22:
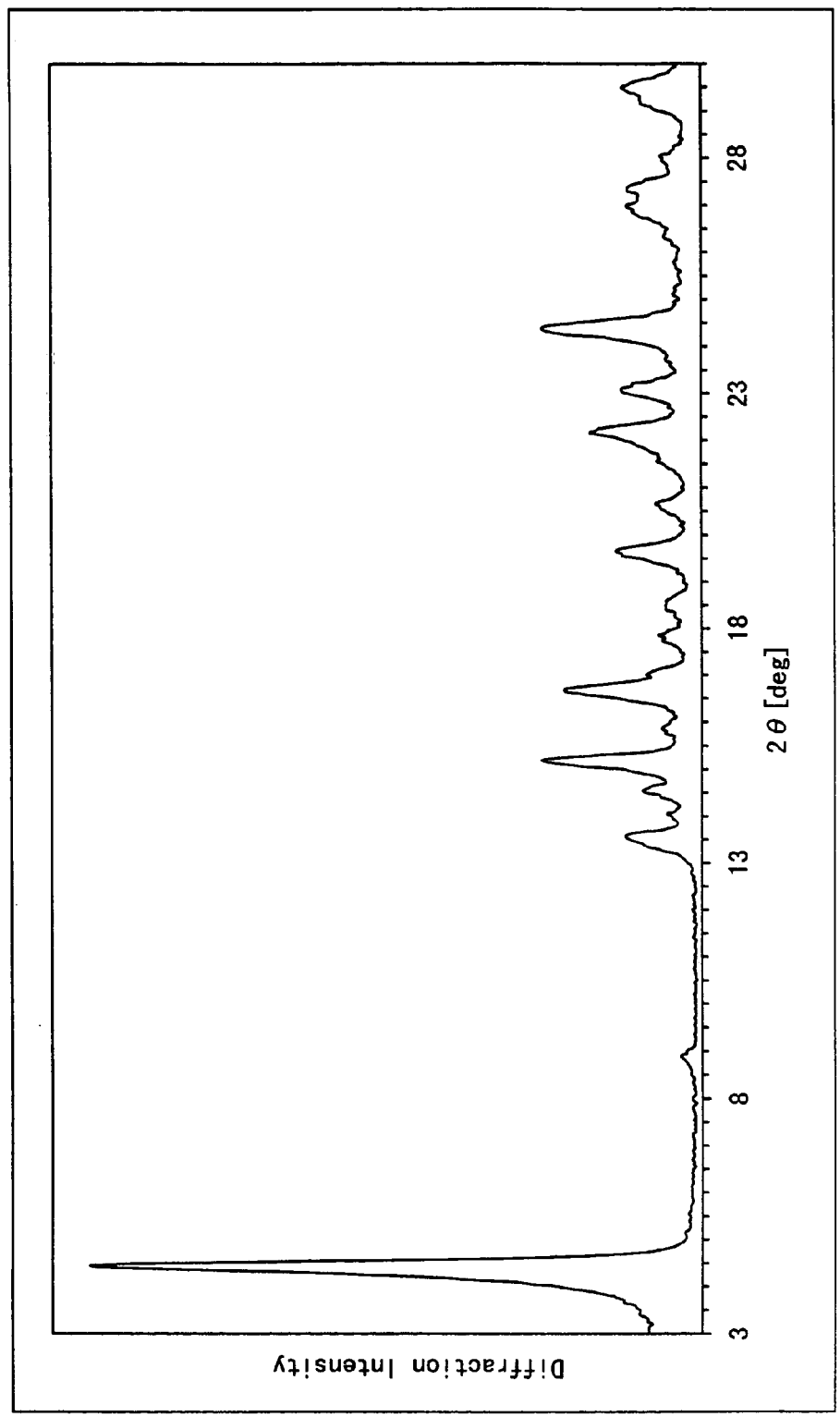

FIG. 22 is a powder X-ray diffraction chart after drying of sodium salt crystals of [(2S,4S)+(2R,4R)] monatin substances of Example 3.

Figure 23:
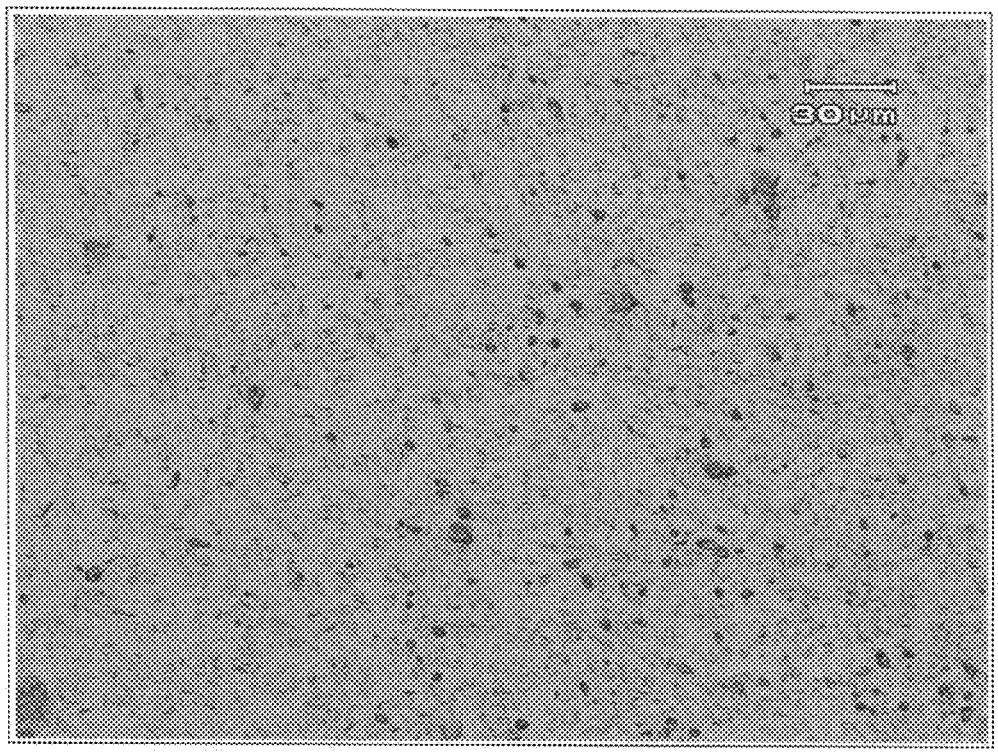

FIG. 23 shows an optical microphotograph (magnification: 200-power) after drying of potassium salt crystals of [(2S,4S)+(2R,4R)] monatin substances of Example 4.

Figure 24:
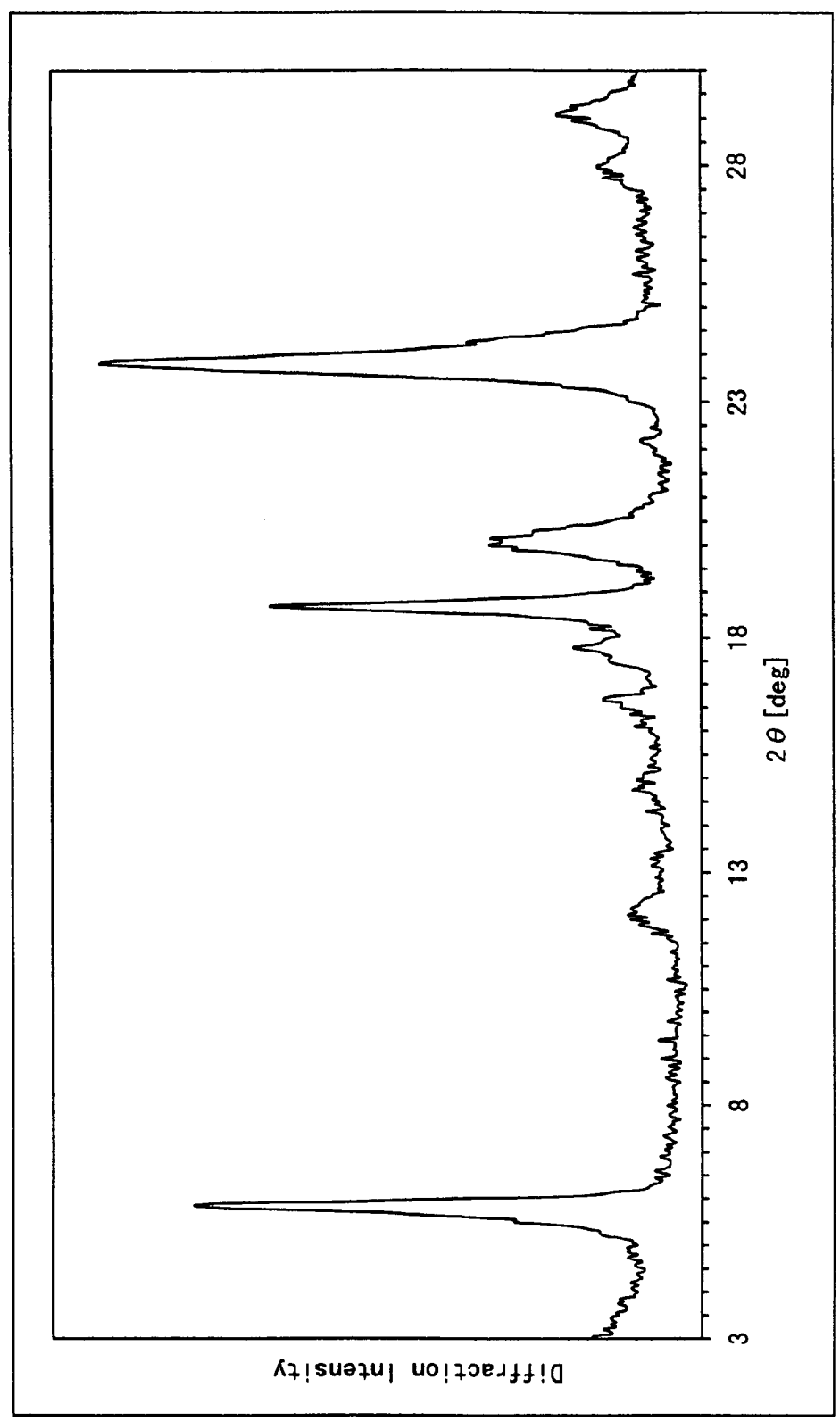

FIG. 24 is a powder X-ray diffraction chart after drying of potassium salt crystals of [(2S,4S)+(2R,4R)] monatin substances of Example 4.

Figure 25:
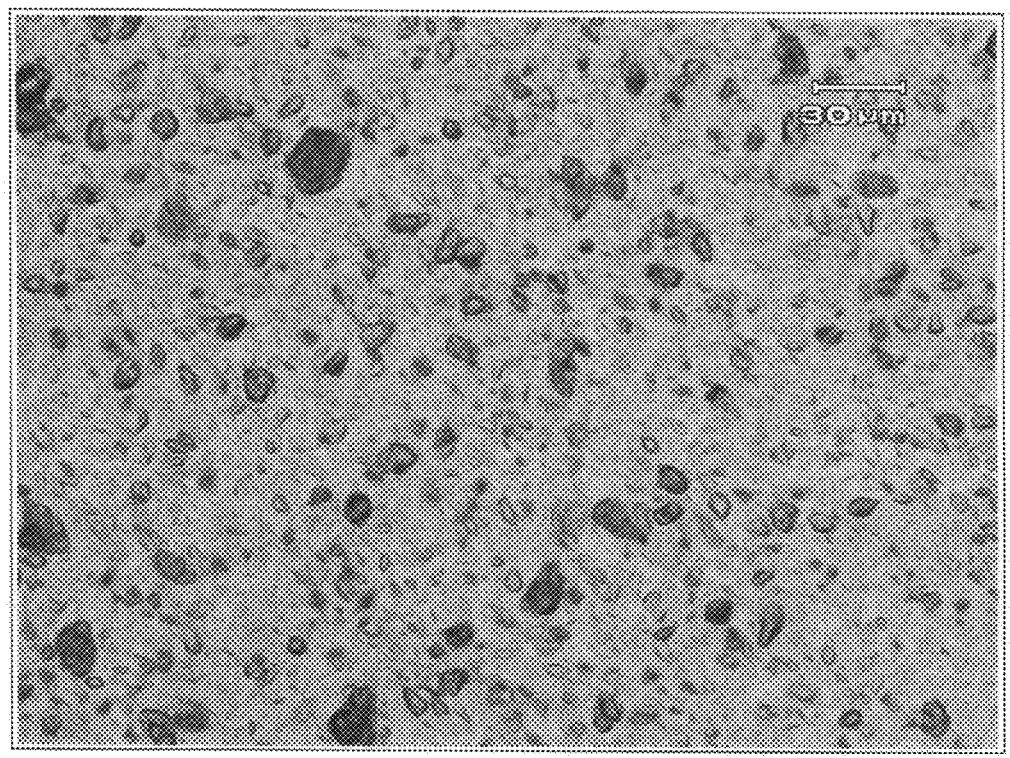

FIG. 25 shows an optical microphotograph (magnification: 200-power) after drying of sodium salt crystals of a (2R,4S) monatin substance of Example 11.

Figure 26:
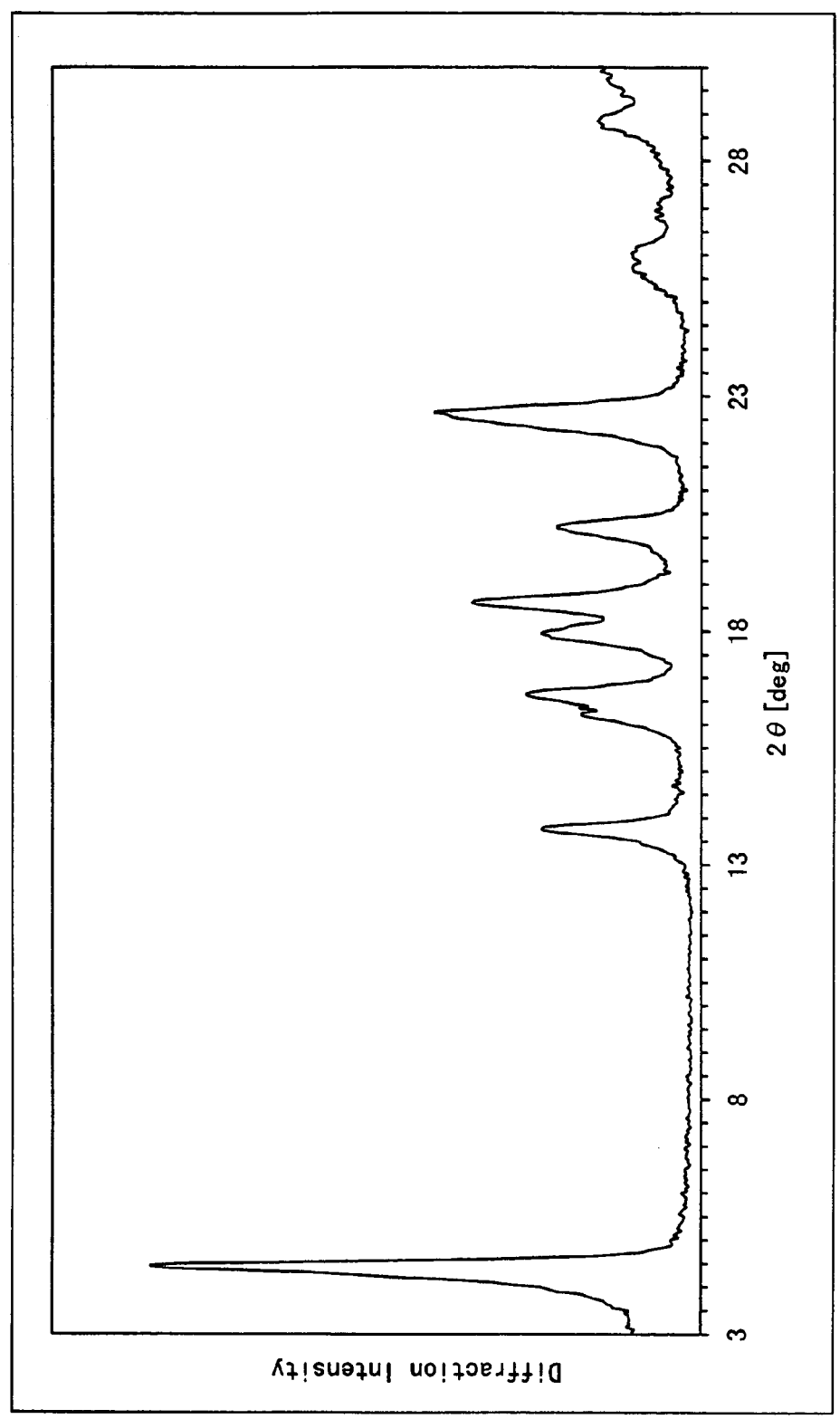

FIG. 26 is a powder X-ray diffraction chart after drying of sodium salt crystals of a (2R,4S) monatin substance of Example 11.

Figure 27:
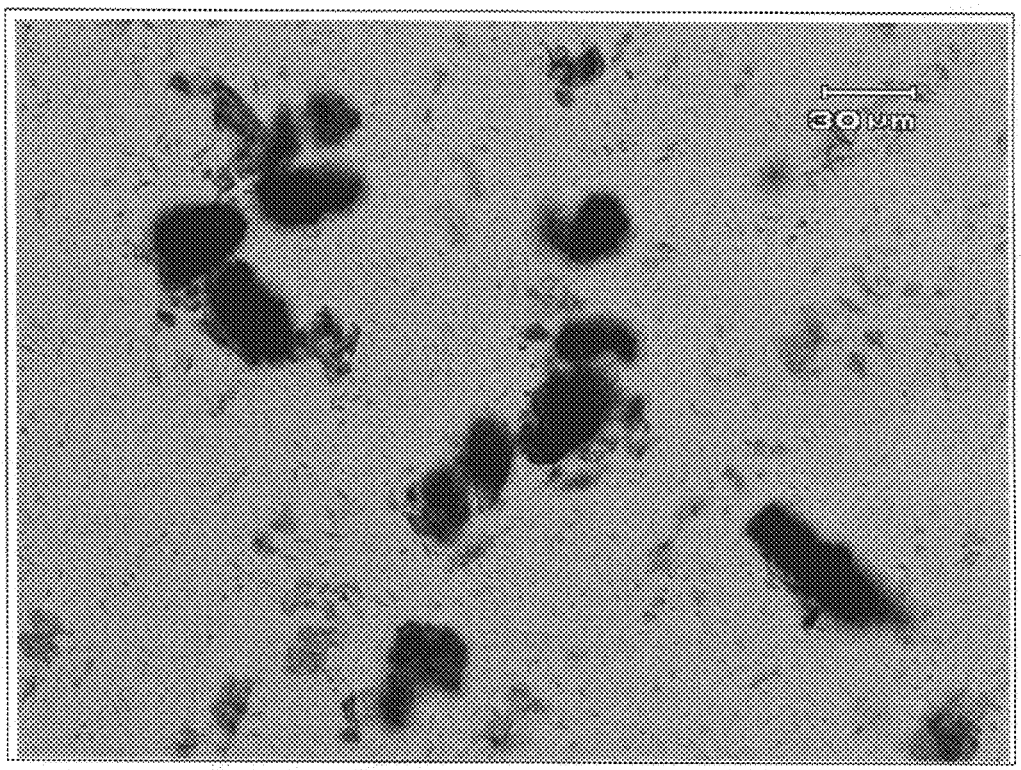

FIG. 27 shows an optical microphotograph (magnification: 200-power) after drying of sodium salt crystals of a (2S,4R) monatin substance of Example 12.

Figure 28:
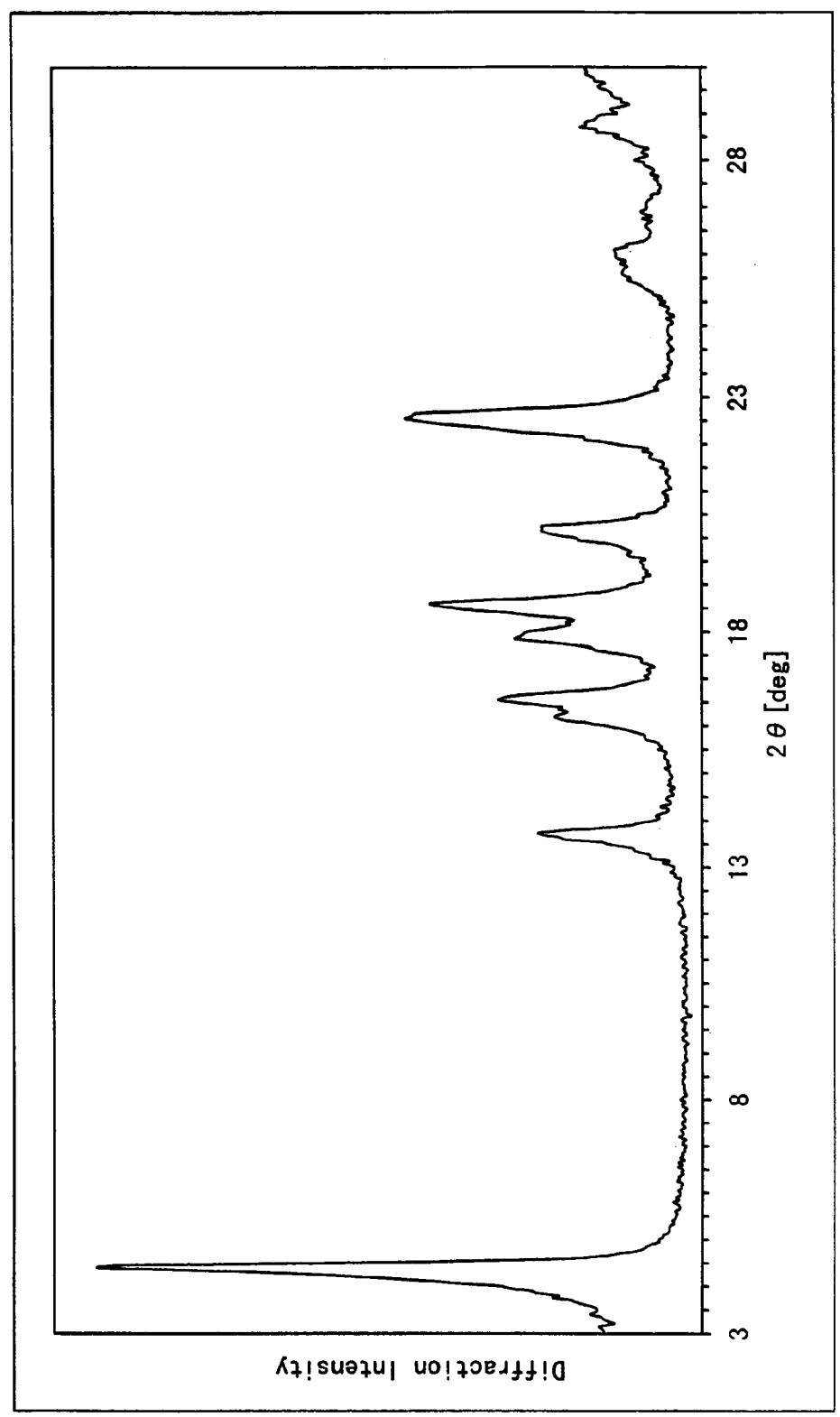

FIG. 28 is a powder X-ray diffraction chart after drying of sodium salt crystals of a (2S,4R) monatin substance of Example 12.

Figure 29:
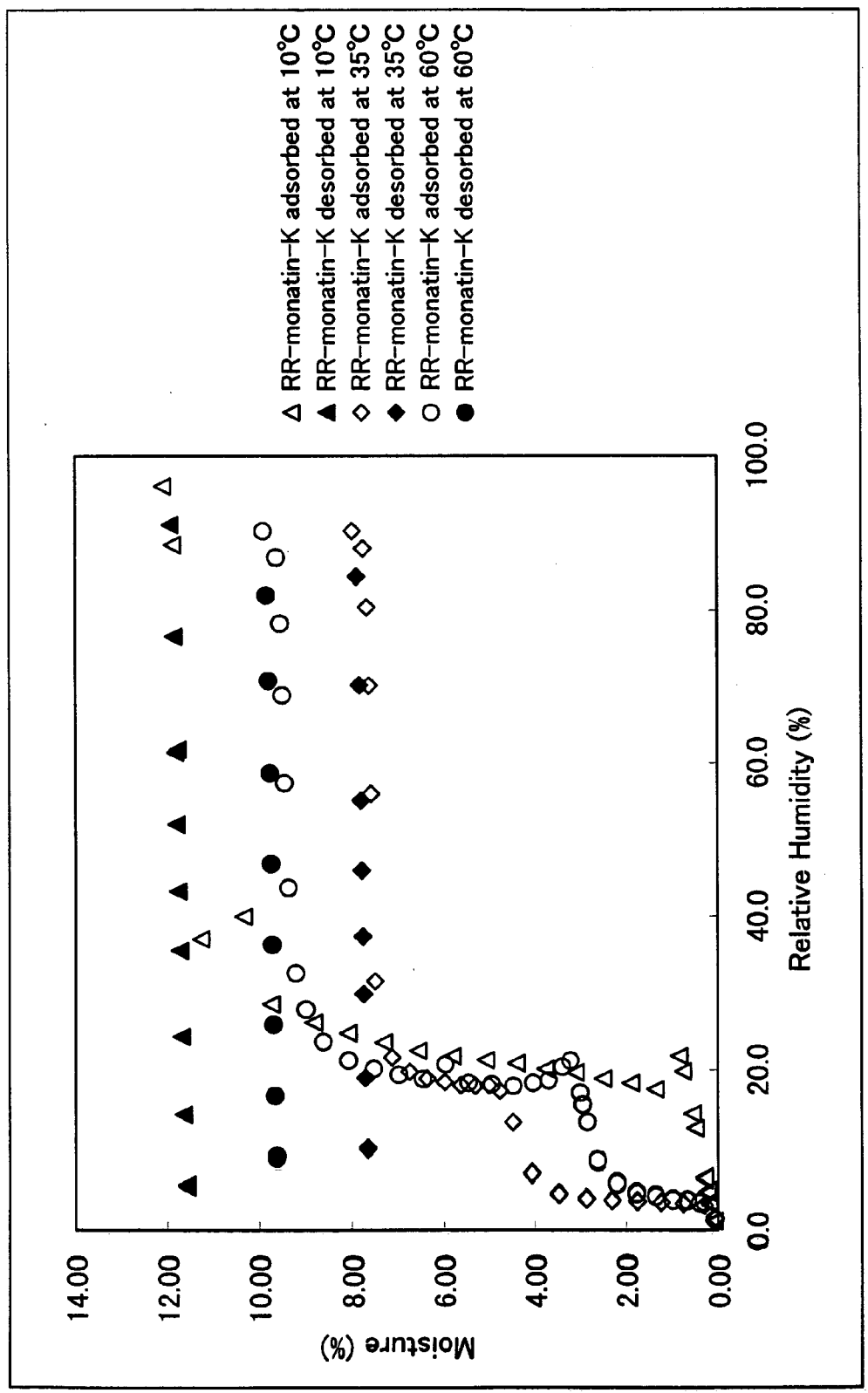

FIG. 29 shows steam adsorption and desorption (adsorption/desorption) curves of the potassium salt (crystallizing temperature: 10° C., 35° C., 60° C.) of a (2R,4R) monatin substance of Example 19.

Ordinate: Moisture (% by weight);
Abscissa: relative humidity (%)

| Δ: adsorbed at 10° C. | ▲: desorbed at 10° C. |
|---|---|
| ◇: adsorbed at 35° C. | ♦: desorbed at 35° C. |
| ○: adsorbed at 60° C. | ●: desorbed at 60° C. |

Figure 30:
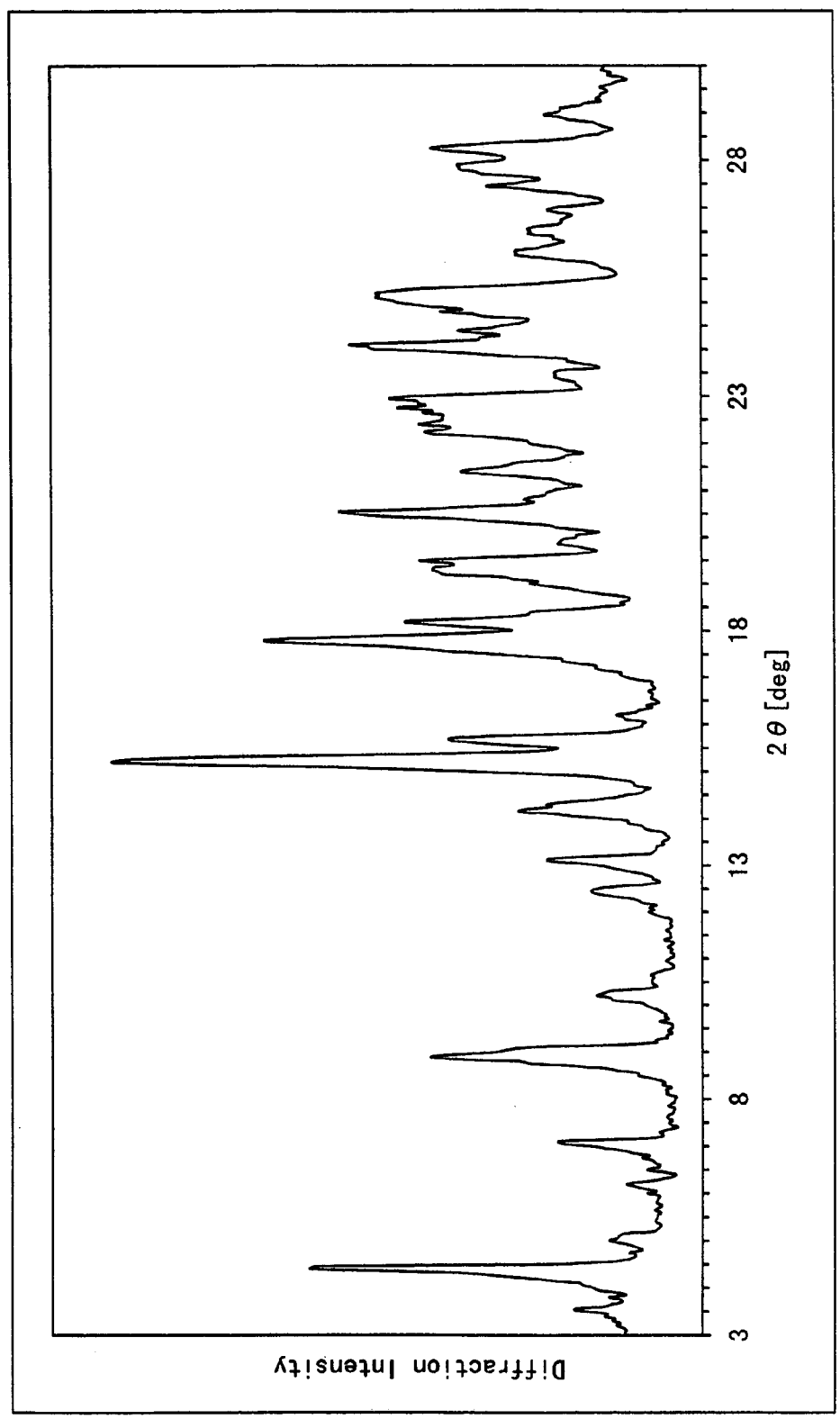

FIG. 30 is a powder X-ray diffraction chart after drying of sodium salt crystals of a (2R,4R) monatin substance of Example 20.

Figure 31:
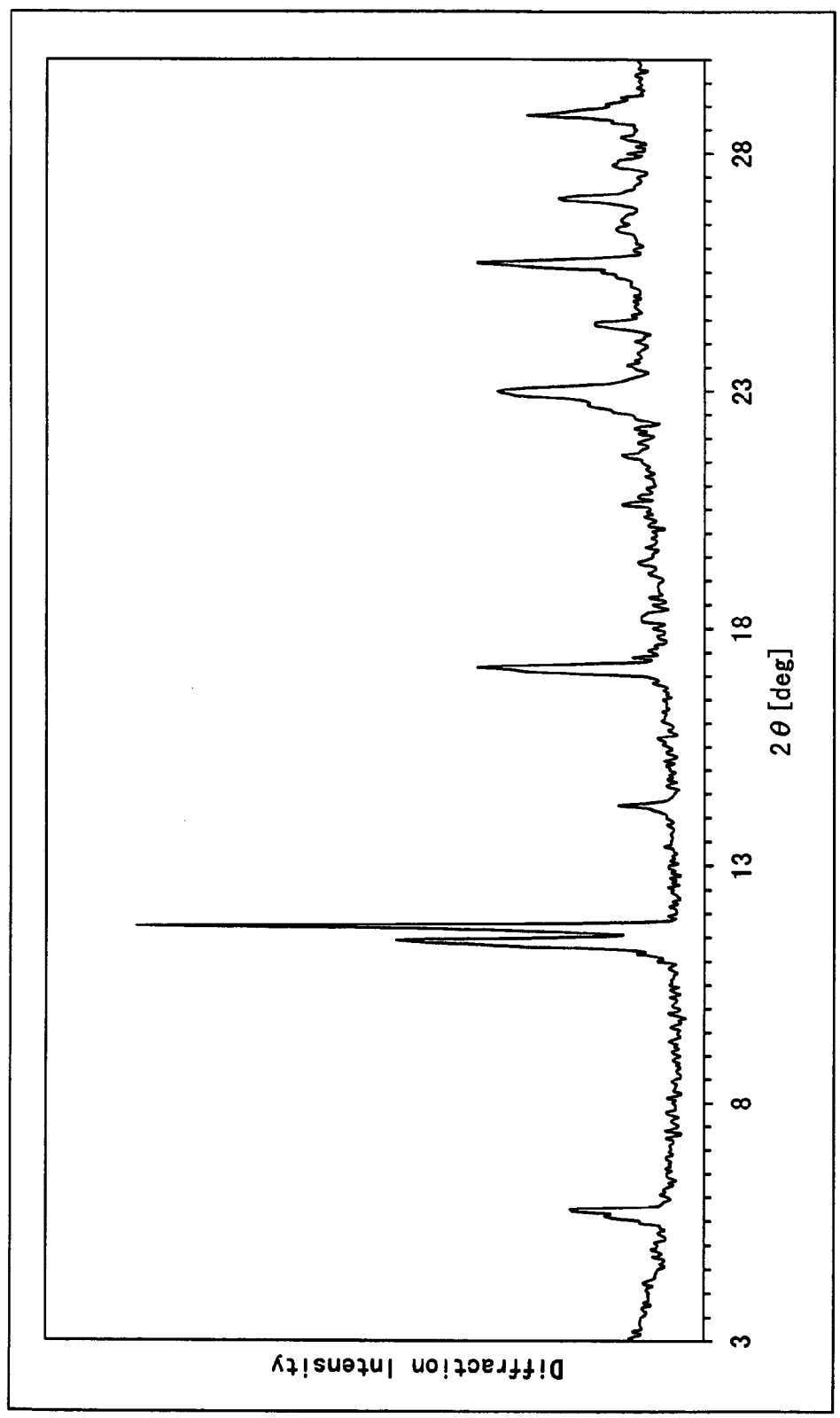

FIG. 31 is a powder X-ray diffraction chart of wet potassium salt crystals of a (2R,4R) monatin substance of Example A.

Figure 32:
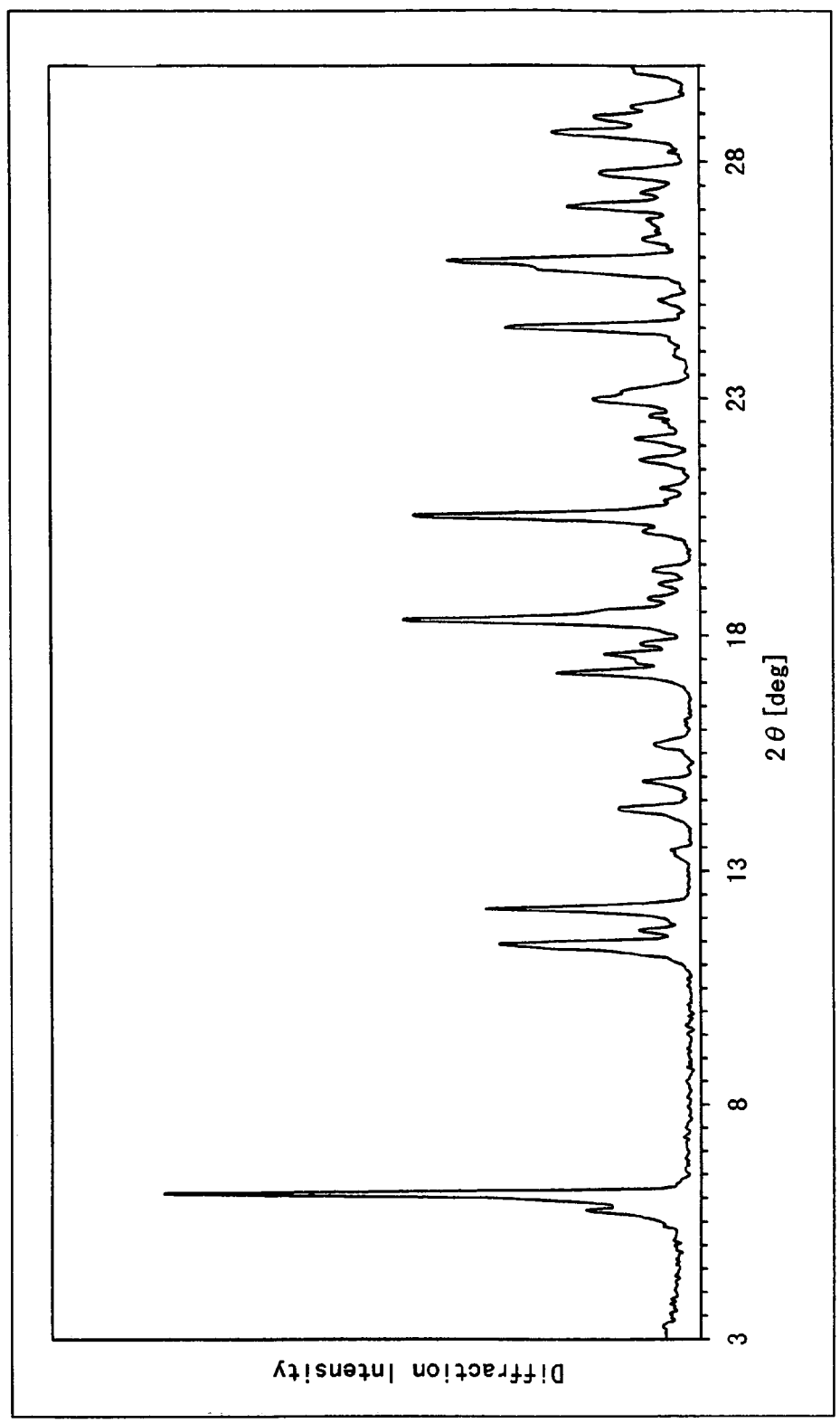

FIG. 32 is a powder X-ray diffraction chart of wet potassium salt crystals of a (2R,4R) monatin substance of Example B.

Figure 33:
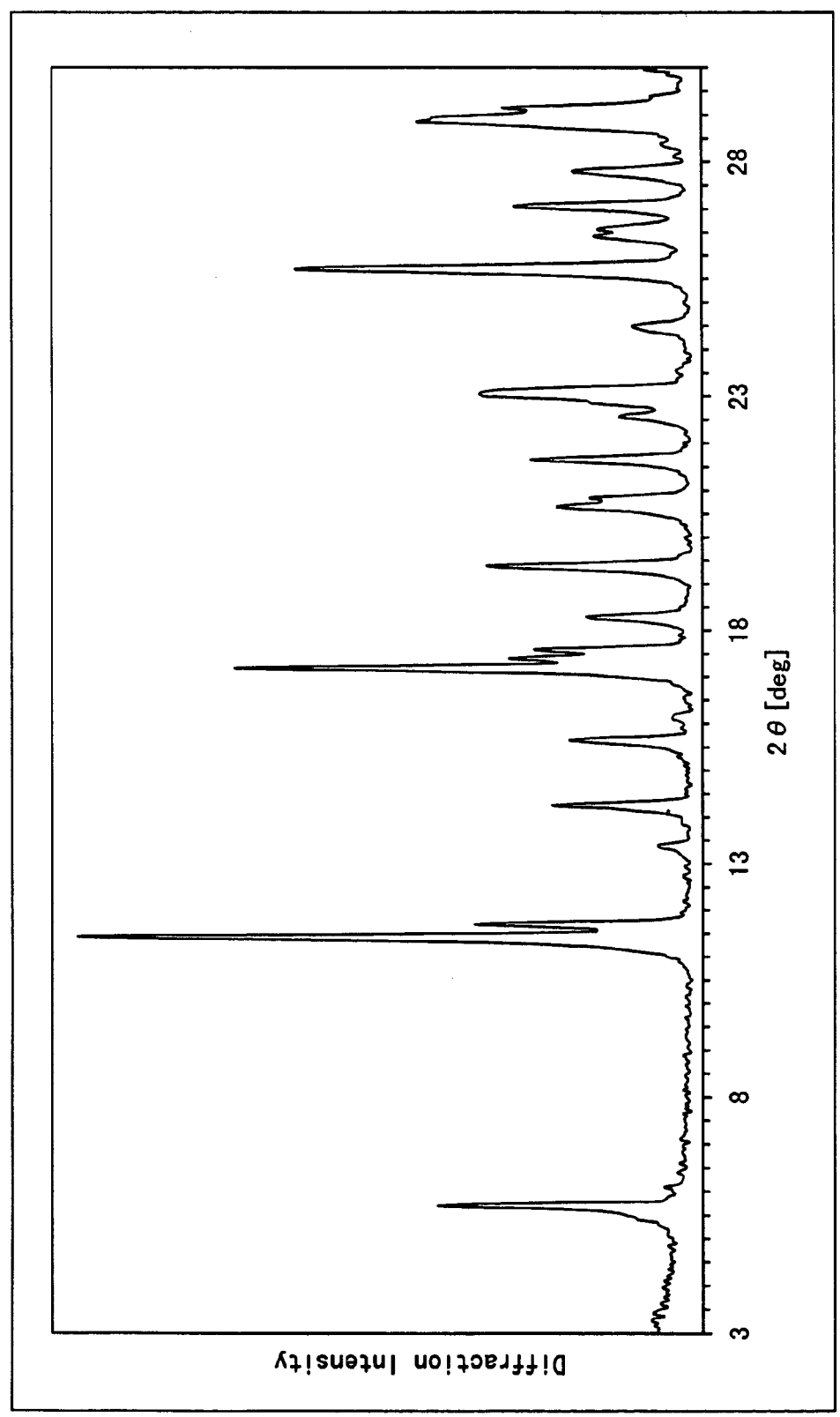

FIG. 33 is a powder X-ray diffraction chart of wet potassium salt crystals of a (2R,4R) monatin substance of Example C.

Figure 34:
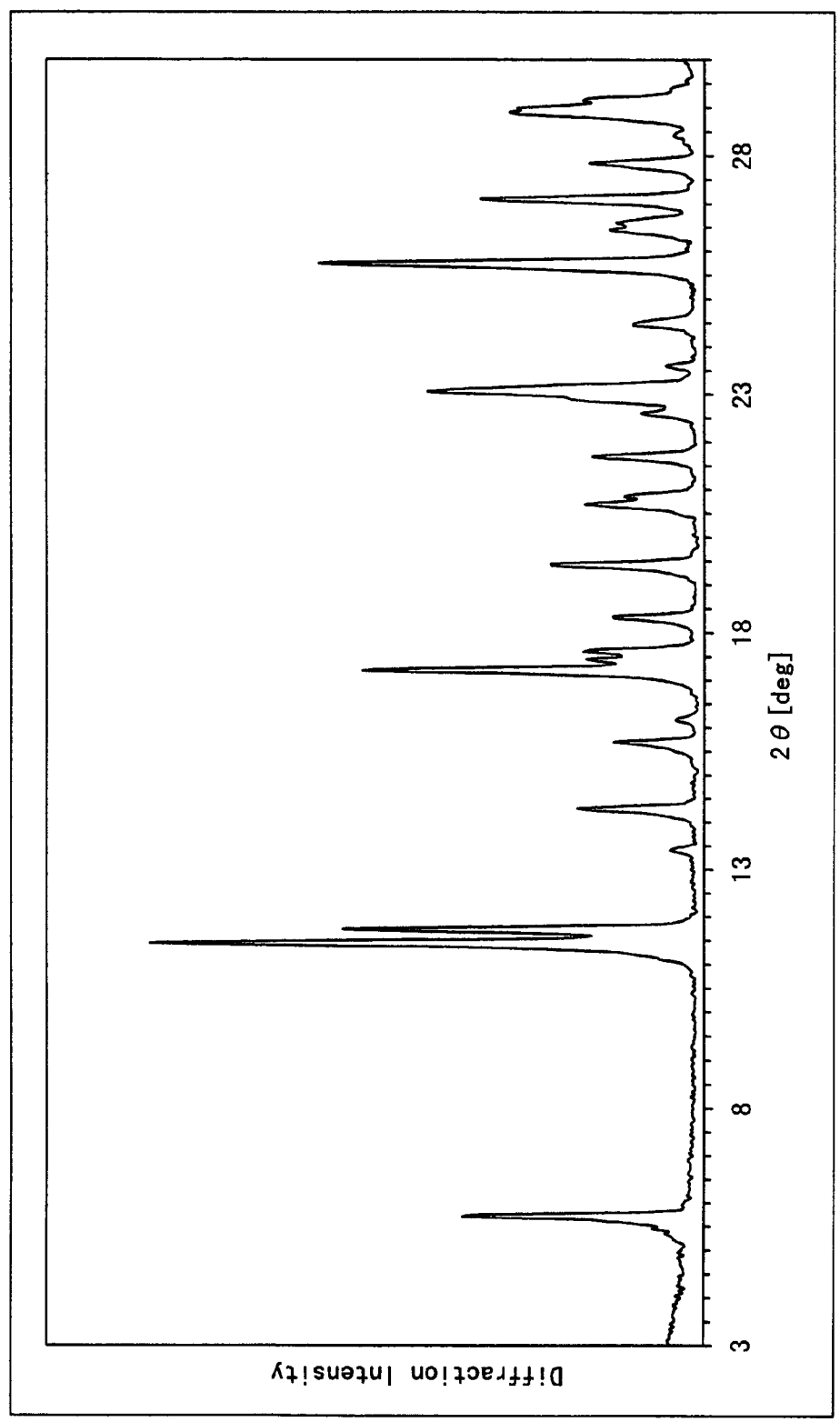

FIG. 34 is a powder X-ray diffraction chart of wet potassium salt crystals of a (2R,4R) monatin substance of Example D.

Figure 35:
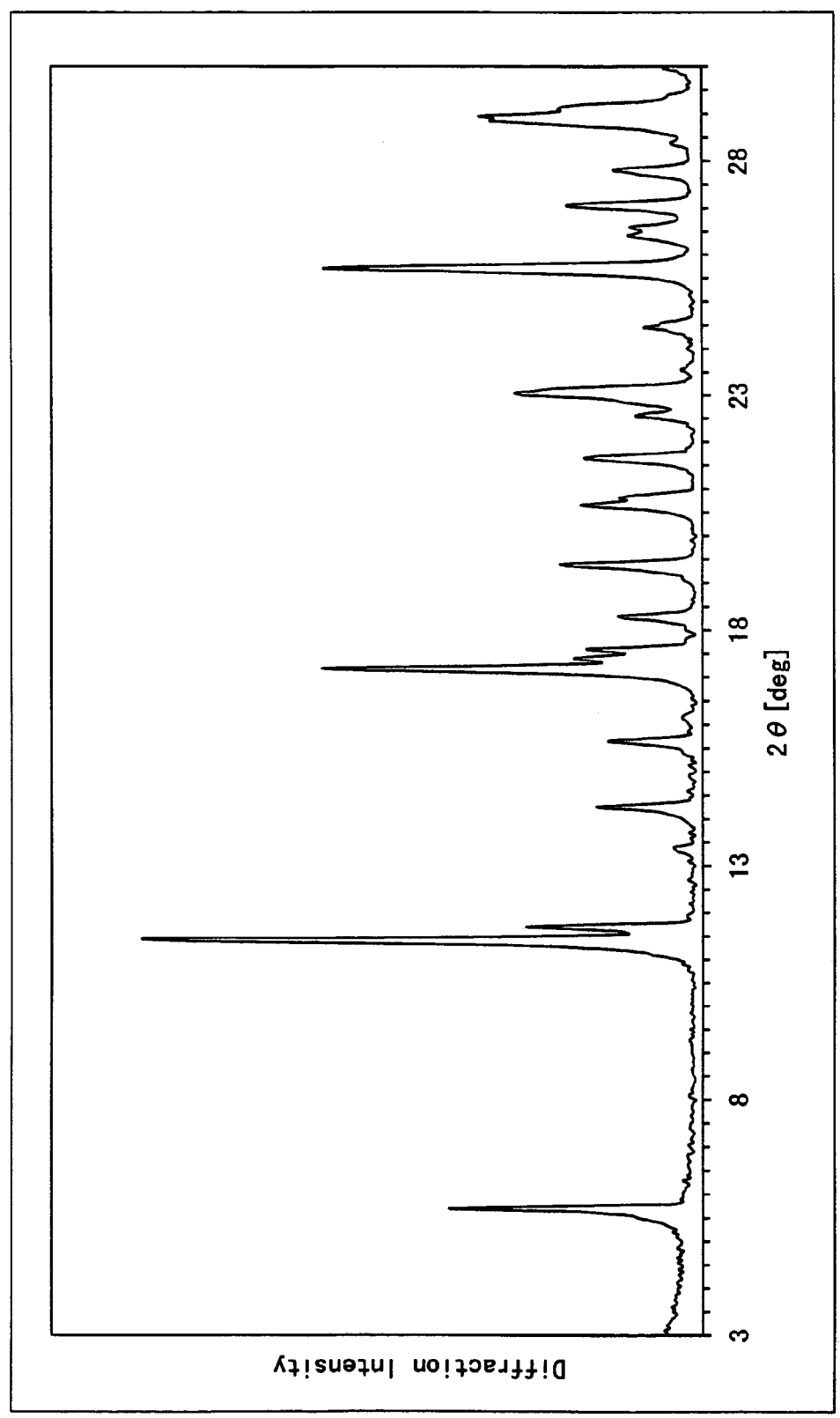

FIG. 35 is a powder X-ray diffraction chart of wet potassium salt crystals of a (2R,4R) monatin substance of Example E.

Figure 36:
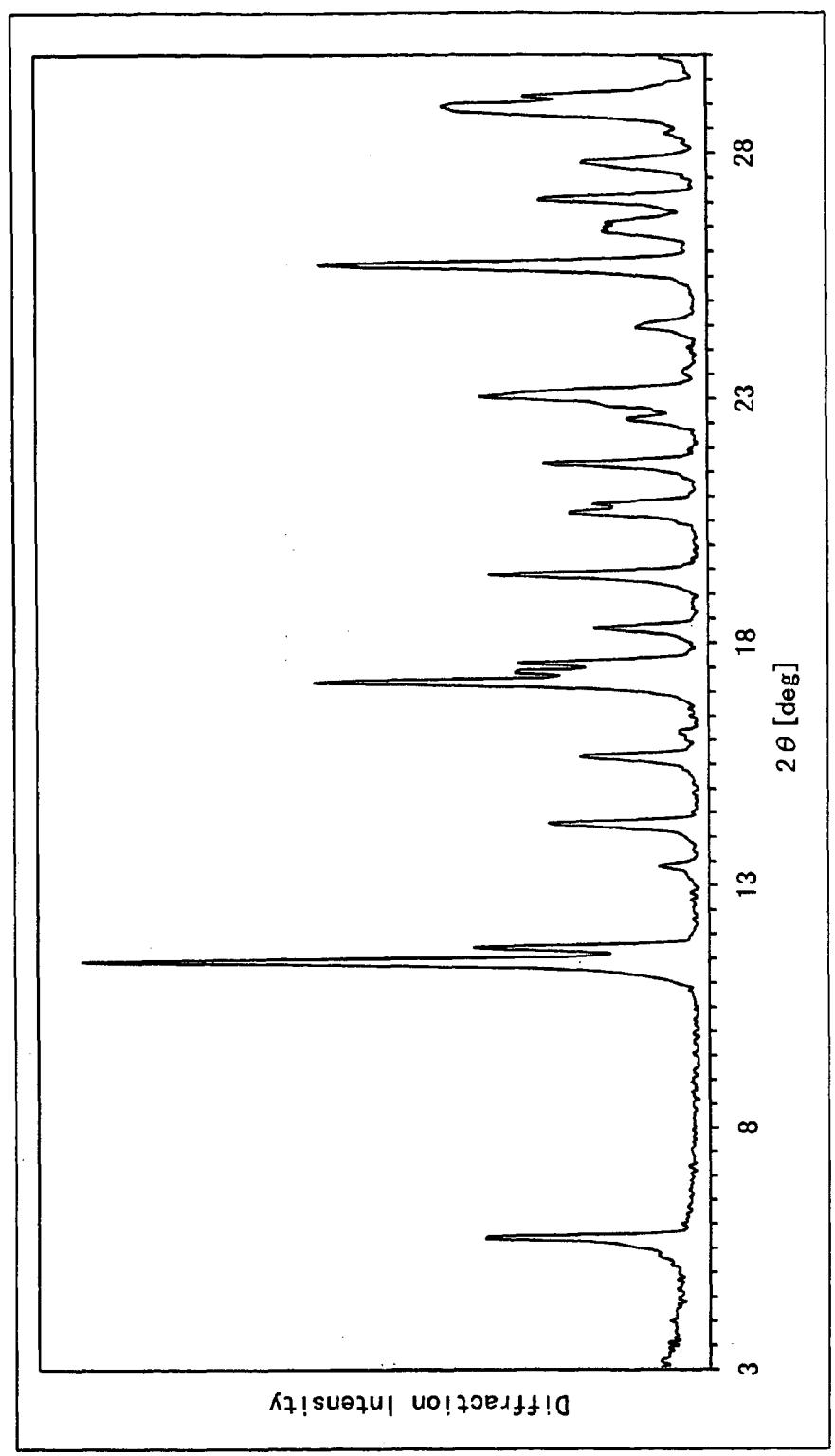

FIG. 36 is a powder X-ray diffraction chart of wet potassium salt crystals of a (2R,4R) monatin substance of Example F.

Figure 37:
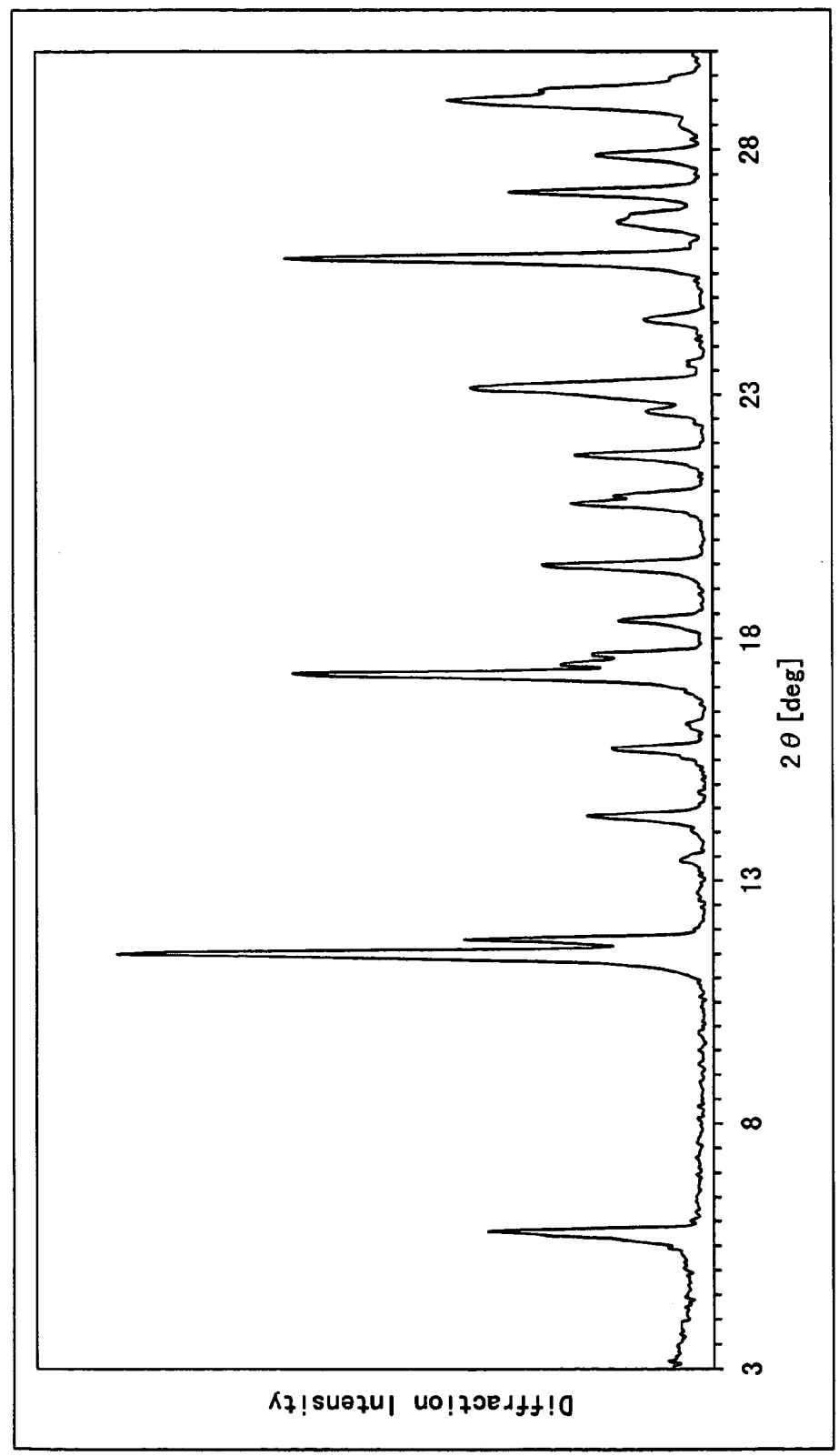

FIG. 37 is a powder X-ray diffraction chart of wet potassium salt crystals of a (2R,4R) monatin substance of Example G.

Figure 1:
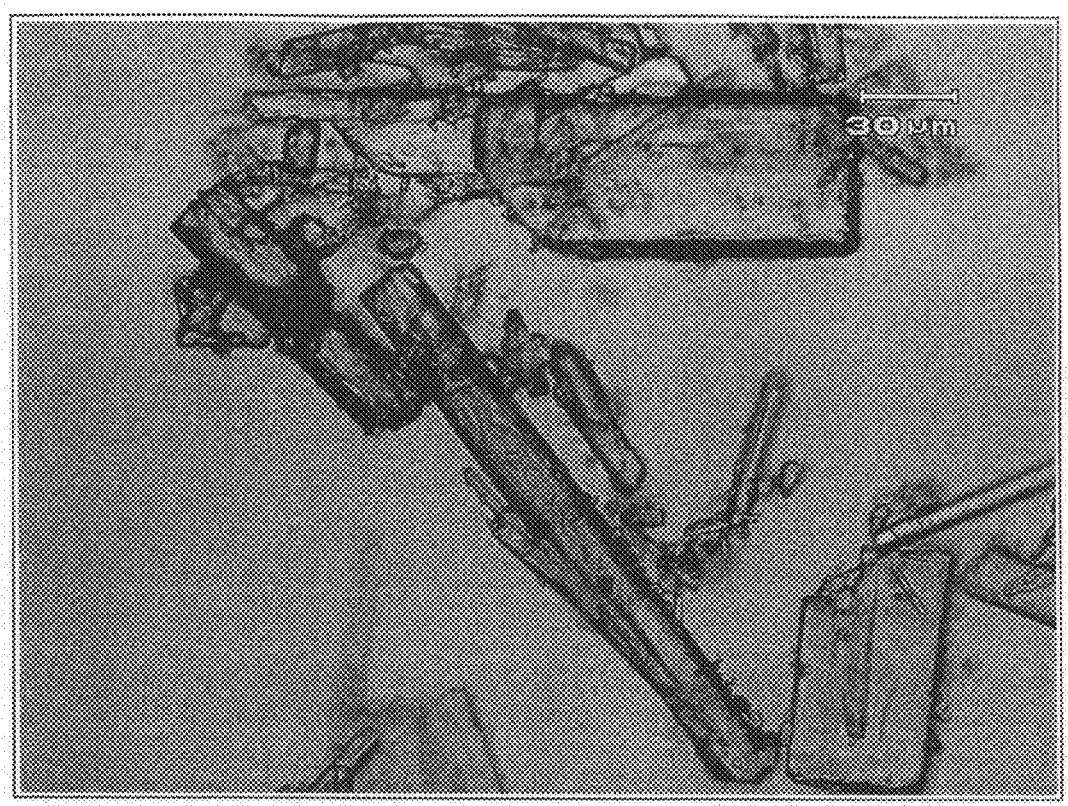
FIG. 1 shows an optical microphotograph (magnification: 200-power) immediately prior to separation of a crystallized solution of potassium salt crystals of a (2R,4R) monatin substance of Example 13.
Figures 1, 38:
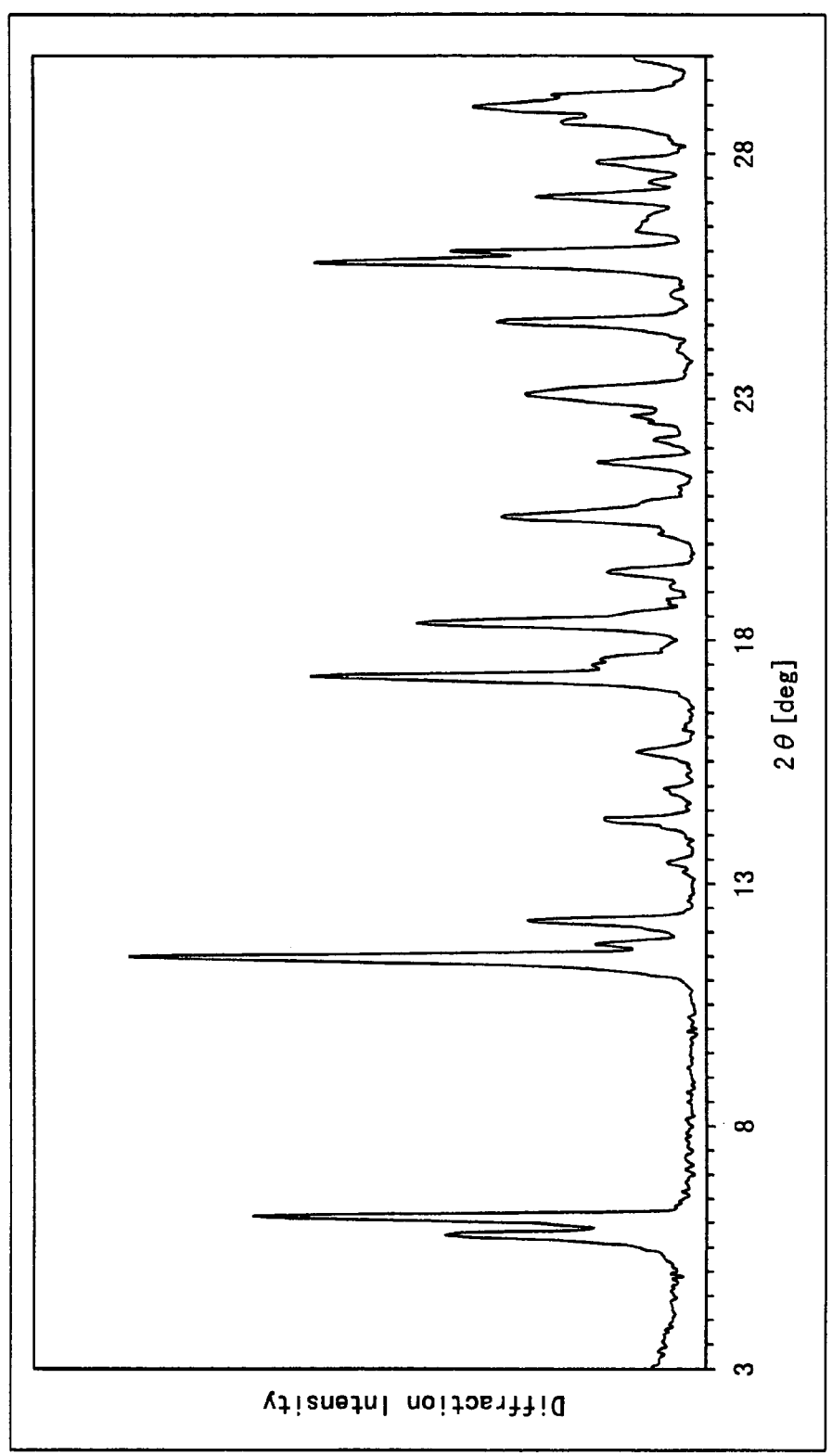
Figures 2, 38:
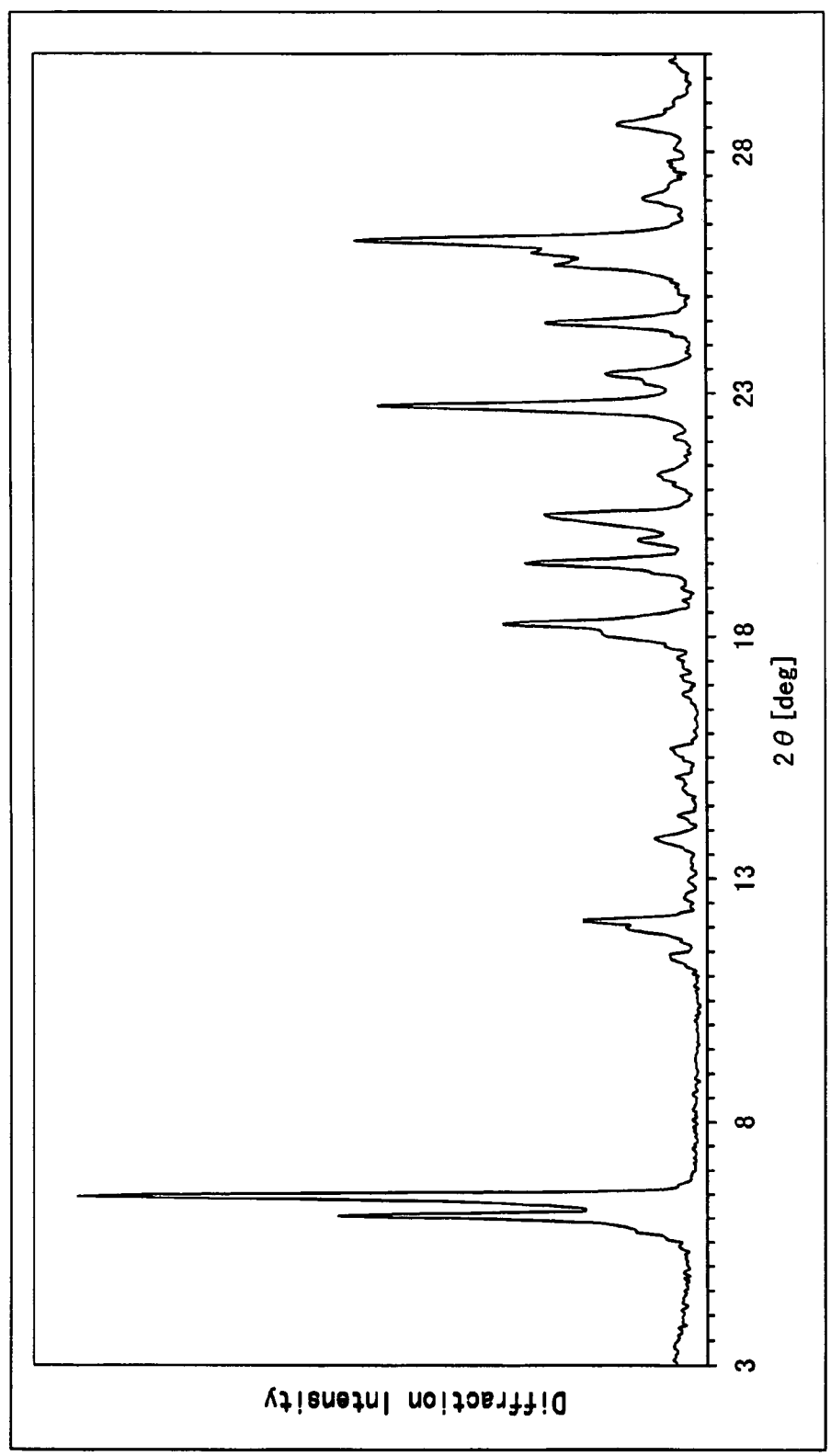

FIG. 38-1 is a powder X-ray diffraction chart of wet potassium salt crystals of a (2R,4R) monatin substance of Example H.

Figure 2:
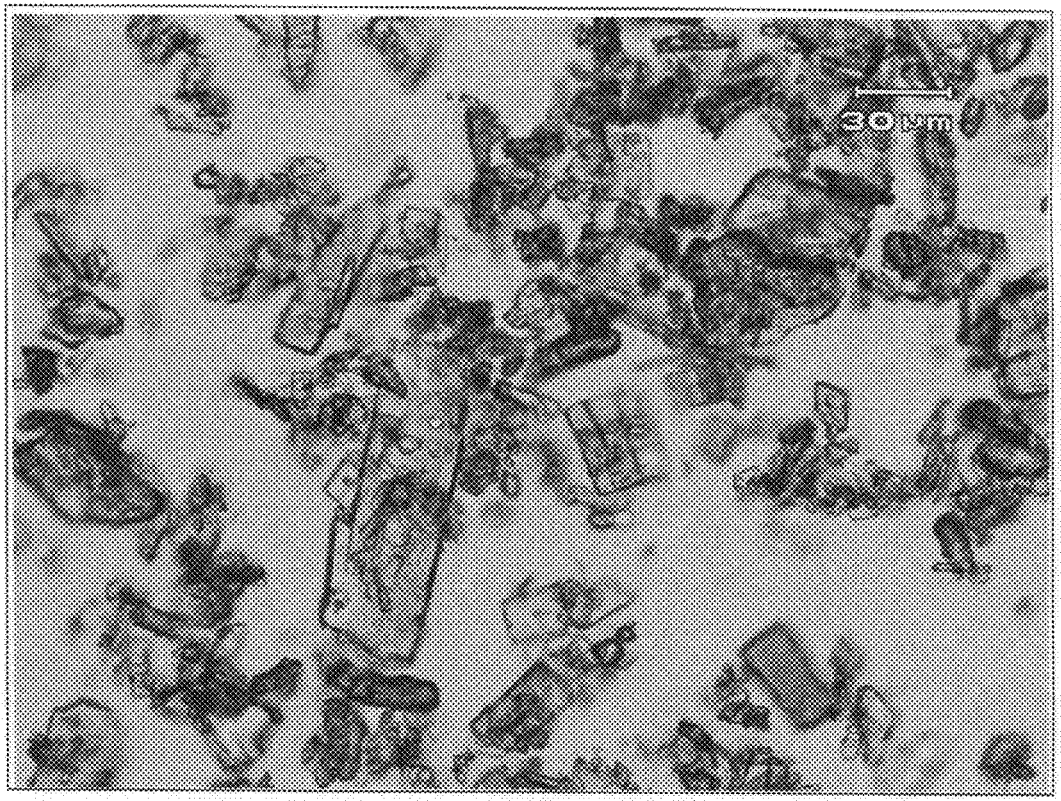
FIG. 2 shows an optical microphotograph (magnification: 200-power) after drying of the potassium salt crystals of a (2R,4R) monatin substance of Example 13.

FIG. 38-2 is a powder X-ray diffraction chart after drying of potassium salt crystals of a (2R,4R) monatin substance of Example H.

Figures 1, 39:
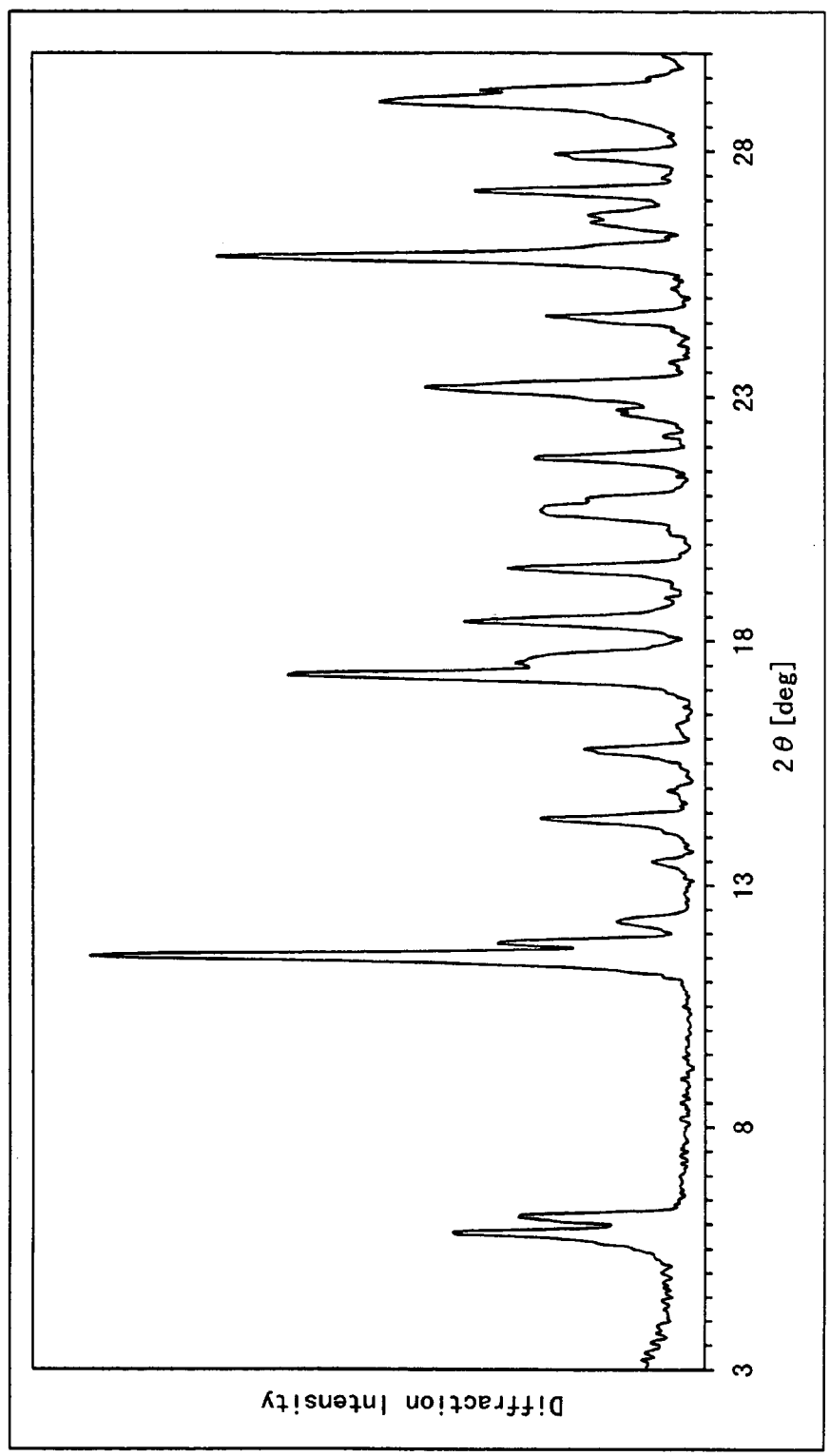
Figures 2, 39:
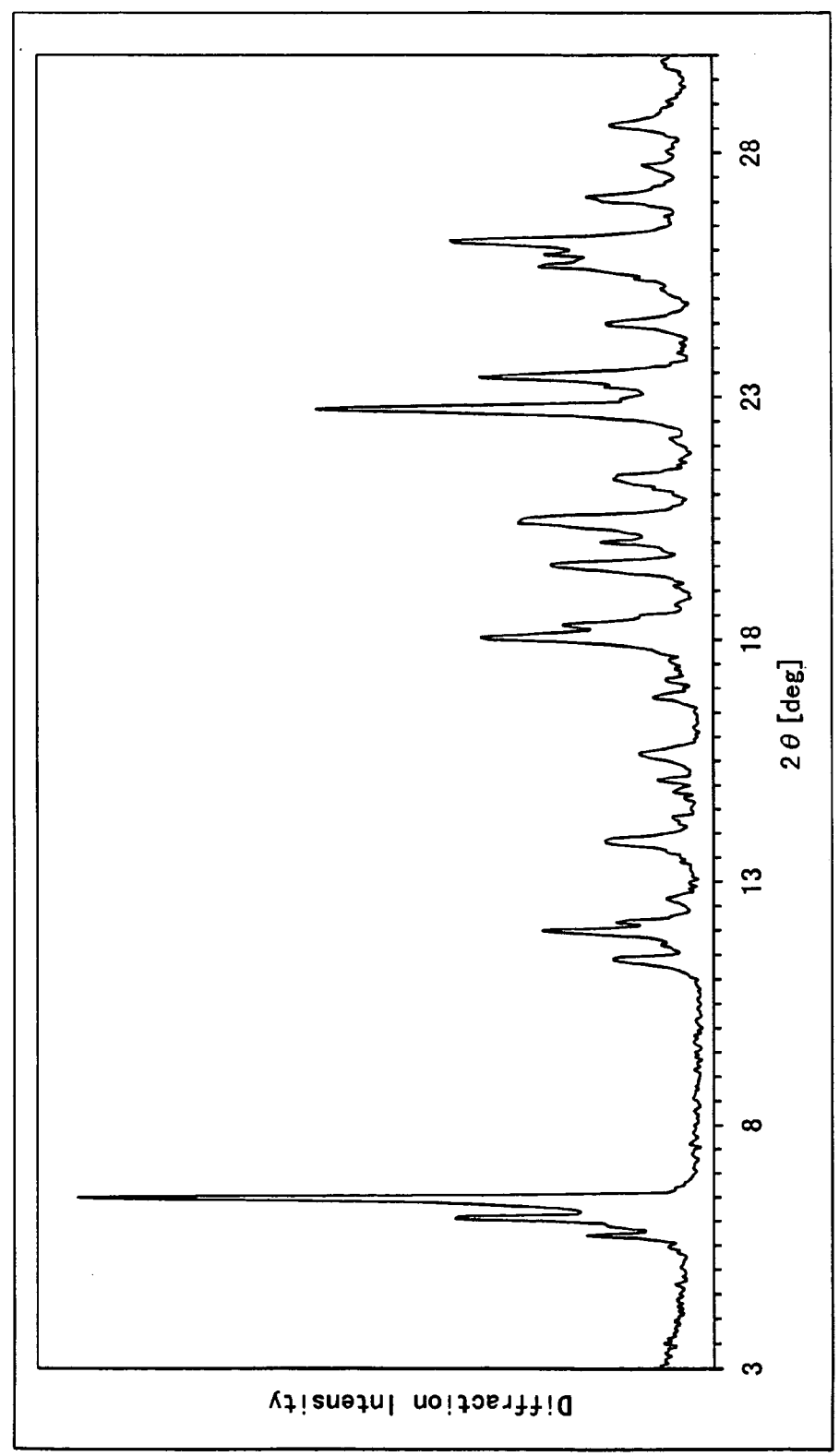

FIG. 39-1 is a powder X-ray diffraction chart of wet potassium salt crystals of a (2R,4R) monatin substance of Example I.

FIG. 39-2 is a powder X-ray diffraction chart after drying of potassium salt crystals of a (2R,4R) monatin substance of Example I.

Figures 1, 40:
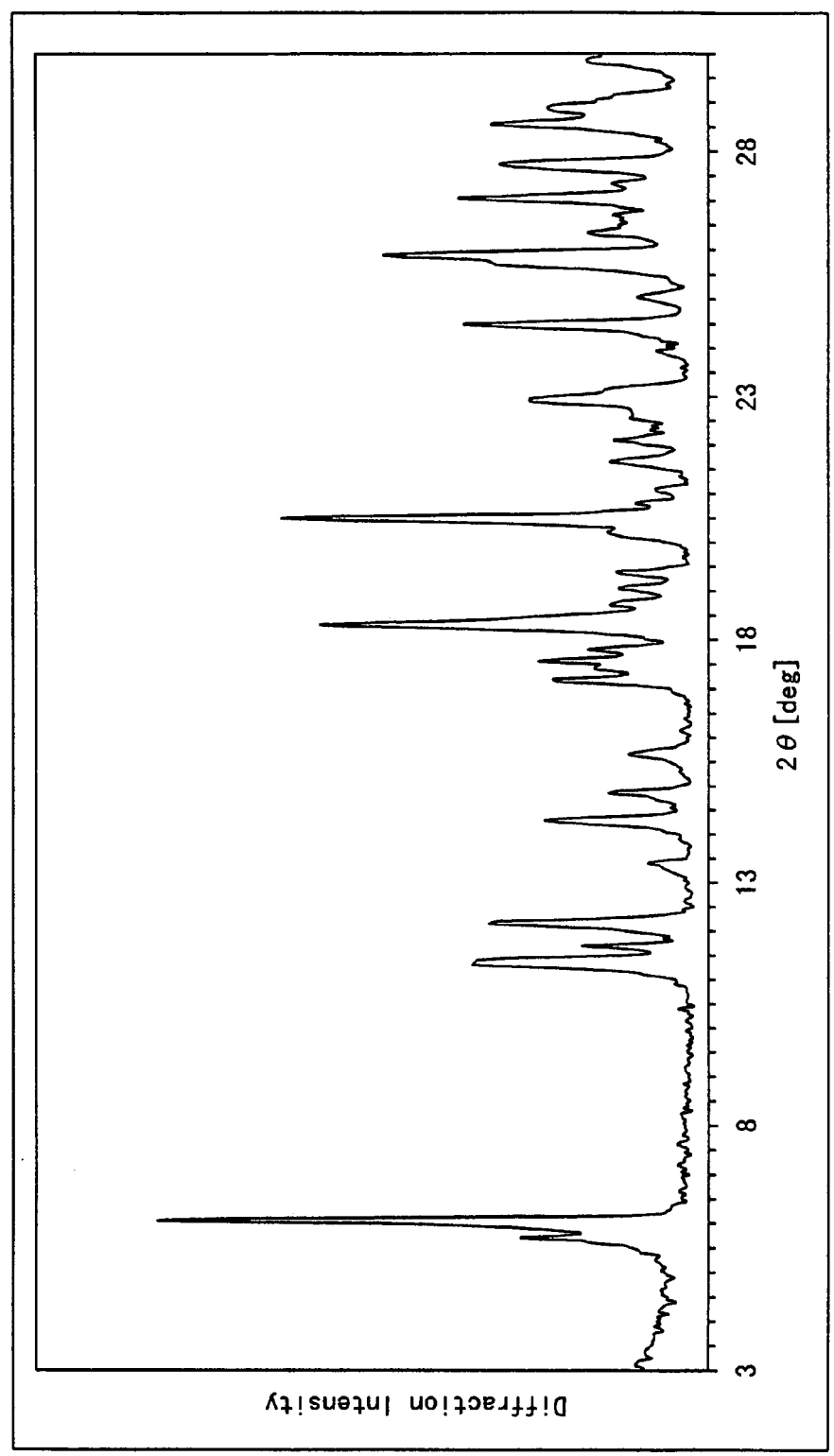
Figures 2, 40:
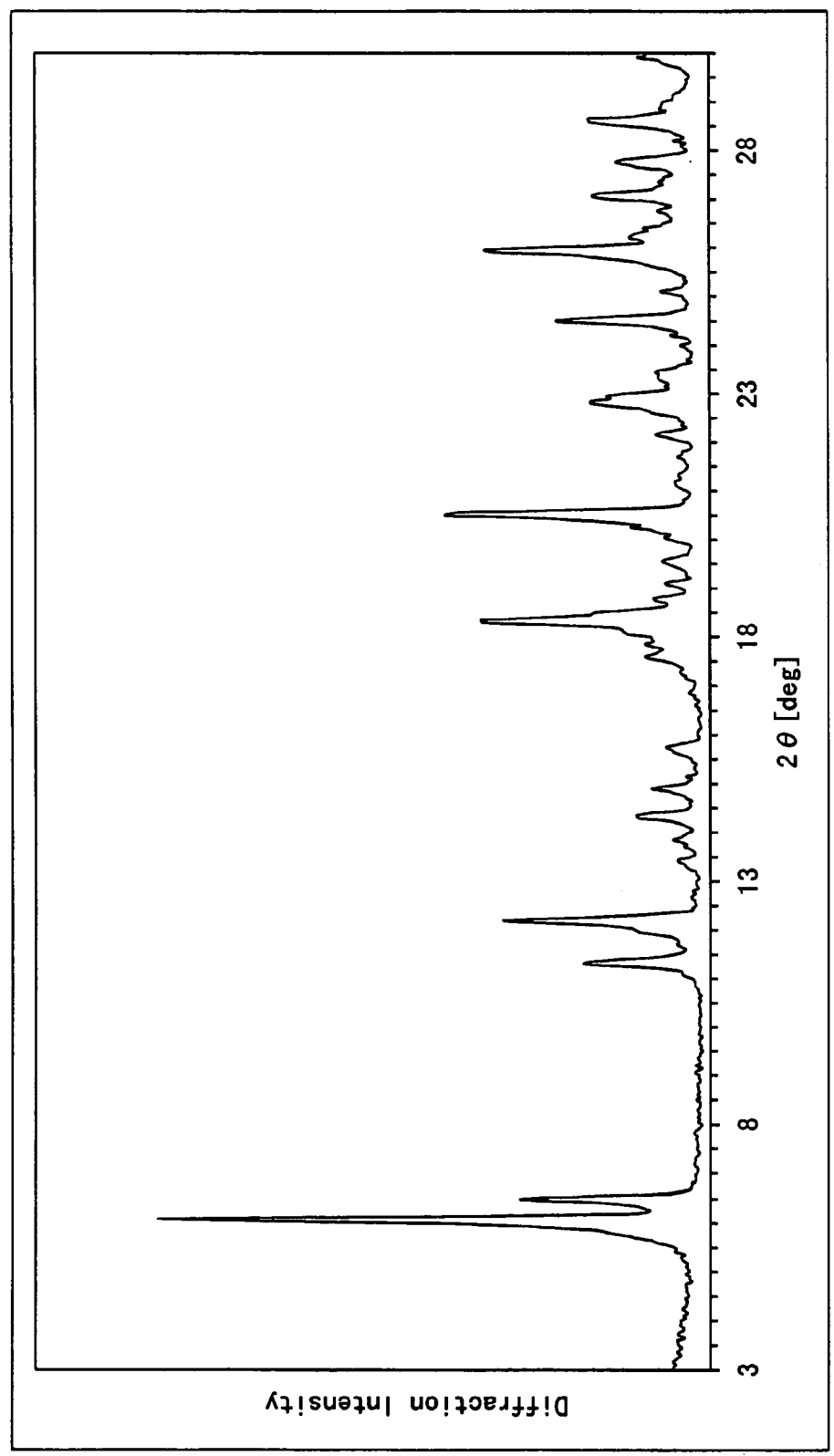

FIG. 40-1 is a powder X-ray diffraction chart of wet potassium salt crystals of a (2R,4R) monatin substance of Example J.

FIG. 40-2 is a powder X-ray diffraction chart after drying of potassium salt crystals of a (2R,4R) monatin substance of Example J.

Figures 1, 41:
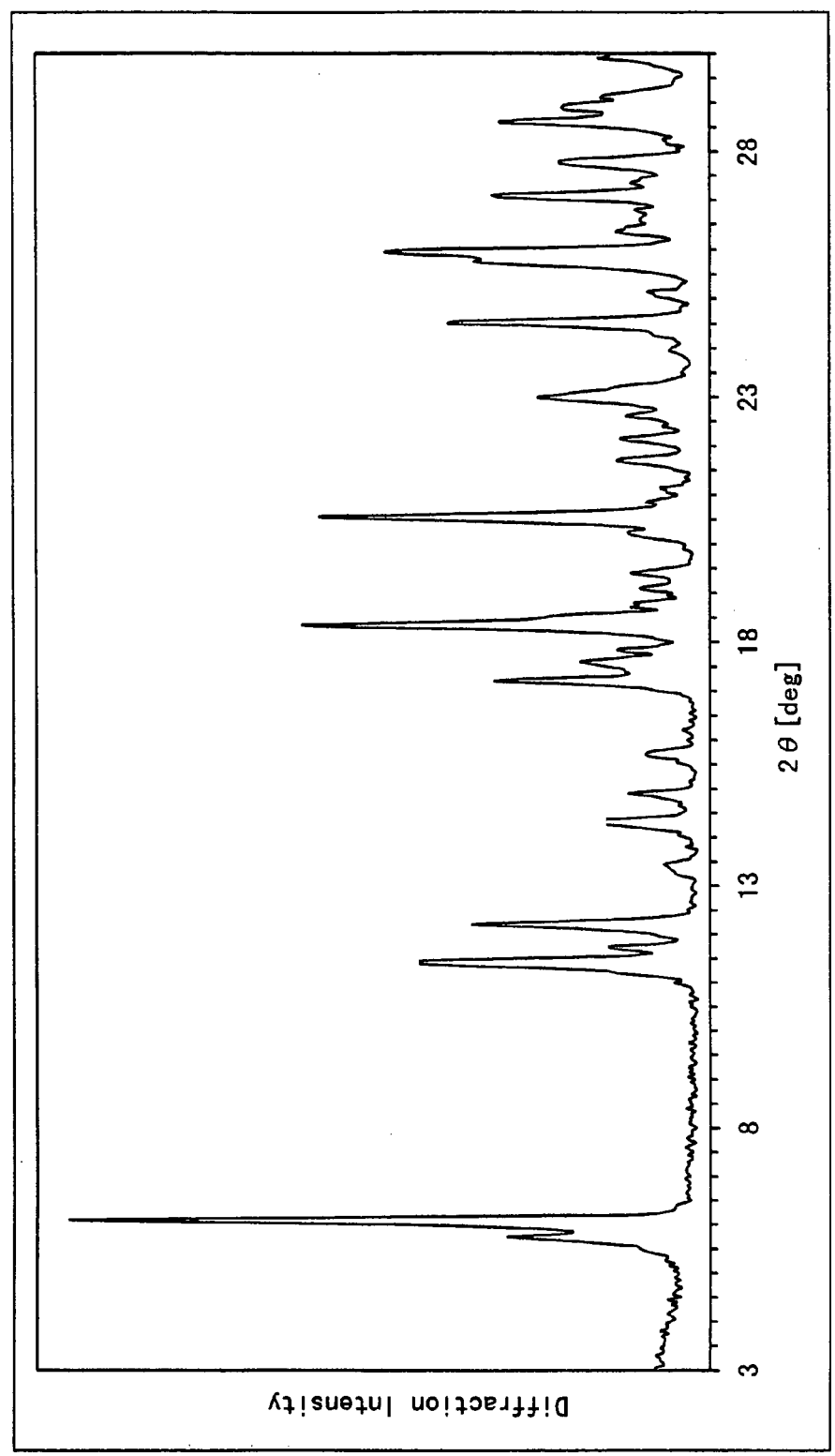
Figures 2, 41:
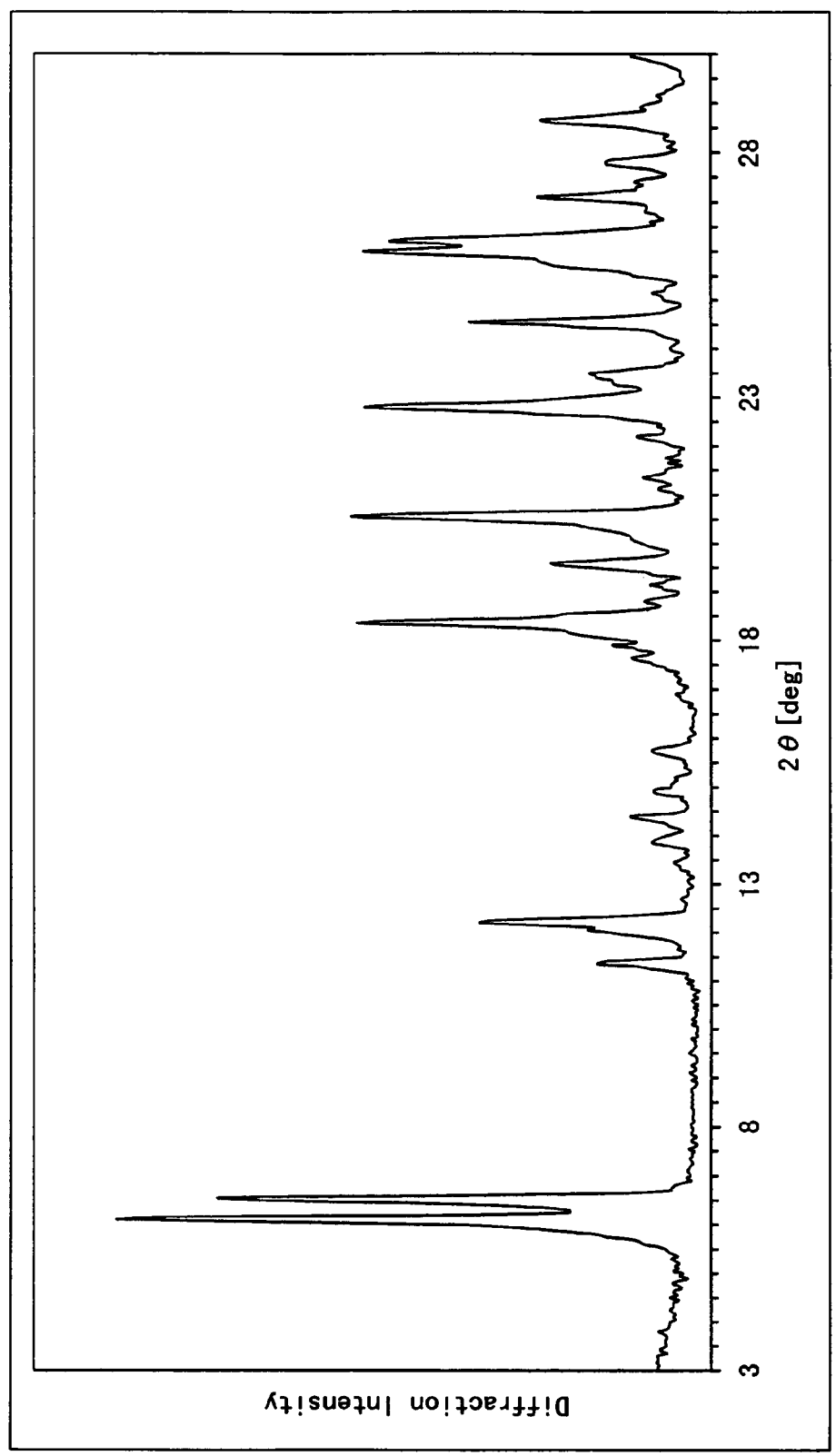

FIG. 41-1 is a powder X-ray diffraction chart of wet potassium salt crystals of a (2R,4R) monatin substance of Example K.

FIG. 41-2 is a powder X-ray diffraction chart after drying of potassium salt crystals of a (2R,4R) monatin substance of Example K.

Figure 42:
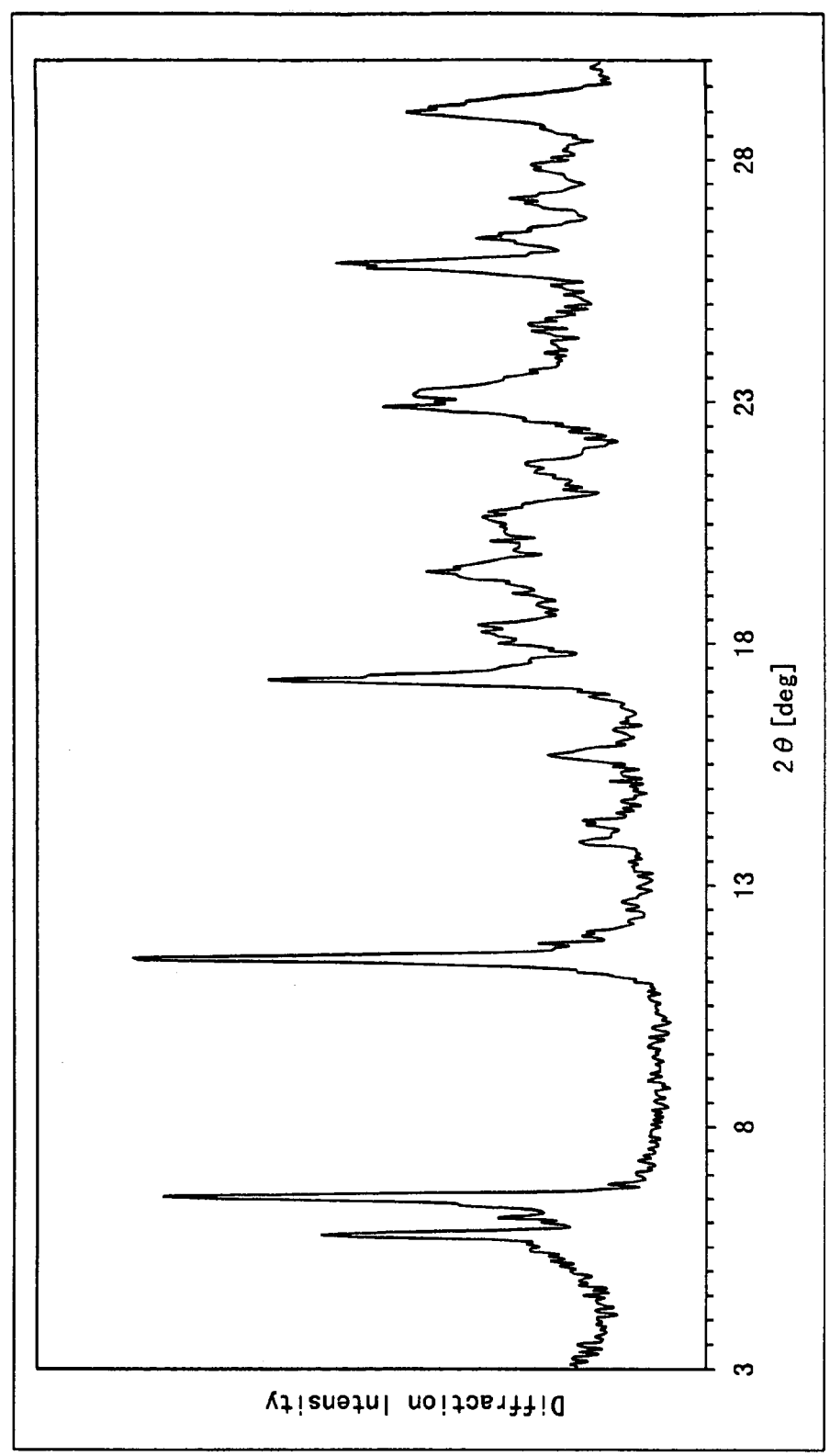

FIG. 42 is a powder X-ray diffraction chart of wet potassium salt crystals of a (2R,4R) monatin substance of Example L.

Figure 43:
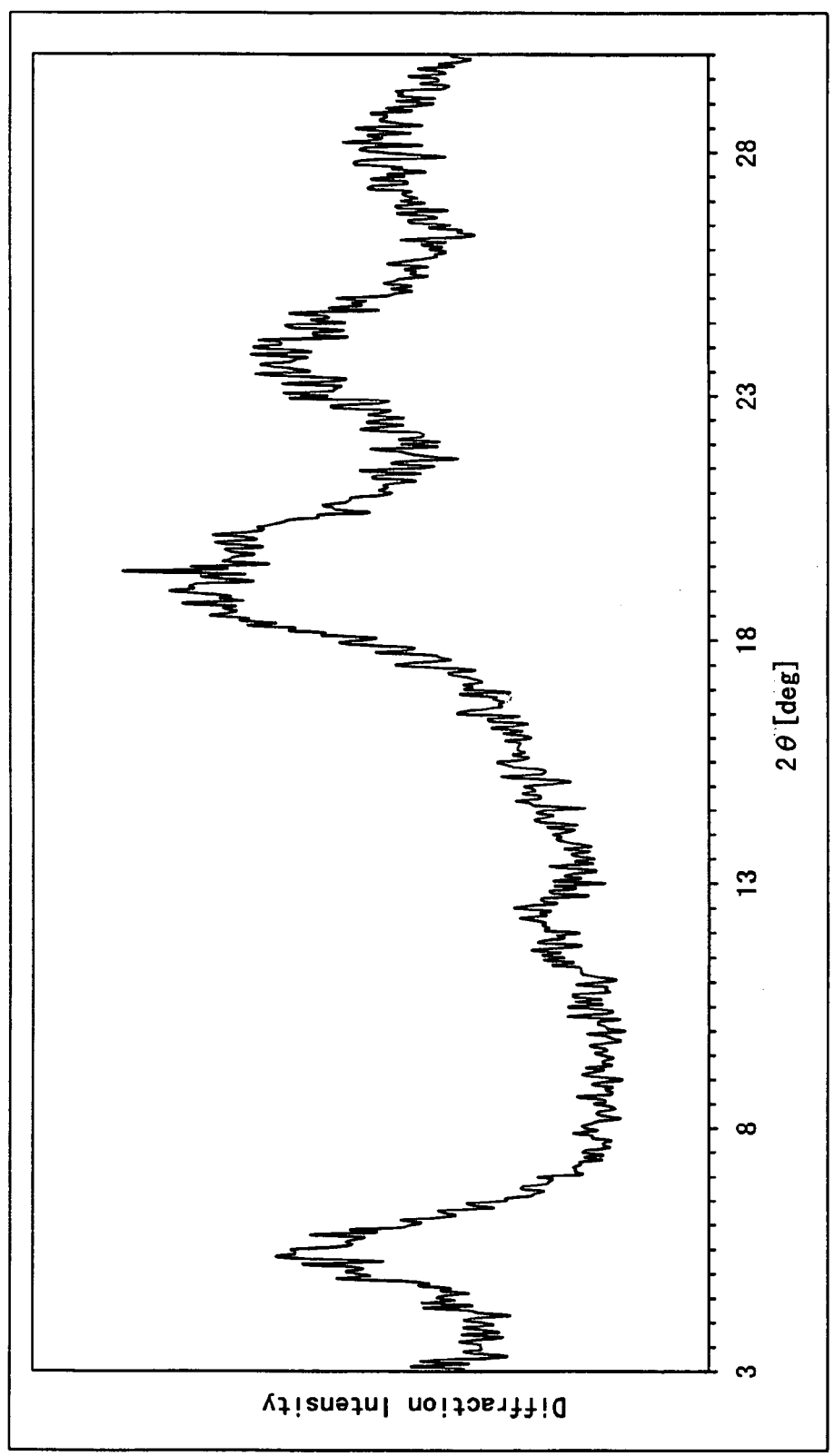

FIG. 43 is a powder X-ray diffraction chart of potassium salt solid of a (2R,4R) monatin substance of Example M.

Figure 44:
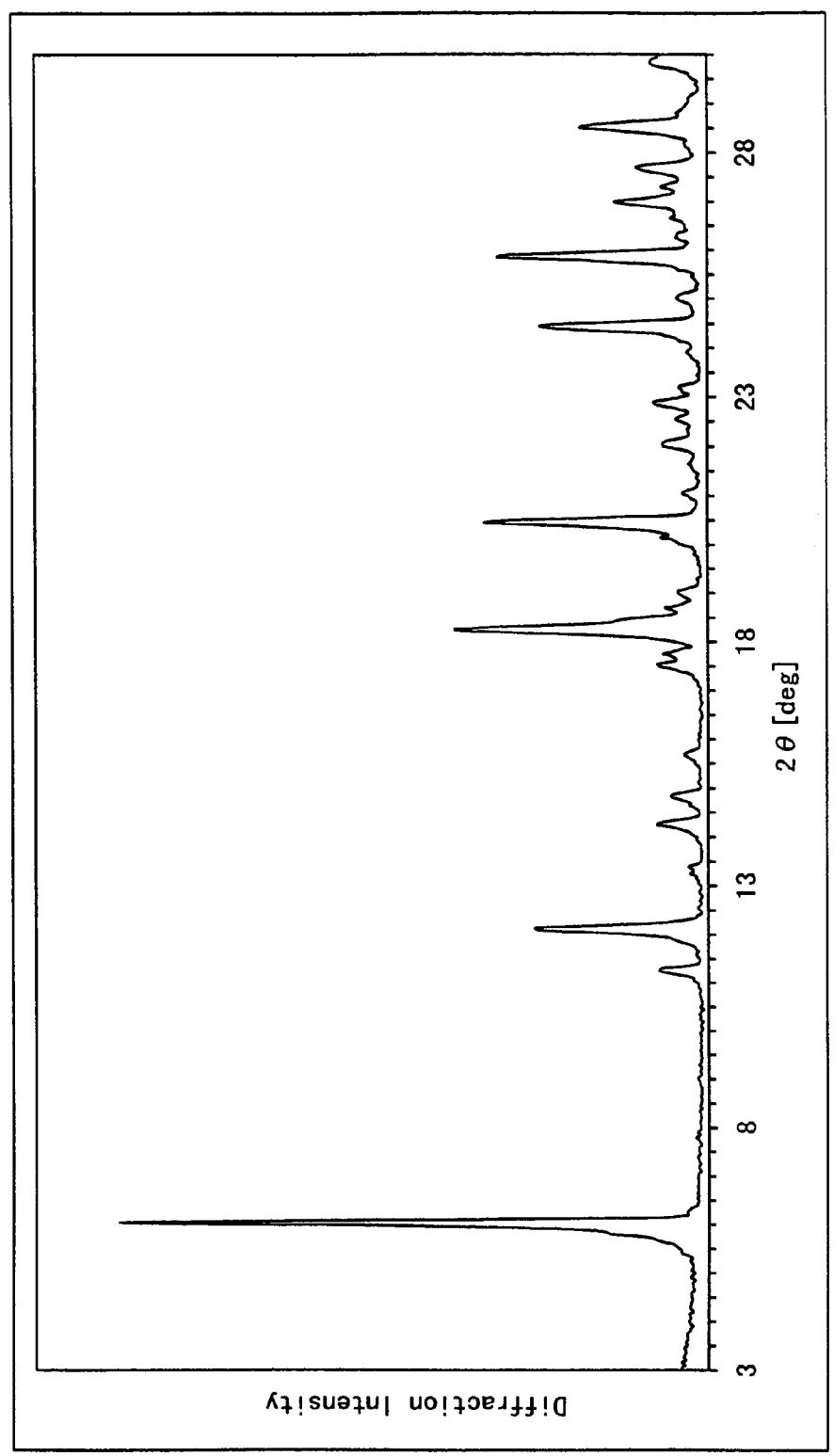

FIG. 44 is a powder X-ray diffraction chart of potassium salt crystals of a (2R,4R) monatin substance of Example N.

Figure 45:
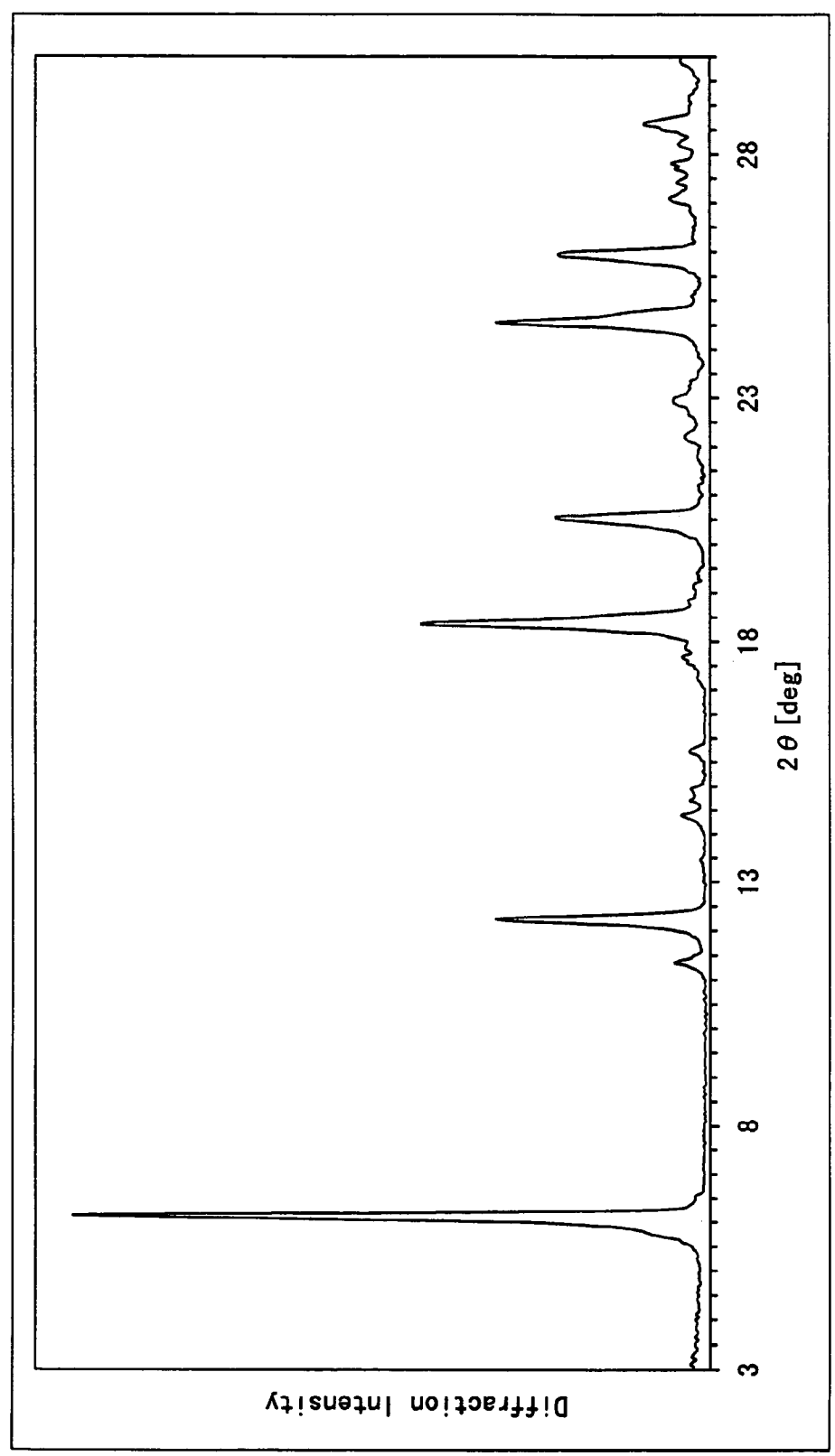

FIG. 45 is a powder X-ray diffraction chart of potassium salt crystals of a (2R,4R) monatin substance of Example O.

Figure 46:
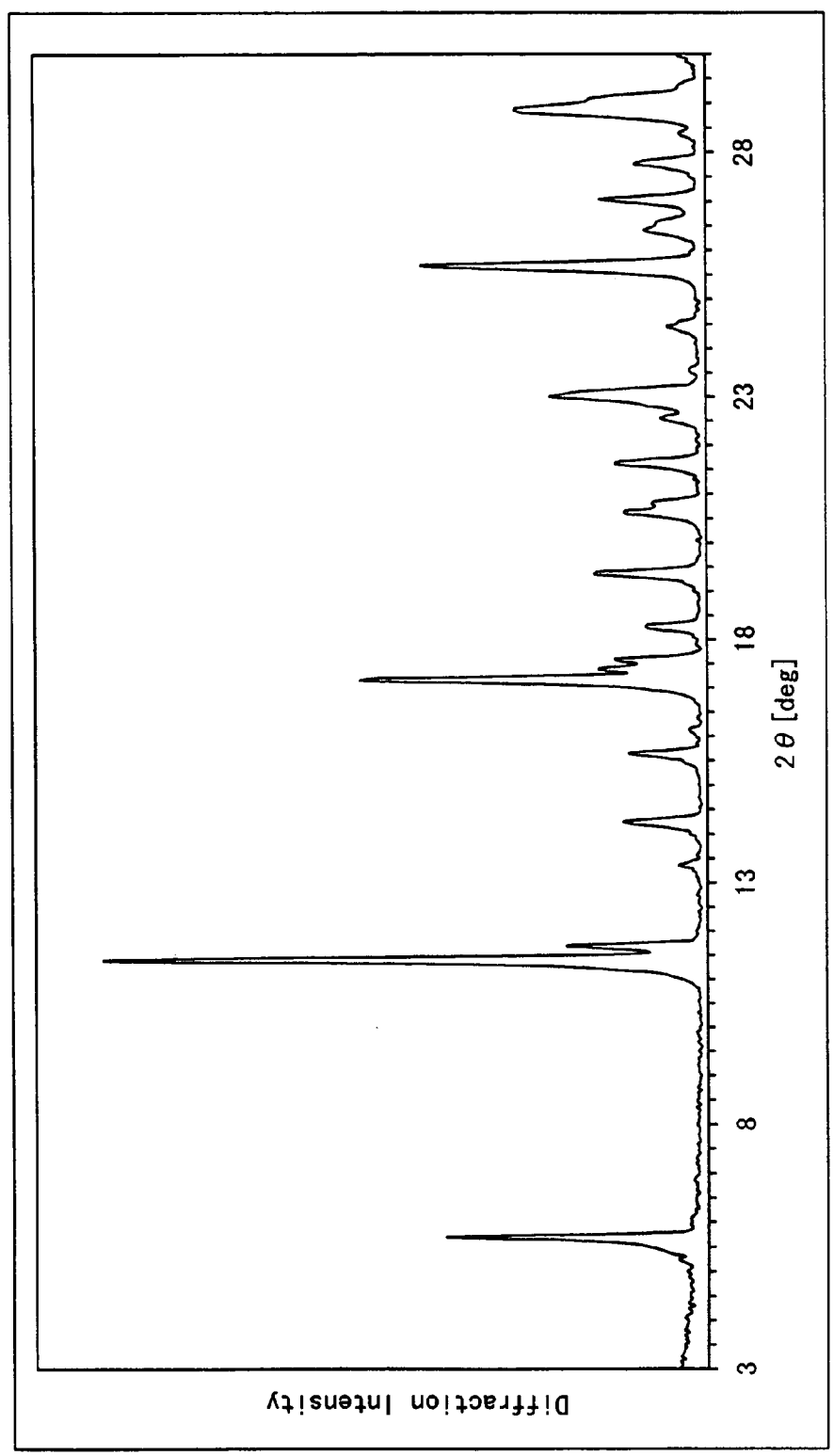

FIG. 46 is a powder X-ray diffraction chart of potassium salt crystals of a (2R,4R) monatin substance of Example P.

Figure 47:
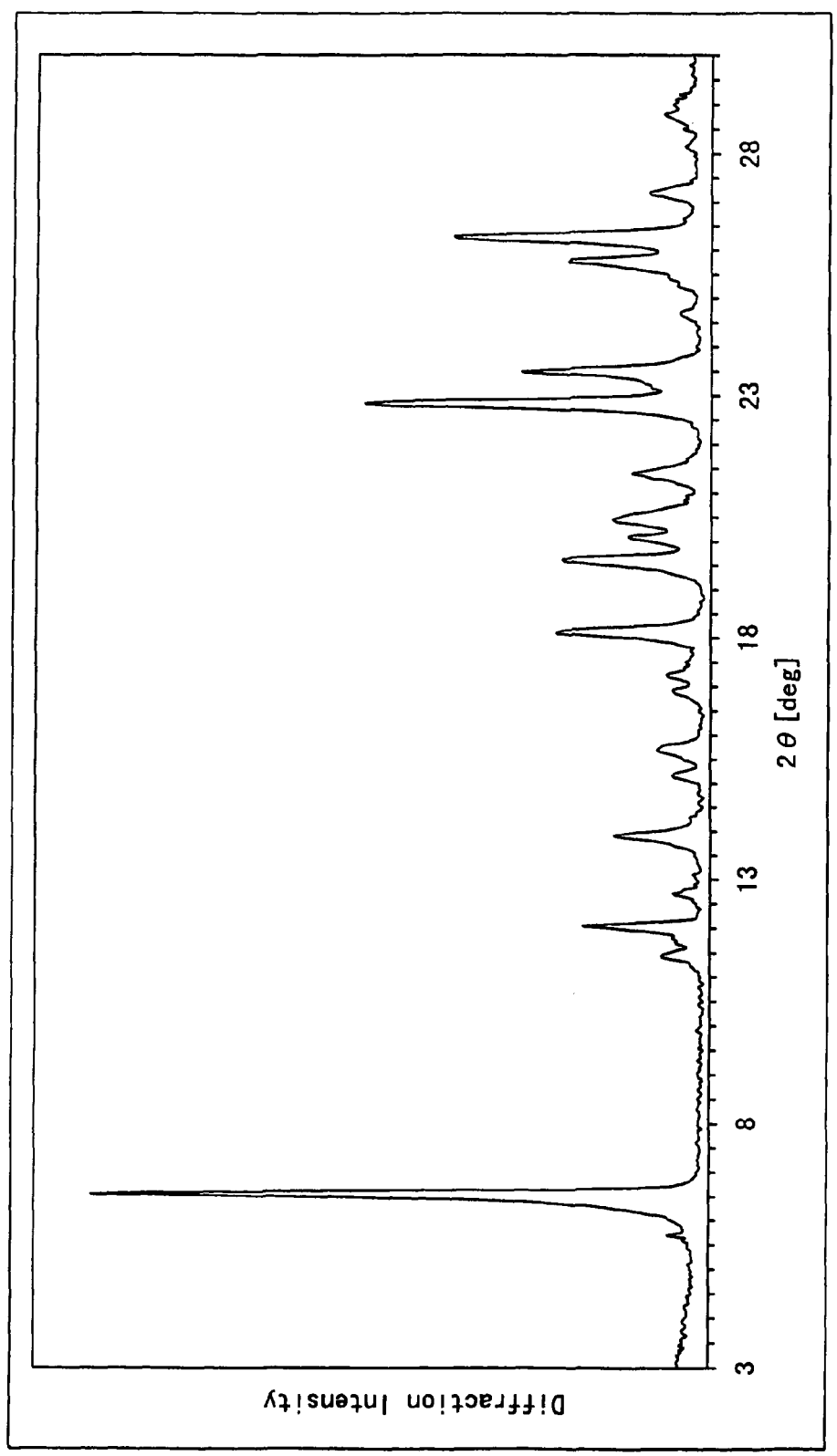

FIG. 47 is a powder X-ray diffraction chart of potassium salt crystals of a (2R,4R) monatin substance of Example Q.

DETAILED DESCRIPTION OF THE INVENTION

Unless specifically defined, all technical and scientific terms used herein have the same meaning as commonly understood by a skilled artisan in enzymology, chemistry, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

A problem in the art to be solved by the present invention is to provide a substance possessing a sweet taste that may be used as a sweetener. To be more specific, the problem is to separate and purify each of naturally occurring monatin and three non-natural stereoisomers thereof as pure substances. In particular, the present invention seeks to provide crystalline forms of the aforementioned compounds, to establish a method for confirming the optical purity thereof, and to confirm the intensity of sweet taste (sweetening potency; degree of sweet taste) of a natural-type monatin (a (2S,4S) substance) which has been said to be 800- to 1400-fold of sucrose. Further, it is also an important problem that, for crystals of each of the salts of those stereoisomers, characteristics such as various physical properties are made clear so that practical value from the view of physical properties is made clear.

In this connection, crystals of salt of a stereoisomer, which is a non-natural type of monatin, which are applicable as a sweet taste substance, are newly provided. The crystals are stable, have a high degree of sweet taste (high sweetening potency) and are expected for use as a sweetener or an ingredient thereof and also as a component for giving sweet taste to beverage, food, etc.

A sweetener using the above-mentioned crystals of the salt, which is a novel sweet taste substance and a product such as beverage, and food to which sweet taste is given can be provided.

The stereoisomer salt includes salts of a (2S,4R) substance, a (2R,4R) substance and a (2R,4S) monatin substance and the salt of a (2R,4R) monatin substance is particularly preferred.

The natural-type monatin has a (2S,4S) steric structure while, in the present invention, all compounds having the same chemical structure formula are called "monatin" and, therefore, the non-natural stereoisomers of monatin are called "stereoisomer of the natural-type monatin", "non-natural monatin", "(2S,4R) monatin substance", "(2R,4S) monatin substance" or "(2R,4R) monatin substance", etc. Further, monatin (a (2S,4S) substance) is added to such stereoisomers and they are called "four kinds of stereoisomers" and, particularly, the natural-type monatin is called "monatin", "monatin (a (2S,4S) substance)" or "a (2S,4S) monatin substance", etc.

In order to solve the above-mentioned problems, the present inventors have performed intensive investigations for monatin. First, according to a method by K. Nakamura, et al., stereoisomers (a mixture of isomers) of a (2S,4S) monatin substance with a (2S,4R) monatin substance and those of a (2R,4R) monatin substance with a (2R,4S) monatin substance were synthesized and, from those stereoisomer mixtures, the desired stereoisomer was separated and prepared by means of a reversed phase HPLC (high-performance liquid chromatography). A stereoisomer prepared by such a method was also crystallized as a salt with various kinds of bases by a method (below) whereby crystals of higher purity were able to be prepared. Optical purity the isolated stereoisomers were subsequently confirmed by means of an optically active column HPLC method. Further, intensity of sweet taste of the resulting four kinds of stereoisomers of monatin was measured and determined using sucrose as a standard solution.

As a result, it has been found that the intensity of the sweet taste of the natural-type monatin (a (2S,4S) substance) is far lower than the data which were reported already, that all of other non-natural-type stereoisomers have stronger intensity of sweet taste than monatin (a (2S,4S) substance) and that some of them show far better intensity of sweet taste as compared with the (2S,4S) substance and are excellent as sweeteners.

Thus, it has been newly found that a (2R,4S) monatin substance and a (2R,4R) monatin substance show about 1300-fold and about 2700-fold intensity of sweet taste, respectively, as compared with a 5% aqueous solution of sucrose and that, among the non-natural-type stereoisomers, the (2R) substances are particularly excellent as sweeteners.

A method where a mixture of stereoisomers of monatin prepared by the above synthetic method, a method where the mixture is crystallized as salts with various bases, a method where the mixture is crystallized as derivatives, a method where the derivative is separated by means of an optical isomer separation column, etc. were investigated and the present inventors also succeeded in preparing each stereoisomer as an optically pure substance by those methods as well.

The present inventors have discovered various crystallizing conditions for each stereoisomer and a mixture thereof prepared as such, succeeded in preparing crystals of various salts for the first time and been able to measure various physical property data such as intensity of sweet taste. It has been determined that crystals of those salts with bases which have been firstly prepared at this time, particularly, crystals of non-natural stereoisomer salts of monatin have excellent properties in view of easiness in separation/purification, stability in the crystalline state, etc. as compared with conventionally known crystals of free compounds such as a (2S,4S) substance mentioned in the report by R. Vleggaar, et al. and amorphous substances of various salts which were known only as amorphous solid by the patent document of P. J. van Wyk, et al.

Potassium salt of a (2R,4R) monatin substance having a particularly strong intensity of sweet taste is excellent as the most practical product form in such views that an organic solvent used for crystallization is not contained as an adhered solvent (such as an alcohol of crystallization), that stability upon heating is excellent, that the product is hardly colored as compared with a free compound where crystallization is conducted under an acidic condition, etc.

It has been further discovered that sweeteners, beverages/foods, etc. can be provided using the crystals of non-natural-type stereoisomer salts of monatin.

The present invention has been achieved on the basis of various findings as mentioned above.

As such, in accordance with the present invention, separation and purification of monatin (a (2S,4S) substance) which is a natural stereoisomer, and separation and purification of four kinds of stereoisomers (optical isomers) having the same chemical structural formula including that and confirmation of their optical purities have been performed for the first time.

At the same time, more correct sweetness intensity of all of stereoisomers (four kinds) of monatin has been assessed. As a result, it has been found that novel crystals of the non-natural stereoisomer salts of monatin are excellent, sweet taste substances (sweeteners) and also are a practical product form as sweet taste substances (sweeteners) as compared with the conventionally prepared crystals of free compounds such as a (2S,4S) substance and amorphous solid of salts mentioned in the prior art. It has been also confirmed that crystals of a salt of a (2R,4R) monatin substance have the strongest sweetness intensity among the four stereoisomers, which could not have been predicted from the prior art and that they are most suitable as sweeteners or ingredients therefor which are subjected to a practical application.

Thus, as an embodiment, the present invention relates to crystals of salt of non-natural stereoisomer of monatin. The present invention relates to crystals of salt of non-natural stereoisomer of monatin which is a sweetener (sweet taste substance) of an amino acid type and the stereoisomer salt includes at least one member of salt of a (2R,4R) substance, salt of a (2R,4S) substance and salt of a (2S,4R) monatin substance.

In the present invention, a compound that constitutes the crystals of the stereoisomer salt is a salt of the above-mentioned non-natural-type stereoisomer and it may be in a form of hydrate, solvate, etc. thereof. Further, the compound may be in a form of lactone or lactam of such a monatin salt cyclized in a molecule and/or in a form where at least one of functional groups contained therein is protected.

There is no particular limitation for type, form, etc. of the salt contained in the crystals of the present invention. When they are used for food as the final product, it goes without saying that a salt that can be used as food is adopted. In addition to the above, salt that is suitable as an intermediate is also useful. Such a thing (the above-mentioned form of the crystals and type, form, etc. of the salt) is not only applied to the case of the form of non-natural-type stereoisomer salt (crystals) of monatin but also similarly applied to that of the form of natural-type stereoisomer salt (crystals) of monatin when used by mixing which will be mentioned later.

The form of such a salt includes, for example, a salt with alkaline metal such as lithium, sodium and potassium, a salt with alkaline earth metal such as calcium and magnesium, an ammonium salt with ammonia, etc., a salt with amino acid such as lysine and arginine, a salt with inorganic acid such as hydrochloric acid and sulfuric acid, a salt with organic acid such as citric acid and acetic acid and a salt with other sweetener or a component thereof such as saccharin, acesulfame, cyclamic acid, glycyrrhizic acid and aspartame and such a thing is also applicable, as mentioned above, to a salt of the stereoisomer used in the present invention and to a salt of a natural-type monatin when used.

With regard to a method for the production of the above salt, a desired salt may be prepared on the basis of the explanation (such as Examples) for the present invention utilizing, if necessary, commonly used or publicly-known method for the production of salts.

The above-mentioned stereoisomer including the natural-type monatin when used contains functional groups such as carboxyl group, hydroxyl group, amino group and indolyl (indole) group and such a functional group may be protected. With regard to the protecting group, it is possible to use a protecting group that is commonly used in organic chemistry, particularly in amino acid and peptide chemistry as a protecting group for each of them.

The crystals of the present invention include the following properties [1] to [6].

[1] With regard to the non-natural-type stereoisomer salt, salt of a (2S,4R) substance, salt of a (2R,4R) substance and salt of a (2R,4S) substance of monatin are listed. Crystals of the salt may be in a form of a hydrate or a solvate or the like.

Among those stereoisomer salts, a (2R,4S) substance and a (2R,4R) substance of monatin are more preferred and a (2R,4R) substance of monatin is most preferred. Crystals of the salt as such covered by the present invention are preferred because of their easiness in isolation and purification and excellence in stability upon preservation.

[2] The above-mentioned crystals of the non-natural-type stereoisomer salt of the present invention may have the salt of the stereoisomer (including the form of hydrate, solvate, etc.) preferably at least about 95% or, more preferably, at least about 97% of chemical purity.

[3] The above-mentioned crystals of the non-natural-type stereoisomer salt of the present invention may have preferably at least about 90%, more preferably at least about 94% and, still more preferably at least about 98% of optical purity. For example, a highly optically pure product of salt of a (2R,4R) substance of monatin (including the form of hydrate, solvate and a mixture of the salts) may be listed.

[4] With regard to the above-mentioned crystals of stereoisomer salt of the present invention, crystals of a mixture of at least two members selected from stereoisomer salts of a (2S,4R) substance, a (2R,4R) substance and a (2R,4S) substance of monatin may be adopted.

[5] With regard to the above-mentioned crystals of non-natural-type stereoisomer salt of the present invention, those having sweetness intensity of preferably at least about 200-fold or, more preferably, at least about 1000-fold of that of sucrose in a practical concentration of 5-10% may be adopted.

[6] The above-mentioned crystals of the stereoisomer salt of the present invention may be used in a mixed form with crystals of salt of a natural-type monatin (a (2S,4S) substance). In that case, a (2S,4S) substance of the monatin may be contained preferably in not more than about 70% or, more preferably, in not more than about 50% in the total monatin.

Incidentally, a (2S,4S) substance which is a natural-type monatin and a (2S,4R) substance, a (2R,4R) substance and a (2R,4S) substance which are non-natural-type monatins are represented by the following structural formulae (1), (2), (3) and (4), respectively.

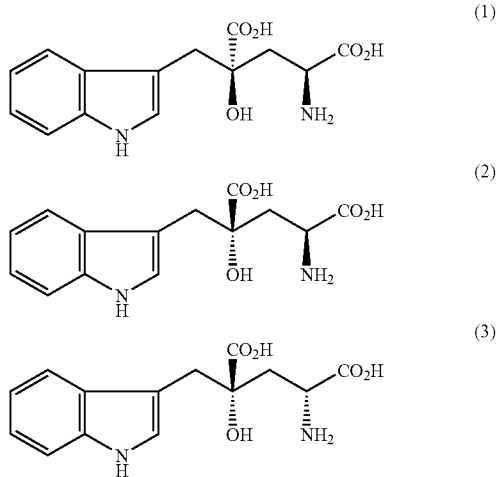

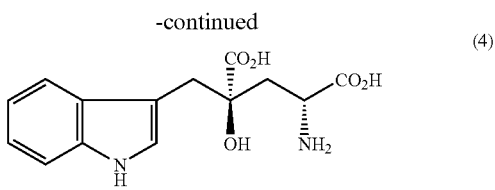

(4)

Monatin of (2S) substances (a mixture of a (2S,4S) substance and a (2S,4R) monatin substance), monatin of (2R) substances (a mixture of a (2R,4R) substance and a (2R,4S) monatin substance) and a mixture of the four stereoisomers can be synthesized according to the method of K. Nakamura, et al. and each stereoisomer can be separated therefrom. With regard to a synthetic method for monatin containing various stereoisomers, other methods may be adopted and it is not limited to the above-mentioned method by K. Nakamura, et al.

Hereinafter, examples for the case where each stereoisomer is separated and purified from monatin containing various stereoisomers will be briefly illustrated. They are illustrated as examples and the present invention is not limited to those examples.

With regard to stereoisomers of monatin of (2S) substances and monatin of (2R) substances synthesized according to a method by K. Nakamura, et al., they can be separated and prepared by means of a reversed phase HPLC but a method for resolving the stereoisomers of monatin is not limited thereto.

It is also possible that the four stereoisomers synthesized by the already-reported method, etc. are separated to give each stereoisomer. For example, it is possible to use a method where the four stereoisomers of monatin are crystallized as a salt or a derivative and a method where the derivatives are separated by a column of separation of optical isomers and the resulting isomer is returned to monatin again although the resolving method for the stereoisomers is not limited thereto.

The component that constitutes the crystals of the present invention is the above-mentioned monatin salt and, as mentioned above, it is also possible to use in other forms such as a lactone derivative or a lactam derivative thereof. For example, in forming a lactone or lactam derivative where cyclization takes place in a molecule in the monatin salt, that can be performed by utilizing a method which has been known as a method for forming lactone or lactam being cyclized in a molecule. Further, in the case of formation of a derivative where at least one of functional groups is protected, it is also possible to do that by utilizing a method that has been known as a method for protection of functional group.

Optical purity of the crystals of each stereoisomer obtained can be determined by means of an optical activity column HPLC method, but a method for determination of optical purity is not limited thereto.

Intensity of sweet taste (sweetening potency; degree of sweet taste) of the crystals of each stereoisomer obtained can be determined by comparing with a 5% aqueous solution of sucrose, but a method for the determination of intensity of sweet taste is not limited thereto.

Tables 1 and 2 summarize the relationship between the structure of each stereoisomer and the intensity of sweet taste or the optical purity. Tables 1 and 2 provide the results evaluated for the samples that are prepared by means of an HPLC, purified by ion-exchange resin and freeze-dried as an ammonium salt, and for those that are crystallized and purified as a sodium salt, respectively.

TABLE 1

| Stereoisomers | Sweetness Intensity[1] | Optical Purity[2] |
|---|---|---|
| (2S, 4S) | ca. 300 | 94 |
| (2S, 4R) | ca. 300 | 94 |
| (2R, 4R) | ca. 2000 | 94 |
| (2R, 4S) | ca. 800 | 96 |

[1]The data as compared with a 5% aqueous solution of sucrose.
[2]Most of other stereoisomers contained were enantiomers.

TABLE 2

| Stereoisomers | Sweetness Intensity[1] | Optical Purity |
|---|---|---|
| (2S, 4S) | ca. 50 | 99.8 |
| (2S, 4R) | ca. 300 | 99.4 |
| (2R, 4R) | ca. 2700 | 99.3 |
| (2R, 4S) | ca. 1300 | 99.2 |

[1]The data as compared with a 5% aqueous solution of sucrose.

As is evident from Table 2, the sweetness intensity of monatin present in nature (the natural one) (a (2S,4S) substance) is about 50-fold and is lower than the already-reported data. Interestingly, the other three stereoisomers of monatin possess higher sweetness intensity than monatin (a (2S,4S) substance) and, particularly, a (2R,4R) monatin substance shows the strongest sweetness intensity of as high as about 2700-fold.

It should be noted that in preferred embodiment of the present invention the isolated crystalline form of monatin (i.e., non-natural monatin) is at a chemical purity of at least 95%, more preferably at least 97.5%.

It should also be noted that in preferred embodiment of the present invention the isolated crystalline form of monatin (i.e., non-natural monatin) is at an optical purity of at least 94%, more preferably at least 96%, and most preferably at least 99%.

From various stereoisomers that are separated by chromatography, etc. or prepared by a synthetic method, etc., it is possible to separate a salt of each stereoisomer as crystals of a high purity by means of further crystallization.

In the comparison of the results of evaluation as shown in the above Tables 1 and 2, purity including optical purity is improved by crystallization for the (2R) substances whereby the utility by making into salt crystals is shown.

Incidentally, when the crystals of the non-natural stereoisomer salt of the present invention (including hydrate, solvate, etc.) (the stereoisomer includes a form of lactone or lactam where cyclization takes place in a molecule, a form where at least one of the contained functional groups is protected, etc.) are used as a sweetener, it goes without saying that they may be used together with other sweetener(s) unless there is any particular inconvenience.

When crystals of the stereoisomer salt of the present invention (including hydrate, solvate, etc.) are used as a sweetener, it is possible to use a carrier and/or a filler (bulking agent) if necessary. For example, it is possible to use a carrier, a filler, etc. which have been known or used for sweeteners already.

Although crystals of stereoisomer salt of the present invention (including hydrate, solvate, etc.) may be used as a sweetener or a component for a sweetener, it is also possible that the crystals may be used as a sweetener or a sweet taste ingredient by compounding with the products such as beverage and food. Examples of beverages and foods envisaged by the present invention confectionery, chewing gum, sanitary product, cosmetics, drugs and also with products for animals except humans. It is further possible that crystals of the non-natural stereoisomer salt are used as a form of a product to which sweet taste is given by containing or using the non-natural stereoisomer salt crystals of the present invention or as a sweetness-giving component in a method for giving sweet taste to the product which is needed to be given with a sweet taste. With regard to a method for using them, etc., that may be conducted by a conventional method that has been commonly used as a method for using or producing a sweetener or by other known method.

A compound that constitutes the crystals of the natural-type monatin salt is a salt of a natural-type monatin and it is also possible to use in a form of hydrate, solvate, etc. thereof. It is still also possible that the compound is used as a salt of monatin as such in a form of lactone or lactam where cyclization takes place in a molecule and/or in a form where at least one of the functional groups contained therein is protected.

Even in that case, it is possible to prepare the aimed mixture crystals in preferably at least about 200-fold or, more preferably, at least about 1000-fold of sucrose of the above-mentioned practical concentration in terms of sweetness intensity of the mixture crystals in a state of crystals of salt including the natural-type stereoisomer.

With regard to the preferred examples of the above-mentioned ones, crystals of a mixture of salts of a (2S,4S) substance of monatin with a (2R,4R) substance of monatin or, particularly, crystals of a mixture of a (2S,4S) substance salt of monatin with a (2R,4R) substance salt of monatin in a ratio (by weight) of about 1:0.5-2 or, particularly, preferably about 1:1 may be exemplified.

As another embodiment, the present invention also relates to a sweetener that contains the above-mentioned crystals of the non-natural-type stereoisomer salts of the present invention.

The sweetener may further contain a carrier and/or a filler (bulking agent), etc. for sweeteners.

Moreover, the sweetener may also contain a carrier or a filler that is commonly used for sweeteners or will be developed for such a purpose. It is also, of course, possible for the sweetener to contain an additive which that is compatible with the sweeteners. The sweetener is used for animals such as mammals, particularly for humans.

As still another embodiment, the present invention also relates to a product such as beverage and food to which sweet taste is bestowed by the addition of the above-mentioned crystals of salt of non-natural-type stereoisomer of the present invention.

The crystals may be used at least as a part of a sweetener for products for animals, particularly for beverages and foods for humans to which sweet taste is requested. Besides the above, the crystals may be also used for the purpose of oral hygiene such as dentifrice and drugs or for orally-used products with the purpose of giving sweet taste.

The above-mentioned products such as sweetener and beverage/food according to the present invention may also contain at least one member (one compound) selected from other sweetener components (sweetening agents), particularly saccharides and other artificial and natural sweeteners. For example, sucrose, aspartame, acesulfame, sucralose, saccharin, stevioside, xylose, trehalose, sorbitol, maltitol and the like may be used together.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Materials and Methods—

$^1$H-NMR spectra were measured using a Bruker Avance 400 (400 MHz) and MS spectra were measured using a Thermo Quest TSQ 700. The cation-exchange resins employed herein were Amberlite IR120B H AG and Diaion PK 228. To measure the powder X-ray diffraction a PW 3050 instrument manufactured by Phillips was used. The melting point measurements were performed using Micro Melting Point Apparatus from Yanaco. The optical rotary power measurements were performed using a DIP-370 Digital Polarimeter manufactured by Nippon Bunko (Jasco Engineering).

Example 1

Monatin was synthesized according to a method described by K. Nakamura, et al. (cf. K. Nakamura, et al., Organic Letters, 2, 2967-2970 (2000)), adsorbed with a cation-exchange resin (H$^+$ type) and subjected to purification by means of elution with a 3% aqueous ammonia solution. Subsequent freeze-drying resulted in 2.92 g of ammonium salts of monatin of (2S) substances (a mixture of a (2S,4S) substance and a (2S,4R) monatin substance) and 711 mg of ammonium salts of monatin of (2R) substances (a mixture of a (2R,4R) substance and a (2R,4S) monatin substance).

Resolution of 660 mg of monatin of (2S) substances and 711 mg of monatin of (2R) substances respectively was performed according to the following preparative condition to give 207 mg of a (2S,4S) monatin substance, 233 mg of a (2S,4R) monatin substance, 261 mg of a (2R,4R) monatin substance and 254 mg of a (2R,4S) monatin substance as amorphous solid in a form of ammonium salts.

Preparative Conditions:

Guard column: Inertsil ODS-3 30×50 mm;

Column: Inertsil ODS-3 30×250 mm;

Detection: UV 210 nm;

Eluent: <A> acetonitrile 0.05% TFA, <B> H$_2$O 0.05% TFA;

Flow rate: 28 ml/min;

Gradient: 12% to 18% of <A> within 25 minutes;

Loaded amount: 10-13 mg; and

Temperature upon working: 25° C.
Treatment After the Preparation:

The preparation fraction was neutralized with aqueous ammonia and concentrated. The preparation fractions were combined, concentrated and adsorbed with a cation-exchange resin (Amberlite IR 120B H AG; H+ type). This was then eluted with a 5% aqueous ammonia solution and the eluted fraction was freeze-dried.

Optical purity (enantiomer purity) of each stereoisomer was tested by the following analytical conditions.

Analytical Conditions
Column: Crownpak CR(+) 4×150 mm;
Detection: UV 210 nm;
Eluent: Aqueous perchloric acid (pH 2.0)/methanol=90/10;
Flow rate: 1.2 ml/min; and
Temperature for analysis: 25° C.
Optical Purity:

Data in parentheses show the eluting time for each peak. Results are given for each stereoisomer.
(2S,4S) monatin substance: 94% (45.0 min);
(2S,4R) monatin substance: 94% (26.1 min);
(2R,4R) monatin substance: 94% (20.9 min); and
(2R,4S) monatin substance: 96% (16.1 min).

The primary impurity contained in each stereoisomer was an enantiomer thereof. For example, a (2S,4S) monatin substance contained a small amount of a (2R,4R) monatin substance.

"Sweet taste" intensity of each stereoisomer obtained was measured by the following method.

A 0.05% aqueous solution of each stereoisomer was prepared and diluted to an appropriate extent to prepare an aqueous solution of a sample of a predetermined concentration. Separately, a 5% aqueous solution of sucrose was prepared and used as a standard solution. The diluted aqueous solution of the sample and the standard aqueous sucrose solution were tasted one after another and the sweetness rate was determined from the sample concentration where the intensities of sweetness were noted to be same. Seven panelists performed the evaluation.

Intensity of the sweet taste for each stereoisomer was decided to be as follows.
(2S,4S) monatin substance: about 300-fold;
(2S,4R) monatin substance: about 300-fold;
(2R,4R) monatin substance: about 2000-fold; and
(2R,4S) monatin substance: about 800-fold.

Result of measurement of optical rotary power ($[\alpha]_D^{25}$ (c=0.5)) for each stereoisomer was as follows.
(2S,4S) monatin substance: −44.1 ($H_2O$), −7.5 (3% aqueous ammonia);
(2S,4R) monatin substance: −7.8 ($H_2O$);
(2R,4R) monatin substance: +3.7 ($H_2O$), +8.7 (3% aqueous ammonia); and
(2R,4S) monatin substance: +11.1 ($H_2O$).

$^1$H-NMR of each stereoisomer was as follows (400 MHz, $D_2O$).

Ammonium salts of (2S,4S) substance and (2R,4R) monatin substance: 1.96 (1H, dd, J=11.8 Hz), J=15.2 Hz), 2.57 (1H, dd, J=1.9 Hz, J=15.2 Hz), 3.00 (1H, d, J=14.6 Hz), 3.20 (1H, d, J=14.6 Hz), 3.54 (1H, d, J=10.2 Hz), 7.04 (1H, t, J=7.2 Hz), 7.10 (1H, t, J=7.2 Hz), 7.10 (1H, s), 7.38 (1H, d, J=8.0 Hz), 7.62 (1H, d, J=8.0 Hz).

Ammonium salts of (2S,4R) substance and (2R,4S) monatin substance: 2.11 (1H, dd, J=10.4 Hz, J=15.0 Hz), 2.37 (1H, d, J=15.4 Hz), 3.13 (2H, s), 3.88 (1H, d, J=9.8 Hz), 7.05 (1H, d, J=7.6 Hz), 7.14 (2H, s), 7.38 (1H, d, J=7.9 Hz), 7.63 (1H, d, J=7.9 Hz).

MS spectrum of each stereoisomer was as follows.
ESI-MS: 291 (M−H)−.

Example 2

Resolution of a Mixture of Ammonium Salts of Four Stereoisomers of Monatin into Racemic Crystals of a (2S,4S) Substance and a (2R,4R) Substance and Racemic Crystals of a (2S,4R) Substance and a (2R,4S) Substance.

Ammonium salts (10.00 g; 32.33 mmol) of a mixture of steric (optical) isomers of monatin (monatin [(2S,4S)+(2R,4R) substances]: monatin [(2S,4R)+(2R,4S) substances]=6:4) were dissolved in 100 ml of a 2.5% aqueous ammonia solution and the resulting solution was concentrated to an extent of 20 ml. Newly, 3 ml of a 5% aqueous ammonia solution were added thereto and the mixture was homogenized and allowed to stand at room temperature for 30 minutes. After the crystals were separated out (produced), a slurry was formed from this mixture by addition of 80 ml of an aqueous solution comprising a 5% aqueous ammonia solution and ethanol (25/75) and crystals of ammonium salts of (2S,4S) and (2R,4R) monatin substances were filtered. The resulting crystals were dissolved in 30 ml of a 2.5% aqueous ammonia solution once again, concentrated and recrystallized from 0.5 ml of a 5% aqueous ammonia solution and 30 ml of ethanol to give 4.80 g (15.52 mmol; reversed phase HPLC purity (hereinafter, referred to as "HPLC purity"): 98.0%) of crystals of ammonium salts of (2S,4S) and (2R,4R) monatin substances.

$^1$H-NMR ($D_2O$) δ: 1.95-2.02 (m, 1H), 2.58-2.62 (m, 1H), 3.01-3.05 (m, 1H), 3.21-3.24 (m, 1H), 3.55-3.58 (m, 1H), 7.07-7.11 (m, 1H), 7.14-7.18 (m, 2H), 7.42-7.44 (d, 1H), 7.66-7.68 (d, 1H).

ESI-MS: 291.39 (M−H)−.
Melting point: 182-186° C.
Degree of sweet taste: about 1300-fold (as compared with a 5% aqueous solution of sucrose).

FIG. 17 shows an optical microphotograph (magnification: 200-power) after drying of ammonium salt crystals of [(2S,4S)+(2R,4R)] monatin substances.

FIG. 18 is a powder X-ray diffraction chart after drying of ammonium salt crystals of [(2S,4S)+(2R,4R)] monatin substances. Characteristic diffraction X-ray peaks were noted at the angles of diffraction (2θ, CuKα line) of 6.0°, 12.1°, 15.2°, 18.6°, 21.3°, 23.2° and 25.0°.

The filtrate ([(2S,4S)+(2R,4R) monatin substances]: [(2S,4R)+(2R,4S) monatin substances]=3:10) obtained in the above operation was concentrated to an extent of 5 ml. Newly, 3 ml of a 5% aqueous ammonia solution were added thereto and the mixture was homogenized and allowed to stand at room temperature for 10 minutes. After the crystals were separated out, a slurry was formed from this mixture by addition of 80 ml of ethanol and crystals of ammonium salts of [(2S,4R)+(2R,4S) monatin substances] were filtered. The resulting crystals were dissolved in 30 ml of a 2.5% aqueous ammonia solution once again, concentrated and recrystallized for three times from 0.5 ml of a 5% aqueous ammonia solution and 30 ml of ethanol to give 3.10 g (10.02 mmol; HPLC purity: 98.2%) of crystals of ammonium salts of [(2S,4R)+(2R,4S) monatin substances]. The overall recovery rate was 79.0%.

$^1$H-NMR ($D_2O$) δ: 2.11-2.17 (m, 1H), 2.38-2.43 (m, 1H), 3.16 (s, 2H), 3.90-3.93 (m, 1H), 7.06-7.10 (m, 1H), 7.13-7.17 (m, 2H), 7.41-7.43 (d, 1H), 7.66-7.68 (d, 1H).

ESI-MS: 291.19 (M−H)−.
Melting point: 167.2-168.4° C.

Degree of sweet taste: about 800-fold (as compared with a 5% aqueous solution of sucrose).

FIG. 19 shows an optical microphotograph (magnification: 200-power) after drying of ammonium salt crystals of [(2S,4R)+(2R,4S)] monatin substances.

FIG. 20 is a powder X-ray diffraction chart after drying of ammonium salt crystals of [(2S,4R)+(2R,4S)] monatin substances. Characteristic diffraction X-ray peaks were noted at angles of diffraction (2θ, CuKα line) of 5.4°, 10.2°, 19.7°, 21.0° and 21.8°.

Example 3

Preparation of Crystals of Sodium Salts of Racemic Compounds (or a Racemic Mixture) Comprising (2S,4S) and (2R,4R) Monatin Substances.

Ammonium salts (1.00 g; 3.23 mmol; HPLC purity: 100%) of [(2S,4S)+(2R,4R)] monatin substances were dissolved in 10 ml of water, an aqueous solution of sodium hydroxide (20 equivalents) was added thereto and the mixture was concentrated. An operation of addition of 20 ml of water followed by concentrating was repeated for three times, then the concentrate was dissolved in 20 ml of water again and ion-exchange resin (Amberlite IR 120B H AG (H+)) was added to make the solution weakly alkaline followed by stirring to remove excess sodium. After the resin was filtered off, the filtrate was concentrated in vacuo. The concentrate was crystallized using a 95% aqueous solution of ethanol at room temperature to give 0.680 g (2.14 mmol) of crystals of a solvate of sodium salt of [(2S,4S)+(2R,4R)] monatin substances with 0.05 molar equivalent of ethanol in a yield of 66.3%.

$^1$H-NMR (D$_2$O) δ: the same as those in Example 2.

ESI-MS: 291.19 (M−H)$^-$.

Melting point: 201.7-203.2° C.

FIG. 21 shows an optical microphotograph (magnification: 200-power) after drying of sodium salt crystals of [(2S,4S)+(2R,4R)] monatin substances.

FIG. 22 is a powder X-ray diffraction chart after drying of sodium salt crystals of [(2S,4S)+(2R,4R)] monatin substances. Characteristic diffraction X-ray peaks were noted at the angles of diffraction (2θ, CuKα line) of 4.4°, 13.6°, 15.2°, 16.7°, 22.2° and 24.4°.

Example 4

Preparation of Crystals of Potassium Salts of Racemic Compounds (or a Racemic Mixture) Comprising (2S,4S) and (2R,4R) Monatin Substances.

The same operation as in Example 3 was performed with the exception that an aqueous solution of potassium hydroxide was used in place of an aqueous solution of sodium hydroxide to give 0.71 g (2.13 mmol) of crystals of a solvate of potassium salt of [(2S,4S)+(2R,4R)] monatin substances with 0.05 molar equivalent of ethanol in a yield of 65.9%.

$^1$H-NMR (D$_2$O) δ: the same as those in Example 2.

ESI-MS: 291.49 (M−H)$^-$.

Melting point: 223.8-224.7° C.

FIG. 23 shows an optical microphotograph (magnification: 200-power) after drying of potassium salt crystals of [(2S,4S)+(2R,4R)] monatin substances.

FIG. 24 is a powder X-ray diffraction chart after drying of potassium salt crystals of [(2S,4S)+(2R,4R)] monatin substances. Characteristic diffraction X-ray peaks were noted at the angles of diffraction (2θ, CuKα line) of 5.9°, 18.7°, 20.1° and 23.8°.

Example 5

Preparation of Z-lactone (2-benzyloxycarbonylamino-4-(3-indolylmethyl)-4-carboxy-γ-butyrolactone) of a Racemic Compound (or a Racemic Mixture) of (2S,4S) Substance with (2R,4R) Monatin Substance.

An ammonium salt (19.51 g; 63.07 mmol; HPLC purity: 99.2%) of [(2S,4S)+(2R,4R) substances] of monatin was dissolved in 94.6 ml of a 2N aqueous solution of sodium hydroxide (189.2 mmol) and 90 ml of water. Benzyloxycarbonyl chloride (12.61 ml; 88.30 mmol) was added followed by stirring for 2 hours at room temperature and then 15.8 ml (31.54 mmol) of a 2N aqueous solution of sodium hydroxide and 4.50 ml (31.54 mmol) of benzyloxycarbonyl chloride were added followed by stirring for one night at room temperature. The resulting aqueous reaction solution was subjected to an extracting operation with 50 ml of ether for three times to remove an excessive benzyloxycarbonyl chloride. The reaction solution was adjusted to pH 3 by hydrochloric acid and subjected to an extracting operation with 100 ml of ethyl acetate for three times and the organic layer was dried over anhydrous magnesium sulfate. Magnesium sulfate was removed by filtration and the filtrate was concentrated in vacuo to give 27.93 g (65.50 mmol) of Z-monatin (2-benzyloxycarbonylamino-4-hydroxy-4-carboxy-5-(3-indolyl)pentanoic acid), [(2S,4S)+(2R,4R)] substances. The Z-monatin [(2S,4S)+(2R,4R)] substances (27.93 g; 65.50 mmol) was dissolved in 400 ml of ethyl acetate and heated at 75° C. for 3 hours after addition of 1.25 g (6.55 mmol) of p-toluenesulfonic acid thereto. The resulting reaction solution was washed with water and a saturated saline solution and dried over anhydrous magnesium sulfate. The magnesium sulfate was removed by filtration and the filtrate was concentrated in vacuo. To the residue were added 100 ml of chloroform and the crystals separated out therefrom were collected by filtration to give 17.64 g (43.19 mmol; HPLC purity: 99.6%) of Z-lactone [(2S,4S)+(2R,4R)] substances in an overall yield of 68.5%.

$^1$H-NMR (DMSO-d$_6$) δ: 2.36-2.42 (m, 1H), 2.64-2.70 (m, 1H), 3.24-3.41 (m, 2H), 3.71-3.81 (m, 1H), 4.98 (s, 2H), 6.97-7.00 (m, 1H), 7.04-7.09 (m, 1H), 7.21 (s, 1H), 7.30-7.33 (m, 5H), 7.54-7.56 (d, 1H), 7.66-7.69 (d, 1H), 11.03 (s, 1H).

ESI-MS: 409.68 (M+H)$^+$.

Melting point: 195.5-196.9° C.

Example 6

Preparation of Z-lactone (2-benzyloxycarbonylamino-4-(3-indolylmethyl)-4-carboxy-γ-butyrolactone) of a Racemic Compound (or a Racemic Mixture) of a (2S,4R) Substance with a (2R,4S) Monatin Substance.

The same operation as in Example 5 was performed with the exception that 15.00 g (48.49 mmol; HPLC purity: 99.5%) of ammonium salt of [(2S,4R)+(2R,4S)] monatin substances was used in place of ammonium salt of [(2S,4S)+(2R,4R)] monatin substances and that heating was performed at 75° C. for 2 hours after addition of p-toluenesulfonic acid to give 12.10 g (29.64 mmol; HPLC purity: 100%) of the Z-lactone [(2S,4R)+(2R,4S)] substances in an overall yield of 61.1%.

$^1$H-NMR (DMSO-d$_6$) δ: 2.31-2.37 (m, 1H), 2.71-2.76 (m, 1H), 3.19-3.23 (m, 1H), 3.43-3.47 (m, 1H), 4.34-4.41 (m, 1H), 5.05 (s, 1H), 6.96-7.00 (m, 1H), 7.04-7.08 (m, 1H), 7.14 (s, 1H), 7.32-7.37 (m, 5H), 7.53-7.55 (d, 1H), 7.85-7.87 (d, 1H), 10.95 (s, 1H).

ESI-MS: 409.58 (M+H)$^+$.

Melting point: 156.7-159.1° C.

Example 7

Resolution into Z-lactone (2S,4S) Substance and Z-lactone (2R,4R) Substance.

Resolution by an optical isomer resolution column was performed with 1.17 g (2.86 mmol; HPLC purity: 99.7%) Z-lactone [(2S,4S)+(2R,4R)] substances. At that time, CHIRALPAK AS (20×50 mm) and CHIRALPAK AS (20×250 mm) were used as a guard column and a preparative column, respectively. The preparation was performed with an eluent of hexane/ethanol/acetic acid (40/60/0.5), flow rate was 10 ml/minute, detection was by UV 210 nm, temperature was 40° C. and loaded amount was 25 mg. Time for the elution was 13 minutes for Z-lactone (2S,4S) substances and 23 minutes for Z-lactone (2R,4R) substances, respectively. Each preparative fraction was concentrated, dissolved in 50 ml of ethyl acetate and concentrated again. The residue was crystallized from 30 ml of chloroform to give 428 mg (1.05 mmol) of Z-lactone (2S,4S) substance and 399 mg (0.977 mmol) of Z-lactone (2R,4R) substance (an overall recovery yield: 70.7%).

Z-lactone (2S,4S) Substance $^1$H-NMR (DMSO-$d_6$) δ: the same as those in Example 5.

ESI-MS: 409.68 (M+H)$^+$.

Melting point: 179.8-182.0° C.

Z-lactone (2R,4R) Substance $^1$H-NMR (DMSO-$d_6$) δ: the same as those in Example 5.

ESI-MS: 409.88 (M+H)$^+$.

Melting point: 179.2-182.8° C.

Example 8

Resolution into Z-lactone (2S,4R) Substance and Z-lactone (2R,4S) Substance.

Resolution by an optical isomer resolution column was performed with 9.89 g (24.22 mmol; HPLC purity: 100%) Z-lactone [(2S,4R)+(2R,4S)] substances. At that time, CHIRALCEL OJ (20×50 mm) and CHIRALCEL OJ (20×250 mm) were used as a guard column and a preparative column, respectively. The preparation was performed with an eluent of hexane/ethanol/trifluoroacetic acid (40/60/0.1), flow rate was 8 ml/minute, detection was by UV 210 nm, temperature was 40° C. and loaded amount was 50 mg. Time for the elution was 16 minutes for Z-lactone (2R,4S) substances and 21 minutes for Z-lactone (2S,4R) substances, respectively. Each preparative fraction was concentrated after being neutralized with aqueous ammonia. The concentrate was dissolved in 150 ml of ethyl acetate, washed with an aqueous solution of hydrochloric acid adjusted to pH 3, then washed with a saturated saline solution and dried over anhydrous magnesium sulfate. The magnesium sulfate was removed by filtration and the filtrate was concentrated in vacuo. The residue was crystallized with 100 ml of hexane to give 4.88 g (11.45 mmol; HPLC purity: 97.3%) of a solvate of Z-lactone (2R,4S) substance with 0.2 molar equivalent of ethyl acetate and 5.41 g (12.70 mmol; HPLC purity: 96.9%) of a solvate of Z-lactone (2S,4R) substance with 0.2 molar equivalent of ethyl acetate (an overall recovery yield: 99.7%).

Solvate of Z-lactone (2R,4S) Substance with 0.2 Molar Equivalent of ethyl acetate $^1$H-NMR (DMSO-$d_6$) δ: 2.21-2.28 (m, 1H), 2.64-2.70 (m, 1H), 3.18-3.22 (m, 1H), 3.40-3.44 (m, 1H), 4.42-4.45 (m, 1H), 5.04 (s, 2H), 6.95-7.00 (m, 1H), 7.03-7.07 (m, 1H), 7.15 (s, 1H), 7.32-7.35 (m, 5H), 7.52-7.55 (d, 1H), 7.80-7.82 (d, 1H), 10.92 (s, 1H).

ESI-MS: 409.58 (M+H)$^+$.

Melting point: 109.1-110.8° C.

Solvate of Z-lactone (2S,4R) substance with 0.2 molar equivalent of ethyl acetate $^1$H-NMR (DMSO-$d_6$) δ: the same as those in above-mentioned (2R,4S) substance.

ESI-MS: 409.58 (M+H)$^+$.

Melting point: 116.1-116.8° C.

Example 9

Conversion of Z-lactone (2R,4R) Substance into Sodium Salt Crystals of Monatin (2R,4R) Substance (Preparation of Crystals of Sodium Salt. No. 1)

A Z-lactone (2R,4R) substance (14.24 g; 34.85 mmol; HPLC purity: 99.5%) was dissolved in 400 ml of methanol and 40 ml of water, 3 g of 10% palladium-carbon were added thereto and reduction was performed in a hydrogen atmosphere at room temperature for 2 hours. After the reduction, 100 ml of water and 19.2 ml of a 4N aqueous solution of sodium hydroxide (76.67 mmol) were added thereto followed by stirring for a while, the catalyst was removed by filtration and the filtrate was concentrated. The residue was dissolved in 160 ml of water and an ion-exchange resin (Amberlite IR 120 B H AG (H$^+$)) was added thereto little by little until the solution became weakly acidic whereupon an excessive sodium was removed. To this were added 34.8 ml of a 28% aqueous ammonia solution and the ion-exchange resin was removed by filtration. The ion-exchange resin was washed with an 5% aqueous ammonia solution and the resulting aqueous solution after washing was combined with the filtrate followed by concentrating. The residue after concentration was dissolved in 100 ml of water and 1 g of active carbon was added to the solution followed by stirring for 10 minutes. The active carbon was removed by filtration, the filtrate was concentrated and the concentrate was crystallized by adding a 90% aqueous solution of ethanol thereto at room temperature to give 6.55 g (20.19 mmol; optical activity column HPLC purity: 99.3%) of a solvate of sodium salt crystals of monatin (2R,4R) substance with 0.2 molar equivalent of ethanol in an overall yield of 57.9%.

$^1$H-NMR (D$_2$O) δ: 1.95-2.02 (m, 1H), 2.58-2.62 (m, 1H), 3.01-3.05 (m, 1H), 3.21-3.24 (m, 1H), 3.55-3.58 (m, 1H), 7.07-7.11 (m, 1H), 7.14-7.18 (m, 2H), 7.42-7.44 (d, 1H), 7.66-7.68 (d, 1H).

ESI-MS: 291.49 (M−H)$^-$.

Melting point: 197.1-198.3° C.

Specific rotation (5% NH$_3$ water, c=0.5): $[\alpha]_D^{25}$=+0.64.

Degree of sweet taste: about 2700-fold (as compared with a 5% aqueous solution of sucrose).

Example 10

Conversion of Z-lactone (2S,4S) Substance into Sodium Salt Crystals of Monatin (2S,4S) Substance The same operation as in Example 9 was performed with the exception that 5.00 g (12.25 mmol; HPLC purity: 99.8%) of Z-lactone (2S,4S) substance were used in place of Z-lactone (2R,4R) substance and that reduction was performed in a hydrogen atmosphere at room temperature for 1 hour to give 3.15 g (9.71 mmol; optical activity column HPLC purity:

99.8%) of a solvate of sodium salt crystals of monatin (2S,4S) substance with 0.2 molar equivalent of ethanol in an overall yield of 79.3%.

$^1$H-NMR (D$_2$O) δ: the same as those in Example 9.

ESI-MS: 291.59 (M−H)$^−$.

Melting point: 196.1-197.9° C.

Specific rotation (5% NH$_3$ water, c=0.5): $[\alpha]_D^{25}$=−1.67.

Degree of sweetness: about 50-fold (as compared with a 5% aqueous solution of sucrose).

Example 11

Conversion of Z-lactone (2R,4S) Substance into Sodium Salt Crystals of Monatin (2R,4S) Substance.

The same operation as in Example 9 was performed with the exception that 3.66 g (8.59 mmol; HPLC purity: 97.3%) of a solvate of Z-lactone (2R,4S) substance with 0.2 molar equivalent of ethyl acetate were used in place of Z-lactone (2R,4R) substance and that reduction was performed in a hydrogen atmosphere at room temperature for 1 hour to give 2.23 g (7.07 mmol; optical activity column HPLC purity: 99.2%) of sodium salt crystals of monatin (2R,4S) substance in an overall yield of 82.3%.

$^1$H-NMR (D$_2$O) δ: 2.11-2.17 (m, 1H), 2.38-2.43 (m, 1H), 3.16 (s, 2H), 3.90-3.93 (m, 1H), 7.06-7.10 (m, 1H), 7.13-7.17 (m, 2H), 7.41-7.43 (d, 1H), 7.66-7.68 (d, 1H).

ESI-MS: 291.19 (M−H)$^−$.

Melting point: 227.5-229.2° C.

Specific rotation (5% NH$_3$ water, c=0.5): $[\alpha]_D^{25}$=+11.08.

Degree of sweetness: about 1300-fold (as compared with a 5% aqueous solution of sucrose).

FIG. 25 shows an optical microphotograph (magnification: 200-power) after drying of sodium salt crystals of a (2R,4S) monatin substance.

FIG. 26 is a powder X-ray diffraction chart after drying of sodium salt crystals of a (2R,4S) monatin substance. Characteristic diffraction X-ray peaks were noted at the angles of diffraction (2θ, CuKα line) of 4.4°, 13.7°, 16.6°, 17.9°, 18.6°, 20.2° and 22.6°.

Example 12

Conversion of Z-lactone (2S,4R) Substance into Sodium Salt Crystals of Monatin (2S,4R) Substance.

The same operation as in Example 9 was performed with the exception that 5.23 g (12.28 mmol; HPLC purity: 96.9%) of a solvate of Z-lactone (2S,4R) substance with 0.2 molar equivalent of ethyl acetate were used in place of Z-lactone (2R,4R) substance and that reduction was performed in a hydrogen atmosphere at room temperature for 1 hour followed by recrystallizing from a 90% aqueous solution of ethanol twice to give 2.57 g (8.14 mmol; optical activity column HPLC purity: 99.4%) of sodium salt crystals of monatin (2S,4R) substance in an overall yield of 66.3%.

$^1$H-NMR (D$_2$O) δ: same as those in Example 11.

ESI-MS: 291.49 (M−H)$^−$.

Melting point: 227.1-229.4° C.

Specific rotation (5% NH$_3$ water, c=0.5): $[\alpha]_D^{25}$=−9.57.

Degree of sweetness: about 300-fold (as compared with a 5% aqueous solution of sucrose).

FIG. 27 shows an optical microphotograph (magnification: 200-power) after drying of sodium salt crystals of a (2S,4R) monatin substance.

FIG. 28 is a powder X-ray diffraction chart after drying of sodium salt crystals of a (2S,4R) monatin substance. Characteristic diffraction X-ray peaks were noted at the angles of diffraction (2θ, CuKα line) of 4.4°, 13.7°, 16.6°, 17.9°, 18.6°, 20.2° and 22.6°.

Example 13

Preparation of Potassium Salt Crystals of (2R,4R) Monatin Substance (No. 1)

An ammonium salt (1.5 g) of (2R,4R) monatin substance was dissolved in 10 ml of water, passed through a column filled with 25 ml of a cation-exchange resin (Diaion PK 228 (potassium type; manufactured by Mitsubishi Chemical)) to exchange with a desired ion and the eluate was concentrated to an extent of 11.5 g. The resulting concentrate was heated up to 60° C. and 60 ml of ethanol were added thereto. The resulting aqueous ethanolic solution was cooled down to 10° C. at the rate of 5° C./hour and stirred at 10° C. for one night. Crystals were separated from the resulting crystallized solution and the wet crystals were dried in a vacuum drier to give 1.1 g of potassium salt crystals of (2R,4R) monatin substance.

Melting point: 213.3-214.7° C.

FIG. 1 shows an optical microphotograph (magnification: 200-power) immediately prior to separation of a crystallized solution of potassium salt crystals of a (2R,4R) monatin substance.

FIG. 2 shows an optical microphotograph (magnification: 200-power) after drying of the potassium salt crystals of a (2R,4R) monatin substance.

Figure 3:
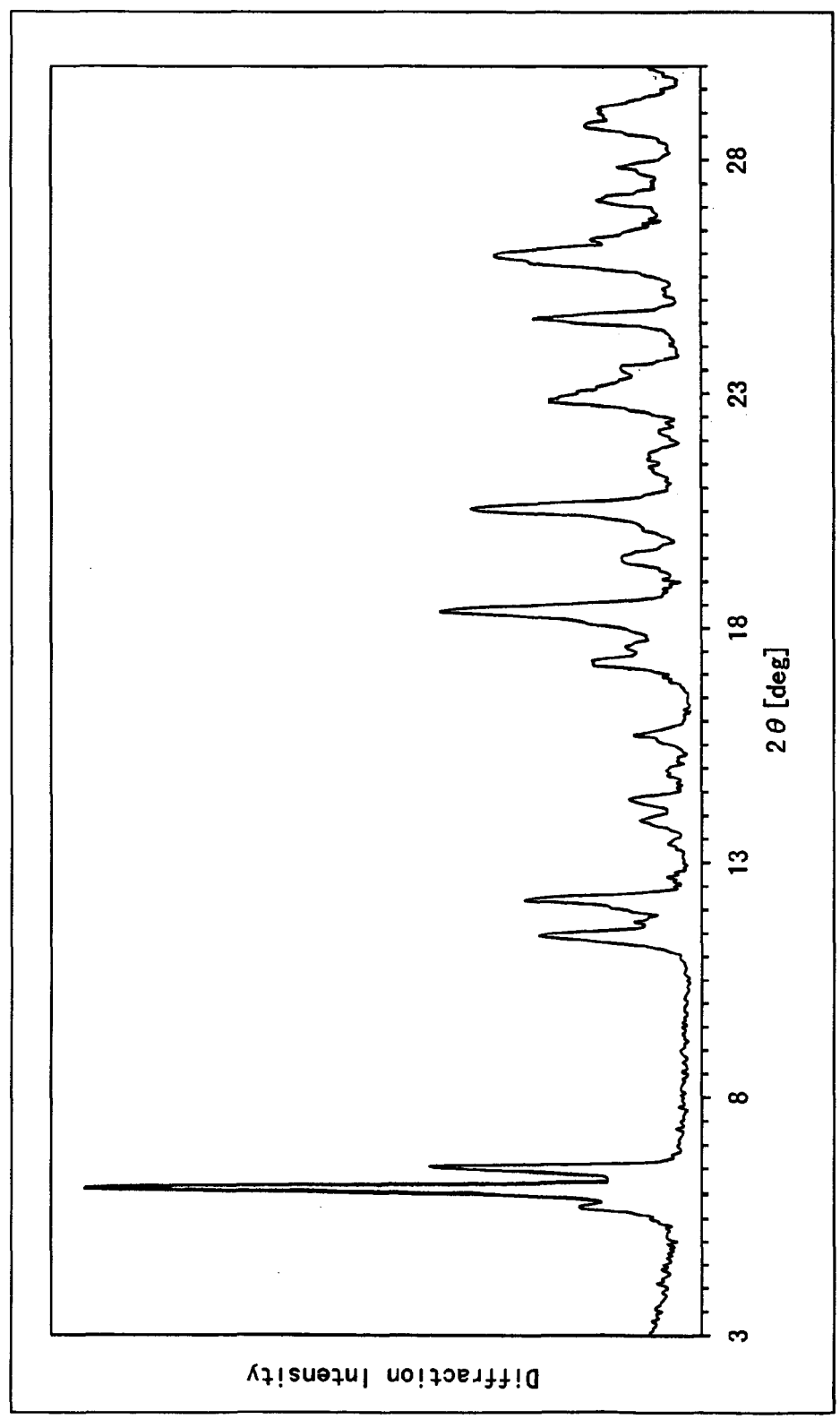
FIG. 3 is a powder X-ray diffraction chart after drying potassium salt crystals of a (2R,4R) monatin substance of Example 13.

FIG. 3 is a powder X-ray diffraction chart after drying potassium salt crystals of a (2R,4R) monatin substance. Characteristic diffraction X-ray peaks were noted at the angles of diffraction (2θ, CuKα line) of 5.7°, 6.1°, 6.6°, 11.5°, 11.8°, 12.2°, 13.9°, 17.2°, 18.3°, 20.6°, 22.9°, 24.50° and 26.3°.

Example 14

Preparation of Sodium Salt Crystals of a (2R,4R) Monatin Substance (No. 2).

An ammonium salt (1.5 g) of (2R,4R) monatin substance was dissolved in 10 ml of water, passed through a column filled with 25 ml of a cation-exchange resin (Diaion PK 228 (Na-type; manufactured by Mitsubishi Chemical)) to exchange to a desired ion and the eluate was concentrated to an extent of 11.5 g. The resulting concentrate was heated up to 60° C. and 60 ml of ethanol was added thereto. The aqueous ethanolic solution was cooled down to 10° C. at the rate of 5° C./hour and then stirred at 10° C. for one night.

Crystals were separated from the resulting crystallized solution and, then the wet crystals were dried in a vacuum drier to give 1.2 g of crystals of a solvate of sodium salt of a (2R,4R) monatin substance with 0.2 molar equivalent of ethanol.

Melting point: 193.5-195.1° C.

FIG. 4 shows an optical microphotograph (magnification: 200-power) immediately prior to separation of a crystallized solution of sodium salt crystals of a (2R,4R) monatin substance.

FIG. 5 shows an optical microphotograph (magnification: 200-power) after drying of the sodium salt crystals of a (2R, 4R) monatin substance.

FIG. 6 is a powder X-ray diffraction chart after drying sodium salt crystals of a (2R,4R) monatin substance. Characteristic diffraction X-ray peaks were noted at angles of diffraction (2θ, CuKα line) of 4.4°, 15.3°, 17.5°, 19.1° and 24.6°.

Example 15

Preparation of Ammonium Salt Crystals of (2R,4R) Monatin Substance.

An ammonium salt (1.5 g) of (2R,4R) monatin substance was dissolved in 10 ml of water. The solution was heated up to 60° C. and 60 ml of ethanol were added thereto. The aqueous ethanolic solution was cooled down to 10° C. at the rate of 5° C./hour and stirred at 10° C. for one night. Crystals were separated from the resulting crystallized solution and the wet crystals were dried in a vacuum drier to give 0.77 g of ammonium salt crystals of (2R,4R) monatin substance.

Melting point: 172.1-172.8° C.

FIG. 7 shows an optical microphotograph (magnification: 200-power) immediately prior to separation of a crystallized solution of ammonium salt crystals of a (2R,4R) monatin substance.

FIG. 8 shows an optical microphotograph (magnification: 200-power) after drying of ammonium salt crystals of a (2R, 4R) monatin substance.

FIG. 9 is a powder X-ray diffraction chart after drying of ammonium salt crystals of a (2R,4R) monatin substance. Characteristic diffraction X-ray peaks were noted at angles of diffraction (2θ, CuKα line) of 6.1°, 11.6°, 18.1°, 19.6° and 25.0°.

Comparative Example 1

Preparation of Crystals of a Free (2R,4R) Monatin Substance.

An ammonium salt (0.5 g) of (2R,4R) monatin substance was dissolved in 10 ml of a 50% aqueous solution of acetic acid and 25 ml of ethanol were added thereto at 25° C. during one hour. Stirring was further performed for 4.5 hours at 25° C. Crystals were separated from the resulting crystallized solution and the wet crystals were dried in a vacuum drier to give 0.38 g of crystals of a free (2R,4R) monatin substance.

Melting point: 175.2-176.1° C.

FIG. 10 shows an optical microphotograph (magnification: 200-power) immediately prior to separation of a crystallized solution of crystals of a free (2R,4R) monatin substance.

FIG. 11 shows an optical microphotograph (magnification: 200-power) after drying of crystals of a free (2R,4R) monatin substance.

FIG. 12 is a powder X-ray diffraction chart after drying of crystals of a free (2R,4R) monatin substance. Characteristic diffraction X-ray peaks were noted at angles of diffraction (2θ, CuKα line) of 5.9°, 17.9°, 19.2°, 23.9° and 27.8°.

Comparative Example 2

Preparation of Amorphous Solid of Potassium Salt of (2R,4R) Monatin Substance.

A potassium salt (1.0 g) of a (2R,4R) monatin substance manufactured according to Example 13 was dissolved in 10 ml of water and freeze-dried to give 0.97 g of amorphous solid of potassium salt of a (2R,4R) substance.

Melting point: 183.2-184.8° C.

FIG. 13 shows an optical microphotograph (magnification: 200-power) after drying of an amorphous solid of potassium salt of a (2R,4R) monatin substance.

FIG. 14 is a powder X-ray diffraction chart after drying of an amorphous solid of potassium salt of a (2R,4R) monatin substance. As will be apparent from this chart, the solid was amorphous.

Example 16

Comparison of Thermostability of the Crystals.

Each 50 mg of the crystals and the amorphous solid prepared by the above-mentioned methods were placed in a 4-ml vial and preserved (kept) at the temperature of 120° C. At that time, the vial was made in an open state. Each 2 mg of the sample were taken out after retention time of 3 hours, 7 hours and 24 hours and the rate (ratio) of decomposed products were determined by means of HPLC (high-performance liquid chromatography). Relation between the retention time and the rate of the decomposed products is shown in the following Table 3 and Table 4.

TABLE 3

Rate of Decomposed Product A
Area % to residual monatin

| Samples | Retention Time (hours) | | |
|---|---|---|---|
| | 3 | 7 | 24 |
| | Rate of Decomposed Product A (%) | | |
| Potassium salt crystals | 0.9% | 0.8% | 0.6% |
| Sodium salt crystals | 3.4% | 4.6% | 6.7% |
| Ammonium salt crystals | 1.9% | 3.8% | 11.8% |
| Free substance crystals | 2.0% | 3.8% | 5.3% |
| Amorphous solid | 3.4% | 3.9% | 8.9% |

TABLE 4

Rate of Decomposed Product B
Area % to residual monatin

| Samples | Retention Time (hours) | | |
|---|---|---|---|
| | 3 | 7 | 24 |
| | Rate of Decomposed Product B (%) | | |
| Potassium salt crystals | 0.1% | 0.2% | 0.3% |
| Sodium salt crystals | 2.1% | 3.6% | 7.5% |
| Ammonium salt crystals | 1.2% | 2.3% | 7.6% |
| Free substance crystals | 2.1% | 4.3% | 11.7% |
| Amorphous solid | 3.4% | 4.3% | 11.1% |

From the results above, it was noted that potassium salt shows minimum production of the decomposed products A and B and was particularly superior to other crystals in terms of stability. With regard to the decomposed product B, its production is less in crystals of various salts than free substance crystals and amorphous solid and, therefore, it is noted that crystals of such salts are superior in terms of stability.

Example 17

Preparation of Potassium Salt Crystals of (2R,4R) Monatin Substance (No. 2)

An ammonium salt (10 g) of a (2R,4R) monatin substance was dissolved in 20 ml of water and passed through a column filled with 50 ml of a cation-exchange resin (Diaion PK 228; potassium-type, manufactured by Mitsubishi Chemical) to exchange with a desired ion and an eluate was concentrated to an extent of 23.48 g. The resulting concentrate was heated up to 35° C. and 84 ml of ethanol were dropped thereinto during about 3 hours. The aqueous ethanolic solution was cooled down to 10° C. at the rate of 5° C./hour and stirred at 10° C. for one night. Crystals were separated from the resulting crystallized solution and the wet crystals were dried in a vacuum drier to give 9.3 g of potassium salt crystals of a (2R,4R) monatin substance.

Melting point: 220.0-222.3° C.

FIG. 15 is a powder X-ray diffraction chart after drying of crystals of potassium salt of a (2R,4R) monatin substance. Characteristic diffraction X-ray peaks were noted at the angles of diffraction (2θ, CuKα line) of 5.7°, 6.1°, 11.5°, 12.2°, 18.3°, 20.6° and 24.5°.

Example 18

Preparation of Potassium Salt Crystals of (2R,4R) Monatin Substance (No. 3).

Potassium salt crystals (1.5 g) of a (2R,4R) monatin substance prepared according to Example 17 were dissolved in 10 ml of water, the solution was cooled down to 10° C. and 60 ml of ethanol were dropped thereinto during about 2.5 hours. The aqueous ethanolic solution was stirred at 10° C. for one night. Crystals were separated from the resulting crystallized solution and the wet crystals were dried in a vacuum drier to give 1.2 g of potassium salt crystals of a (2R,4R) substance.

Melting point: 213.2-215.6° C.

FIG. 16 is a powder X-ray diffraction chart after drying of crystals of potassium salt of a (2R,4R) monatin substance. Characteristic diffraction X-ray peaks were noted at the angles of diffraction (2θ, CuKα line) of 5.7°, 6.6°, 11.5°, 11.8°, 17.2°, 22.9° and 23.1°.

Example 19

Steam Adsorption/Desorption Curve of the Crystals.

Steam adsorption/desorption curve for each of the potassium salt crystals (crystallized at 10° C., 35° C. and 60° C.) of a (2R,4R) monatin substance prepared by the above-mentioned methods was determined. The measurement data are shown in FIG. 29. Conditions for the measurement are as follows.

Apparatus: Automatic measuring apparatus for amounts of adsorption of steam, Belsorp 18, manufactured by Nippon Bell K. K.

Measuring method: Constant-volume gas adsorption method

Measuring conditions:
　Adsorption gas: $H_2O$
　Air thermostat temperature: 323K
　Adsorbing temperature: 298K
　Initial introducing pressure: 1.0 torr
　Introducing pressure difference: 0 torr
　Saturated steam pressure: 23.76 torr
　Adsorption cross section: 0.125 $nm^2$
　Maximum adsorbing pressure: 0.90
　Minimum adsorbing pressure: 0.10
　Equilibrium time: 300 sec Example 20

The sodium salt of (2R,4R) monatin substance prepared in Example 14 was stored for two days in a constant-moisture and constant-temperature device of 40° C. temperature and 75% humidity to give crystals in which ethanol in the crystals disappeared.

FIG. 30 is a powder X-ray diffraction chart after drying of sodium salt crystals of a (2R,4R) monatin substance. Characteristic diffraction X-ray peaks were noted at angles of diffraction (2θ, CuKα line) of 4.4°, 15.2°, 17.8°, 20.6° and 24.1°.

Example A

Preparation of Potassium Salt Crystals of (2R,4R) Monatin Substance.

The potassium salt crystals (400 mg) of a (2R,4R) monatin substance manufactured according to Example 17 were dissolved in 2.5 ml of water, the solution was heated up to 40° C. and 15 ml of methanol were slowly dropped thereinto with stirring. The aqueous methanolic solution was allowed to stand in a refrigerator of 10° C. for one night. The resulting crystals were separated to give 1.03 g of wet crystals of potassium salt of a (2R,4R) monatin substance.

FIG. 31 is a powder X-ray diffraction chart of wet potassium salt crystals of a (2R,4R) monatin substance. Characteristic diffraction X-ray peaks were noted at angles of diffraction (2θ, CuKα line) of 5.7°, 11.5°, 11.8°, 17.2° and 23.1°.

Example B

Preparation of Potassium Salt Crystals of (2R,4R) Monatin Substance

The same operation as in Example A was performed with the exception that ethanol was used in place of methanol to give 0.38 g of wet crystals of potassium salt of a (2R,4R) monatin substance (water content: 5.97%).

FIG. 32 is a powder X-ray diffraction chart of wet potassium salt crystals of a (2R,4R) monatin substance. Characteristic diffraction X-ray peaks were noted at angles of diffraction (2θ, CuKα line) of 5.7°, 6.1°, 11.5°, 11.8°, 12.2°, 17.2°, 18.3°, 20.6°, 23.1° and 24.5°.

Example C

Preparation of Potassium Salt Crystals of (2R,4R) Monatin Substance.

The same operation as in Example A was performed with the exception that isopropyl alcohol was used in place of methanol to give 0.38 g of wet crystals of potassium salt of a (2R,4R) monatin substance (water content: 9.85%).

FIG. 33 is a powder X-ray diffraction chart of wet potassium salt crystals of a is (2R,4R) monatin substance. Characteristic diffraction X-ray peaks were noted at angles of diffraction (2θ, CuKα line) of 5.7°, 11.5°, 11.8°, 17.2° and 23.1°.

Example D

Preparation of Potassium Salt Crystals of (2R,4R) Monatin Substance

The same operation as in Example A was performed with the exception that acetone was used in place of methanol to give 0.30 g of wet crystals of potassium salt of a (2R,4R) monatin substance (water content: 10.64%).

FIG. 34 is a powder X-ray diffraction chart of wet potassium salt crystals of a (2R,4R) monatin substance. Characteristic diffraction X-ray peaks were noted at angles of diffraction (2θ, CuKα line) of 5.7°, 11.5°, 11.8°, 17.2° and 23.1°.

Example E

Preparation of Potassium Salt Crystals of (2R,4R) Monatin Substance

The potassium salt crystals (400 mg) of a (2R,4R) monatin substance manufactured according to Example 17 were dissolved in 5 ml of water, the solution was heated up to 35° C. and 30 ml of ethanol were slowly dropped thereinto with stirring. The aqueous ethanolic solution was allowed to stand in a refrigerator of 10° C. for one night. The resulting crystals were separated to give 0.28 g of wet crystals of potassium salt of a (2R,4R) monatin substance (water content: 9.75%).

FIG. 35 is a powder X-ray diffraction chart of wet potassium salt crystals of a (2R,4R) monatin substance. Characteristic diffraction X-ray peaks were noted at angles of diffraction (2θ, CuKα line) of 5.7°, 11.5°, 11.8°, 17.2° and 23.1°.

Example F

Preparation of Potassium Salt Crystals of (2R,4R) Monatin Substance.

The potassium salt crystals (400 mg) of a (2R,4R) monatin substance manufactured according to Example 17 were dissolved in 1.7 ml of water, the solution was heated up to 35° C. and 10 ml of ethanol were slowly dropped thereinto with stirring. The aqueous ethanolic solution was allowed to stand in a refrigerator of 10° C. for one night. The resulting crystals were separated to give 0.38 g of wet crystals of potassium salt of a (2R,4R) monatin substance (water content: 9.45%).

FIG. 36 is a powder X-ray diffraction chart of wet potassium salt crystals of a (2R,4R) monatin substance. Characteristic diffraction X-ray peaks were noted at angles of diffraction (2θ, CuKα line) of 5.7°, 11.5°, 11.8°, 17.2° and 23.1°.

Example G

Preparation of Potassium Salt Crystals of (2R,4R) Monatin Substance.

The potassium salt crystals (400 mg) of a (2R,4R) monatin substance manufactured according to Example 17 were dissolved in 1.25 ml of water, the solution was heated up to 35° C. and 7.5 ml of ethanol were slowly dropped thereinto with stirring. The aqueous ethanolic solution was allowed to stand in a refrigerator of 10° C. for one night. The resulting crystals were separated to give 0.42 g of wet crystals of potassium salt of a (2R,4R) monatin substance (water content: 9.67%).

FIG. 37 is a powder X-ray diffraction chart of wet potassium salt crystals of a (2R,4R) monatin substance. Characteristic diffraction X-ray peaks were noted at angles of diffraction (2θ, CuKα line) of 5.7°, 11.5°, 11.8°, 17.2° and 23.1°.

Example H

Preparation of Potassium Salt Crystals of (2R,4R) Monatin Substance.

The potassium salt crystals (475 mg) of a (2R,4R) monatin substance manufactured according to Example 17 were dissolved in 5 ml of water, the solution was cooled down to 10° C. and 30 ml of ethanol were slowly dropped thereinto with stirring. The aqueous ethanolic solution was allowed to stand in a refrigerator of 10° C. for one night. The resulting crystals were separated to give 0.36 g of wet crystals of potassium salt of a (2R,4R) monatin substance (water content: 8.26%).

FIG. 38-1 is a powder X-ray diffraction chart of wet potassium salt crystals of a (2R,4R) monatin substance. Characteristic diffraction X-ray peaks were noted at angles of diffraction (2θ, CuKα line) of 5.7°, 6.1°, 11.5°, 11.8°, 12.2°, 17.2°, 18.3°, 20.6°, 23.1° and 24.5°.

The crystals were dried at 60° C. in vacuo to give crystals (water content: 2.11%) of potassium salt of a (2R,4R) monatin substance.

FIG. 38-2 is a powder X-ray diffraction chart after drying of potassium salt crystals of a (2R,4R) monatin substance. Characteristic diffraction X-ray peaks were noted at angles of diffraction (2θ, CuKα line) of 6.1°, 6.6°, 12.2°, 13.9°, 18.3°, 20.6°, 22.9°, 24.5° and 26.3°.

Example I

Preparation of Potassium Salt Crystals of (2R,4R) Monatin Substance.

The potassium salt crystals (400 mg) of a (2R,4R) monatin substance manufactured according to Example 17 were dissolved in 2.5 ml of water, the solution was heated up to 25° C. and 15 ml of ethanol were slowly dropped thereinto with stirring. The aqueous ethanolic solution was allowed to stand in a refrigerator of 10° C. for one night. The resulting crystals were separated to give 0.40 g of wet crystals of potassium salt of a (2R,4R) monatin substance (water content: 10.39%).

FIG. 39-1 is a powder X-ray diffraction chart of wet potassium salt crystals of a (2R,4R) monatin substance. Characteristic diffraction X-ray peaks were noted at angles of diffraction (2θ, CuKα line) of 5.7°, 6.1°, 11.5°, 11.8°, 12.2°, 17.2°, 18.3°, 20.6°, 23.1° and 24.5°.

The crystals were dried at 60° C. in vacuo to give crystals (water content: 1.69%) of potassium salt of a (2R,4R) monatin substance.

FIG. 39-2 is a powder X-ray diffraction chart after drying of potassium salt crystals of a (2R,4R) monatin substance. Characteristic diffraction X-ray peaks were noted at angles of diffraction (2θ, CuKα line) of 5.7°, 6.1°, 6.6°, 11.5°, 11.8°, 12.2°, 13.9°, 18.3°, 20.6°, 22.9°, 24.5° and 26.3°.

Example J

Preparation of Potassium Salt Crystals of (2R,4R) Monatin Substance.

The potassium salt crystals (213 mg) of a (2R,4R) monatin substance manufactured according to Example 17 were dissolved in 1.25 ml of water, the solution was heated up to 40° C. and 7.5 ml of ethanol were slowly dropped thereinto with stirring. The aqueous ethanolic solution was allowed to stand in a refrigerator of 10° C. for one night. The resulting crystals were separated to give 0.19 g of wet crystals of potassium salt of a (2R,4R) monatin substance (water content: 6.43%).

FIG. 40-1 is a powder X-ray diffraction chart of wet potassium salt crystals of a (2R,4R) monatin substance. Characteristic diffraction X-ray peaks were noted at angles of diffraction (2θ, CuKα line) of 5.7°, 6.1°, 11.5°, 11.8°, 12.2°, 17.2°, 18.3°, 20.6°, 23.1° and 24.5°.

The crystals were dried at 60° C. in vacuo to give crystals (water content: 5.43%) of potassium salt of a (2R,4R) monatin substance.

FIG. 40-2 is a powder X-ray diffraction chart after drying of potassium salt crystals of a (2R,4R) monatin substance. Characteristic diffraction X-ray peaks were noted at angles of diffraction (2θ, CuKα line) of 6.1°, 6.6°, 11.5°, 12.2°, 13.9°, 18.3°, 20.6°, 22.9°, 24.5° and 26.3°.

Example K

Preparation of Potassium Salt Crystals of (2R,4R) Monatin Substance.

The potassium salt crystals (217 mg) of a (2R,4R) monatin substance manufactured according to Example 17 were dissolved in 1.25 ml of water, the solution was heated up to 60° C. and 7.5 ml of ethanol were slowly dropped thereinto with stirring. The aqueous ethanolic solution was allowed to stand in a refrigerator of 10° C. for one night. The resulting crystals were separated to give 0.20 g of wet crystals of potassium salt of a (2R,4R) monatin substance (water content: 7.25%).

FIG. 41-1 is a powder X-ray diffraction chart of wet potassium salt crystals of a (2R,4R) monatin substance. Characteristic diffraction X-ray peaks were noted at angles of diffraction (2θ, CuKα line) of 5.7°, 6.1°, 11.5°, 11.8°, 12.2°, 17.2°, 18.3°, 20.6°, 23.1° and 24.5°.

The crystals were dried at 60° C. in vacuo to give crystals (water content: 4.79%) of potassium salt of a (2R,4R) monatin substance.

FIG. 41-2 is a powder X-ray diffraction chart after drying of potassium salt crystals of a (2R,4R) monatin substance. Characteristic diffraction X-ray peaks were noted at angles of diffraction (2θ, CuKα line) of 6.1°, 6.6°, 11.5°, 12.2°, 13.9°, 18.3°, 20.6°, 22.9°, 24.5° and 26.3°.

Example L

Preparation of Potassium Salt Crystals of (2R,4R) Monatin Substance.

An ammonium salt (420 mg) of a (2R,4R) monatin substance was dissolved in 25 ml of methanol at 45° C. and 0.3 ml of a 20% by weight methanolic solution of potassium hydroxide was slowly dropped thereinto with stirring. The methanolic solution was allowed to stand in a refrigerator of 10° C. for one night. The resulting crystals were separated to give 0.22 g of wet crystals of potassium salt of a (2R,4R) monatin substance (water content: 5.64%).

FIG. 42 is a powder X-ray diffraction chart of wet potassium salt crystals of a (2R,4R) monatin substance. Characteristic diffraction X-ray peaks were noted at angles of diffraction (2θ, CuKα line) of 5.7°, 6.1°, 6.6°, 11.5°, 11.8°, 12.2°, 13.9°, 17.2°, 18.3°, 22.9°, 23.1° and 26.3°.

Example M

Preparation of Potassium Salt Crystals of (2R,4R) Monatin Substance.

Methanol (25 ml) and 0.38 ml of a 20% by weight solution of potassium hydroxide in methanol were mixed and 400 mg of an ammonium salt of a (2R,4R) monatin substance were added thereto. The methanolic solution was stirred for one night at room temperature. The resulting slurry was separated to give 0.25 g of solid of potassium salt of a (2R,4R) monatin substance (water content: 5.42%).

FIG. 43 is a powder X-ray diffraction chart of potassium salt solid of a (2R,4R) monatin substance. As will be apparent from this chart, the solid was amorphous.

Example N

Potassium salt crystals (150 mg) of a (2R,4R) monatin substance manufactured according to Example 17 were allowed to stand in a constant-temperature vessel of 60° C. for one night.

FIG. 44 is a powder X-ray diffraction chart of potassium salt crystals of a (2R,4R) monatin substance (water content: 7.04%) stored at 60° C. Characteristic diffraction X-ray peaks were noted at angles of diffraction (2θ, CuKα line) of 6.1°, 12.2°, 18.3°, 20.6° and 24.5°.

Comparative Example N

The same operation as in Example N was performed with the exception that a refrigerator of 10° C. was used in place of the constant-temperature vessel of 60° C. and the crystals were allowed to stand for one night. A powder X-ray diffraction chart of the crystals (water content: 6.96%) was the same as that of FIG. 15.

Example O

The same operation as in Example N was performed with the exception that a constant-temperature vessel of 120° C. was used in place of the constant-temperature vessel of 60° C. and the crystals were allowed to stand for one night.

FIG. 45 is a powder X-ray diffraction chart of potassium salt crystals of a (2R,4R) monatin substance (water content: 4.73%) stored at 120° C. Characteristic diffraction X-ray peaks were noted at angles of diffraction (2θ, CuKα line) of 6.1°, 12.2°, 18.3°, 20.6° and 24.5°.

Example P

Potassium salt crystals (150 mg) of a (2R,4R) monatin substance manufactured according to Example 17 were allowed to stand in a desiccator kept at relative humidity of 97% for one night.

FIG. 46 is a powder X-ray diffraction chart of potassium salt crystals of a (2R,4R) monatin substance (water content: 8.61%) stored at relative humidity of 97%. Characteristic diffraction X-ray peaks were noted at angles of diffraction (2θ, CuKα line) of 5.7°, 11.5°, 11.8°, 17.2° and 23.1°.

Comparative Example P1

Potassium salt crystals (150 mg) of a (2R,4R) monatin substance manufactured according to Example 17 were allowed to stand for one night in a constant-temperature and constant-humidity device of relative humidity of 75%. A powder X-ray diffraction chart of the crystals (water content: 5.43%) was the same as that of FIG. 15.

Comparative Example P2

Potassium salt crystals (200 mg) of a (2R,4R) monatin substance manufactured according to Example G were allowed to stand for one night in a desiccator kept at relative humidity of 10%. A powder X-ray diffraction chart of the crystals was the same as that of FIG. 37.

Example Q

Potassium salt crystals (240 mg) of a (2R,4R) monatin substance manufactured according to Example F were dried in vacuo at 60° C.

FIG. 47 is a powder X-ray diffraction chart of potassium salt crystals of a (2R,4R) monatin substance (water content: 1.04%) which were dried in vacuo at 60° C. Characteristic diffraction X-ray peaks were noted at angles of diffraction (2θ, CuKα line) of 6.6°, 13.9°, 22.9° and 26.3°.

Comparative Example Q

Potassium salt crystals (150 mg) of a (2R,4R) monatin substance manufactured according to Example F were dried in vacuo at 40° C. A powder X-ray diffraction chart of the crystals was the same as that of FIG. 36.

Based on the foregoing results, the present invention provides a novel sweet taste substance in the crystals of a non-natural-type stereoisomer salt of monatin. These crystals may be used as an effective ingredient whereupon it is possible to provide a novel sweetener or a product such as beverage and food containing the same. Crystals of the stereoisomer salt have an excellent stability upon preservation, show a strong intensity of sweet taste, and express an excellent taste as a sweetener. Among the crystals herein, crystals of salts (such as potassium salt) of a (2R,4R) monatin substance are preferred as crystals of the non-natural-type stereoisomer salts and they have particularly excellent taste and stability upon preservation.

Within the scope of the present invention is a novel sweet taste substance (the above-mentioned crystals of the non-natural-type stereoisomer salt) having an excellent property as a sweetener or an ingredient thereof and as a component for giving sweet taste to beverage, food, etc.

Numerous modifications and variations on the present invention are possible in light of the above teachings. It is, therefore, to be understood that within the scope of the accompanying claims, the invention may be practiced otherwise than as specifically described herein.

The invention claimed is:

1. A crystalline salt of monatin selected from the group consisting of:
    (a) ammonium salt of (2R,4R)-monatin which has PXRD peaks at diffraction angles 2θ CuKα of 6.1°, 11.6°, 18.1°, 19.6°, and 25.0°;
    (b) sodium salt of (2R,4R)-monatin which has PXRD peaks at diffraction angles 2θ CuKα of 4.4°, 15.3°, 17.5°, 19.1°, and 24.6°;
    (c) sodium salt of (2R,4R)-monatin which has PXRD peaks at diffraction angles 2θ CuKα of 4.4°, 15.2°, 17.8°, 20.6°, and 24.1°;
    (d) potassium salt of (2R,4R)-monatin which has PXRD peaks at diffraction angles 2θ CuKα of 6.1°, 12.2°, 18.3°, 20.6°, and 24.5°;
    (e) potassium salt of (2R,4R)-monatin which has PXRD peaks at diffraction angles 2θ CuKα of 5.7°, 11.5°, 11.8°, 17.2°, and 23.1°; and
    (f) potassium salt of (2R,4R)-monatin which has PXRD peaks at diffraction angles 2θ CuKα of 6.6°, 13.9°, 22.9°, and 26.3°.

2. A crystalline salt of monatin according to claim 1, which is (a) ammonium salt of (2R,4R)-monatin which has PXRD peaks at diffraction angles 2θ CuKα of 6.1°, 11.6°, 18.1°, 19.6°, and 25.0°.

3. A crystalline salt of monatin according to claim 2, which has a chemical purity of at least 95%.

4. A crystalline salt of monatin according to claim 2, which has an optical purity of at least 94%.

5. A crystalline salt of monatin according to claim 1, which is (b) sodium salt of (2R,4R)-monatin which has PXRD peaks at diffraction angles 2θ CuKα of 4.4°, 15.3°, 17.5°, 19.1°, and 24.6°.

6. A crystalline salt of monatin according to claim 5, which has a chemical purity of at least 95%.

7. A crystalline salt of monatin according to claim 5, which has an optical purity of at least 94%.

8. A crystalline salt of monatin according to claim 1, which is (c) sodium salt of (2R,4R)-monatin which has PXRD peaks at diffraction angles 2θ CuKα of 4.4°, 15.2°, 17.8°, 20.6°, and 24.1°.

9. A crystalline salt of monatin according to claim 8, which has a chemical purity of at least 95%.

10. A crystalline salt of monatin according to claim 8, which has an optical purity of at least 94%.

11. A crystalline salt of monatin according to claim 1, which is (d) potassium salt of (2R,4R)-monatin which has PXRD peaks at diffraction angles 2θ CuKα of 6.1°, 12.2°, 18.3°, 20.6°, and 24.5°.

12. A crystalline salt of monatin according to claim 11, which has a chemical purity of at least 95%.

13. A crystalline salt of monatin according to claim 11, which has an optical purity of at least 94%.

14. A crystalline salt of monatin according to claim 1, which is (e) potassium salt of (2R,4R)-monatin which has PXRD peaks at diffraction angles 2θ CuKα of 5.7°, 11.5°, 11.8°, 17.2°, and 23.1°.

15. A crystalline salt of monatin according to claim 14, which has a chemical purity of at least 95%.

16. A crystalline salt of monatin according to claim 14, which has an optical purity of at least 94%.

17. A crystalline salt of monatin according to claim 1, which is (f) potassium salt of (2R,4R)-monatin which has PXRD peaks at diffraction angles 2θ CuKα of 6.6°, 13.9°, 22.9°, and 26.3°.

18. A crystalline salt of monatin according to claim 17, which has a chemical purity of at least 95%.

19. A crystalline salt of monatin according to claim 17, which has an optical purity of at least 94%.

20. A solid composition which comprises a crystalline salt of monatin selected from the group consisting of:
    (a) ammonium salt of (2R,4R)-monatin which has PXRD peaks at diffraction angles 2θ CuKα of 6.1°, 11.6°, 18.1°, 19.6°, and 25.0°;
    (b) sodium salt of (2R,4R)-monatin which has PXRD peaks at diffraction angles 2θ CuKα of 4.4°, 15.3°, 17.5°, 19.1°, and 24.6°;
    (c) sodium salt of (2R,4R)-monatin which has PXRD peaks at diffraction angles 2θ CuKα of 4.4°, 15.2°, 17.8°, 20.6°, and 24.1°;
    (d) potassium salt of (2R,4R)-monatin which has PXRD peaks at diffraction angles 2θ CuKα of 6.1°, 12.2°, 18.3°, 20.6°, and 24.5°;
    (e) potassium salt of (2R,4R)-monatin which has PXRD peaks at diffraction angles 2θ CuKα of 5.7°, 11.5°, 11.8°, 17.2°, and 23.1°; and
    (f) potassium salt of (2R,4R)-monatin which has PXRD peaks at diffraction angles 2θ CuKα of 6.6°, 13.9°, 22.9°, and 26.3°.

21. A solid composition according to claim 20, wherein said crystalline salt of monatin is (a) ammonium salt of (2R,4R)-monatin which has PXRD peaks at diffraction angles 2θ CuKα of 6.1°, 11.6°, 18.1°, 19.6°, and 25.0°.

22. A solid composition according to claim 21, wherein crystalline salt of monatin has a chemical purity of at least 95%.

23. A solid composition according to claim 21, wherein crystalline salt of monatin has an optical purity of at least 94%.

24. A solid composition according to claim 21, which further comprises at least one component selected from the group consisting of a saccharide, another artificial sweetener, and a natural sweetener.

25. A solid composition according to claim 20, wherein said crystalline salt of monatin is (b) sodium salt of (2R,4R)-monatin which has PXRD peaks at diffraction angles 2θ CuKα of 4.4°, 15.3°, 17.5°, 19.1°, and 24.6°.

26. A solid composition according to claim 25, wherein crystalline salt of monatin has a chemical purity of at least 95%.

27. A solid composition according to claim 25, wherein crystalline salt of monatin has an optical purity of at least 94%.

28. A solid composition according to claim 25, which further comprises at least one component selected from the group consisting of a saccharide, another artificial sweetener, and a natural sweetener.

29. A solid composition according to claim 20, wherein said crystalline salt of monatin is (c) sodium salt of (2R,4R)-monatin which has PXRD peaks at diffraction angles 2θ CuKα of 4.4°, 15.2°, 17.8°, 20.6°, and 24.1°.

30. A solid composition according to claim 29, wherein crystalline salt of monatin has a chemical purity of at least 95%.

31. A solid composition according to claim 29, wherein crystalline salt of monatin has an optical purity of at least 94%.

32. A solid composition according to claim 29, which further comprises at least one component selected from the group consisting of a saccharide, another artificial sweetener, and a natural sweetener.

33. A solid composition according to claim 20, wherein said crystalline salt of monatin is (d) potassium salt of (2R,4R)-monatin which has PXRD peaks at diffraction angles 2θ CuKα of 6.1°, 12.2°, 18.3°, 20.6°, and 24.5°.

34. A solid composition according to claim 33, wherein crystalline salt of monatin has a chemical purity of at least 95%.

35. A solid composition according to claim 33, wherein crystalline salt of monatin has an optical purity of at least 94%.

36. A solid composition according to claim 33, which further comprises at least one component selected from the group consisting of a saccharide, another artificial sweetener, and a natural sweetener.

37. A solid composition according to claim 20, wherein said crystalline salt of monatin is (e) potassium salt of (2R,4R)-monatin which has PXRD peaks at diffraction angles 2θ CuKα of 5.7°, 11.5°, 11.8°, 17.2°, and 23.1°.

38. A solid composition according to claim 37, wherein crystalline salt of monatin has a chemical purity of at least 95%.

39. A solid composition according to claim 37, wherein crystalline salt of monatin has an optical purity of at least 94%.

40. A solid composition according to claim 37, which further comprises at least one component selected from the group consisting of a saccharide, another artificial sweetener, and a natural sweetener.

41. A solid composition according to claim 20, wherein said crystalline salt of monatin is (f) potassium salt of (2R, 4R)-monatin which has PXRD peaks at diffraction angles 2θ CuKα of 6.6°, 13.9°, 22.9°, and 26.3°.

42. A solid composition according to claim 41, wherein crystalline salt of monatin has a chemical purity of at least 95%.

43. A solid composition according to claim 41, wherein crystalline salt of monatin has an optical purity of at least 94%.

44. A solid composition according to claim 41, which further comprises at least one component selected from the group consisting of a saccharide, another artificial sweetener, and a natural sweetener.

45. A method for making a liquid composition, said method comprising dissolving or suspending a crystalline salt of monatin in a liquid, wherein said crystalline salt of monatin is selected from the group consisting of:
(a) ammonium salt of (2R,4R)-monatin which has PXRD peaks at diffraction angles 2θ CuKα of 6.1°, 11.6°, 18.1', 19.6°, and 25.0°;
(b) sodium salt of (2R,4R)-monatin which has PXRD peaks at diffraction angles 2θ CuKα of 4.4°, 15.3°, 17.5°, 19.1°, and 24.6°;
(c) sodium salt of (2R,4R)-monatin which has PXRD peaks at diffraction angles 2θ CuKα of 4.4°, 15.2°, 17.8°, 20.6°, and 24.1°;
(d) potassium salt of (2R,4R)-monatin which has PXRD peaks at diffraction angles 2θ CuKα of 6.1°, 12.2°, 18.3°, 20.6°, and 24.5°;
(e) potassium salt of (2R,4R)-monatin which has PXRD peaks at diffraction angles 2θ CuKα of 5.7°, 11.5°, 11.8°, 17.2°, and 23.1°; and
(f) potassium salt of (2R,4R)-monatin which has PXRD peaks at diffraction angles 2θ CuKα of 6.6°, 13.9°, 22.9°, and 26.3°.

46. A method according to claim 45, wherein said crystalline salt of monatin is (a) ammonium salt of (2R,4R)-monatin which has PXRD peaks at diffraction angles 2θ CuKα of 6.1°, 11.6°, 18.1°, 19.6°, and 25.0°.

47. A method according to claim 46, wherein crystalline salt of monatin has a chemical purity of at least 95%.

48. A method according to claim 46, wherein crystalline salt of monatin has an optical purity of at least 94%.

49. A method according to claim 46, wherein said liquid composition further comprises at least one component selected from the group consisting of a saccharide, another artificial sweetener, and a natural sweetener.

50. A method according to claim 46, wherein said liquid composition is a beverage.

51. A method according to claim 45, wherein said crystalline salt of monatin is (b) sodium salt of (2R,4R)-monatin which has PXRD peaks at diffraction angles 2θ CuKα of 4.4°, 15.3°, 17.5°, 19.1°, and 24.6°.

52. A method according to claim 51, wherein crystalline salt of monatin has a chemical purity of at least 95%.

53. A method according to claim 51, wherein crystalline salt of monatin has an optical purity of at least 94%.

54. A method according to claim 51, wherein said liquid composition further comprises at least one component selected from the group consisting of a saccharide, another artificial sweetener, and a natural sweetener.

55. A method according to claim 51, wherein said liquid composition is a beverage.

56. A method according to claim 45, wherein said crystalline salt of monatin is (c) sodium salt of (2R,4R)-monatin which has PXRD peaks at diffraction angles 2θ CuKα of 4.4°, 15.2°, 17.8°, 20.6°, and 24.1°.

57. A method according to claim 56, wherein crystalline salt of monatin has a chemical purity of at least 95%.

58. A method according to claim 56, wherein crystalline salt of monatin has an optical purity of at least 94%.

59. A method according to claim 56, wherein said liquid composition further comprises at least one component selected from the group consisting of a saccharide, another artificial sweetener, and a natural sweetener.

60. A method according to claim 56, wherein said liquid composition is a beverage.

61. A method according to claim 45, wherein said crystalline salt of monatin is (d) potassium salt of (2R,4R)-monatin which has PXRD peaks at diffraction angles 2θ CuKα of 6.1°, 12.2°, 18.3°, 20.6°, and 24.5°.

62. A method according to claim 61, wherein crystalline salt of monatin has a chemical purity of at least 95%.

63. A method according to claim 61, wherein crystalline salt of monatin has an optical purity of at least 94%.

64. A method according to claim 61, wherein said liquid composition further comprises at least one component selected from the group consisting of a saccharide, another artificial sweetener, and a natural sweetener.

65. A method according to claim 61, wherein said liquid composition is a beverage.

66. A method according to claim 45, wherein said crystalline salt of monatin is (e) potassium salt of (2R,4R)-monatin which has PXRD peaks at diffraction angles 2θ CuKα of 5.7°, 11.5°, 11.8°, 17.2°, and 23.1°.

67. A method according to claim 66, wherein crystalline salt of monatin has a chemical purity of at least 95%.

68. A method according to claim 66, wherein crystalline salt of monatin has an optical purity of at least 94%.

69. A method according to claim 66, wherein said liquid composition further comprises at least one component selected from the group consisting of a saccharide, another artificial sweetener, and a natural sweetener.

70. A method according to claim 66, wherein said liquid composition is a beverage.

71. A method according to claim 45, wherein said crystalline salt of monatin is (f) potassium salt of (2R,4R)-monatin which has PXRD peaks at diffraction angles 2θ CuKα of 6.6°, 13.9°, 22.9°, and 26.3°.

72. A method according to claim 71, wherein crystalline salt of monatin has a chemical purity of at least 95%.

73. A method according to claim 71, wherein crystalline salt of monatin has an optical purity of at least 94%.

74. A method according to claim 71, wherein said liquid composition further comprises at least one component selected from the group consisting of a saccharide, another artificial sweetener, and a natural sweetener.

75. A method according to claim 71, wherein said liquid composition is a beverage.

\* \* \* \* \*